United States Patent
Ojima et al.

(10) Patent No.: US 10,280,183 B2
(45) Date of Patent: May 7, 2019

(54) THERAPEUTIC AGENT FOR TREATING TUMORS

(71) Applicant: THE RESEARCH FOUNDATION FOR THE STATE UNIVERSITY OF NEW YORK, Albany, NY (US)

(72) Inventors: Iwao Ojima, Port Jefferson, NY (US); Jacob Vineberg, Merrick, NY (US); Tao Wang, Jersey City, NJ (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 15/127,083

(22) PCT Filed: Mar. 18, 2015

(86) PCT No.: PCT/US2015/021343
§ 371 (c)(1),
(2) Date: Sep. 19, 2016

(87) PCT Pub. No.: WO2015/143092
PCT Pub. Date: Sep. 24, 2015

(65) Prior Publication Data
US 2017/0166591 A1    Jun. 15, 2017

Related U.S. Application Data

(60) Provisional application No. 61/954,908, filed on Mar. 18, 2014.

(51) Int. Cl.
| C07D 251/18 | (2006.01) |
| C07D 251/54 | (2006.01) |
| A61K 31/53  | (2006.01) |
| A61P 35/00  | (2006.01) |
| C07D 519/00 | (2006.01) |

(52) U.S. Cl.
CPC ............ C07D 519/00 (2013.01); A61K 31/53 (2013.01); A61P 35/00 (2018.01); C07D 251/18 (2013.01); C07D 251/54 (2013.01)

(58) Field of Classification Search
CPC .. C07D 251/18; C07D 251/54; C07D 519/00; A61K 31/53
USPC ............... 544/180, 198, 206, 207, 208, 219; 549/510; 514/245, 449
See application file for complete search history.

(56) References Cited

U.S. PATENT DOCUMENTS

| 7,335,770 B2 | 2/2008 | Timmer et al. |
| 2005/0004026 A1 | 1/2005 | Kasibhatla et al. |
| 2008/0020985 A1 | 1/2008 | Cai et al. |
| 2010/0093094 A1 | 4/2010 | Kissel et al. |

OTHER PUBLICATIONS

See Pimlott SL., Nucl. Med. Commun. 26(3): 183-188, 2005 (PubMed Abstract provided).*
International Search Report dated Jun. 18, 2015, issued in corresponding International Patent Application No. PCT/US15/21343.

* cited by examiner

*Primary Examiner* — Venkataraman Balasubramanian
(74) *Attorney, Agent, or Firm* — Scully Scott Murphy and Presser

(57) ABSTRACT

The present disclosure relates to a therapeutic agent of the formula:

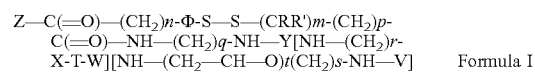

or a pharmaceutically acceptable salt thereof, useful for treating tumors, including cancers. Where the compound of Formula I also contains a radionuclide or an imaging agent or both, the compound of formula I is a theranostic agent useful for treating and diagnosing tumors, including cancers.

21 Claims, 5 Drawing Sheets

THERAPEUTIC AGENT FOR TREATING TUMORS

CROSS-REFERENCE TO RELATED APPLICATIONS

The present application claims benefit of U.S. Provisional Application No. 61/954,908, filed on Mar. 18, 2014, the contents of which are incorporated by reference.

STATEMENT REGARDING FEDERALLY SPONSORED RESEARCH

This invention was made with government support under grant number CA103314 awarded by the National Institutes of Health. The government has certain rights in the invention.

FIELD OF THE DISCLOSURE

This disclosure relates to a therapeutic agent, such as a biotinylated taxoid-based theranostic drug, for the treatment of tumors, especially cancer.

BACKGROUND OF THE DISCLOSURE

Accounting for nearly one quarter of total deaths in the United States, cancer remains the second leading cause of death behind heart disease. Traditional chemotherapy uses highly potent cytotoxic agents to interfere with the processes of cell proliferation, relying on the premise that rapidly proliferating tumor cells are more likely to be killed than normal cells. This lack of tumor-specificity continues to be a serious issue in cancer treatment, causing undesirable and dose-limiting side effects. Therefore, concentrated efforts have been directed toward the development of tumor-targeted drug delivery systems (TTDDSs), which consist of a tumor-targeting moiety (TTM) and a cytotoxic drug connected through a suitable linker system. These TTDDSs exploit the unique and intrinsic properties of cancer cells to selectively deliver cytotoxic agents to the tumor. An ideal linker system must remain stable during blood circulation, but be readily cleaved to release the active agent upon internalization or accumulation in the tumor microenvironment.

The problem is to find a TDDD that is capable of selectively delivering a cytotoxic agent that effectively kills tumor cells. The present disclosure describes such a TDDD.

SUMMARY OF THE DISCLOSURE

The present disclosure discloses a therapeutic agent of the formula:

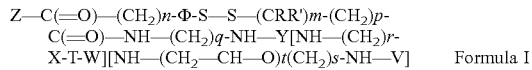

Formula I or a pharmaceutically acceptable salt thereof,
wherein,
Z is a hydroxy containing cytotoxic agent wherein the hydroxyl group thereon is replaced by O or O-Φ;
Φ is a phenyl ring;
R and R' are independently hydrogen or alkyl group containing 1 or 2 or 3 carbon atoms;
m and n and p are independently 1, 2, or 3,
Y is a triazine, including a 1,3,5-triazine;
r is 1, 2, or 3;
X is a triazole, including 1,2,3-triazole to which is optionally fused a cycloalkyl ring containing 5, 6, 7, 8, 9, or 10 carbon ring atoms;
T is O—(CH$_2$)a-C(=O)—, (CH$_2$—CH$_2$—O)o-(CH$_2$)f;
a is 1, 2, or 3;
W is Q$_b$-U$_d$ or halide or NH—C(=S)—NH—U or NH—C(=O)—(CH$_2$)$_{p1}$ [(CR1R2)$_{m1}$S—S-Φ[(CH$_2$)$_{n1}$]$_i$—C(=O)-A;
b and d are independently 0 or 1, wherein b and d cannot both be 0;
Q is a radionuclide;
U is an imaging modality;
o is 1, 2, 3, 4, 5, or 6;
i is 0 or 1;
f is 1, 2, or 3;
R1 and R2 are independently hydrogen or alkyl group containing 1 or 2 or 3 carbon atoms;
m$_1$ and n$_1$ and p$_1$ are independently 1, 2, or 3;
s is 1-6;
t is 1, 2, 3, 4, 5, or 6;
A is a hydroxy containing cytotoxic agent or O-Φ and
V is biotin or folic acid wherein the COOH moiety forms an amide bond with the NH group, wherein at least one of A and Z is a hydroxy containing cytotoxic agent.

An embodiment thereof has the formula II

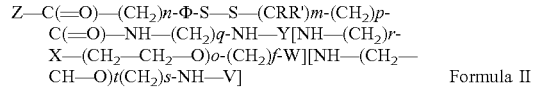

Formula II or a pharmaceutically acceptable salt thereof,
wherein,
Z is a taxoid identified by compound 3 wherein the hydroxyl group therein is replaced by O;
Φ is a phenyl ring;
R and R' are independently hydrogen or alkyl group containing 1 or 2 or 3 carbon atoms;
m and n and p are independently 1. 2, or 3,
Y is a triazine, including a 1,3,5-triazine;
r is 1, 2, or 3;
X is a triazole, including 1,2,3-triazole;
o is 1, 2, 3, 4, 5, or 6;
f is 1, 2, or 3;
W is a radionuclide or NH—C(=S)—NH—U;
U is an imaging modality;
s is 1-6;
t is 1, 2, 3, 4, 5, or 6; and
V is biotin or folic acid wherein the COOH moiety forms an amide bond with the NH group.

A further embodiment of the disclosure has the formula:

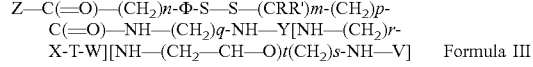

Formula III or a pharmaceutically acceptable salt thereof,
wherein,
Z is a taxoid identified by compound 3 wherein the hydroxyl group therein is replaced by O;
Φ is a phenyl ring;
R and R' are independently hydrogen or alkyl group containing 1 or 2 or 3 carbon atoms;
m and n and p are independently 1. 2, or 3,
Y is a triazine, including a 1,3,5-triazine;
r is 1, 2, or 3;
X is a triazole, including 1,2,3-triazole, to which is optionally fused a cycloalkyl ring containing 5, 6, 7, 8, 9, or 10 carbon ring atoms;

T is O—(CH$_2$)a-C(=O)—;
a is 1, 2, or 3;
W is Q$_b$-U$_d$;
Q is a radionuclide;
U is an imaging modality;
b and d are independently 0 or 1, wherein b and d cannot both be 0;
s is 1-6;
t is 1, 2, 3, 4, 5, or 6; and
V is biotin or folic acid wherein the COOH moiety forms an amide bond with the NH group.

Another aspect of this disclosure is directed to a pharmaceutical composition comprising the therapeutic agent of Formula I, II or III and a pharmaceutically acceptable carrier therefor.

A further aspect of the present disclosure is directed to a method of treating a tumor in a subject comprising administering to the subject in need thereof a therapeutically effective amount of the therapeutic agent of Formula I, II or III.

A further aspect of the present disclosure is directed to a method of diagnosing a tumor in a subject which comprises administering to a patient, who is suspect of having a tumor or who has a tumor, a diagnostically effective amount of the theranostic agent of Formula I, II or III having an imaging moiety or radionuclide moiety.

Another aspect of the present disclosure is directed to a compound of the formula:

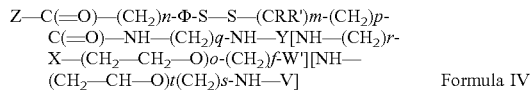
Z—C(=O)—(CH$_2$)n-Φ-S—S—(CRR')m-(CH$_2$)p-C(=O)—NH—(CH$_2$)q-NH—Y[NH—(CH$_2$)r-X—(CH$_2$—CH$_2$—O)o-(CH$_2$)f-W'][NH—(CH$_2$—CH—O)t(CH$_2$)s-NH—V]   Formula IV or pharmaceutically acceptable salt,
W' is a non-radioactive halide, such as F,
and Z, n, Φ, R, m, p, q, Y, r, X, o, f, t, s and V are as defined hereinabove.

A further aspect of the present disclosure is directed to a compound of the formula:

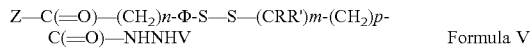
Z—C(=O)—(CH$_2$)n-Φ-S—S—(CRR')m-(CH$_2$)p-C(=O)—NHNHV   Formula V or pharmaceutically acceptable salt thereof, wherein
Z, n, Φ, R, R', m, p, q, and V are as defined hereinabove.

Another aspect of the present invention is directed to a pharmaceutical composition comprising a therapeutically effective amount of a compound of Formula IV or V and a pharmaceutically acceptable carrier therefor.

Another aspect of the present disclosure is directed to a method of treating tumor in a subject which comprises administering to the subject in need thereof an effective amount of the compound of Formula IV or V.

BRIEF DESCRIPTION OF THE DRAWING

The features and advantages of the disclosure will become apparent from the following non-limiting examples of various aspects of the present invention.

DETAILED DISCLOSURE

Figure 1:
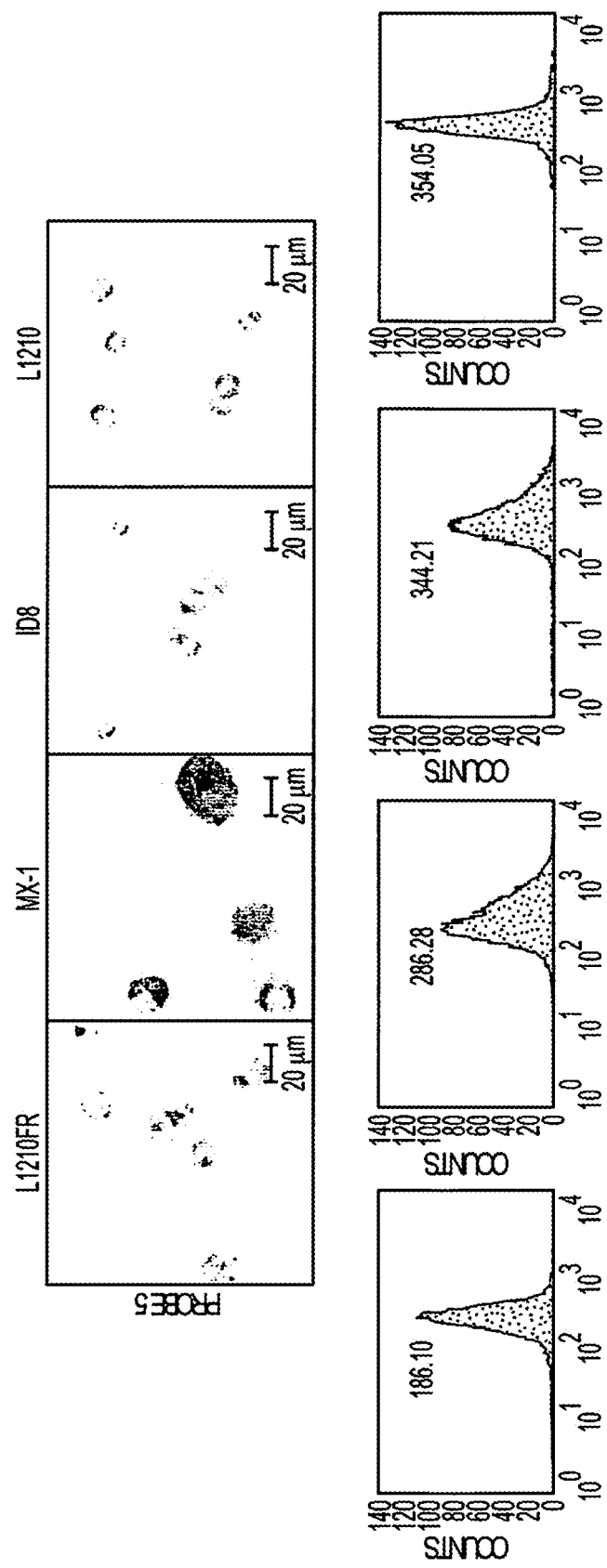
FIG. 1 is an assessment of non-specific internalization in L1210FR, MX-1, ID8, and L1210 cell lines based on the extent of internalization of fluorescent paclitaxel (5 μM) by flow cytometry and confocal fluorescence microscopy (CFM) at 3 h, 37° C.
Figure 2:
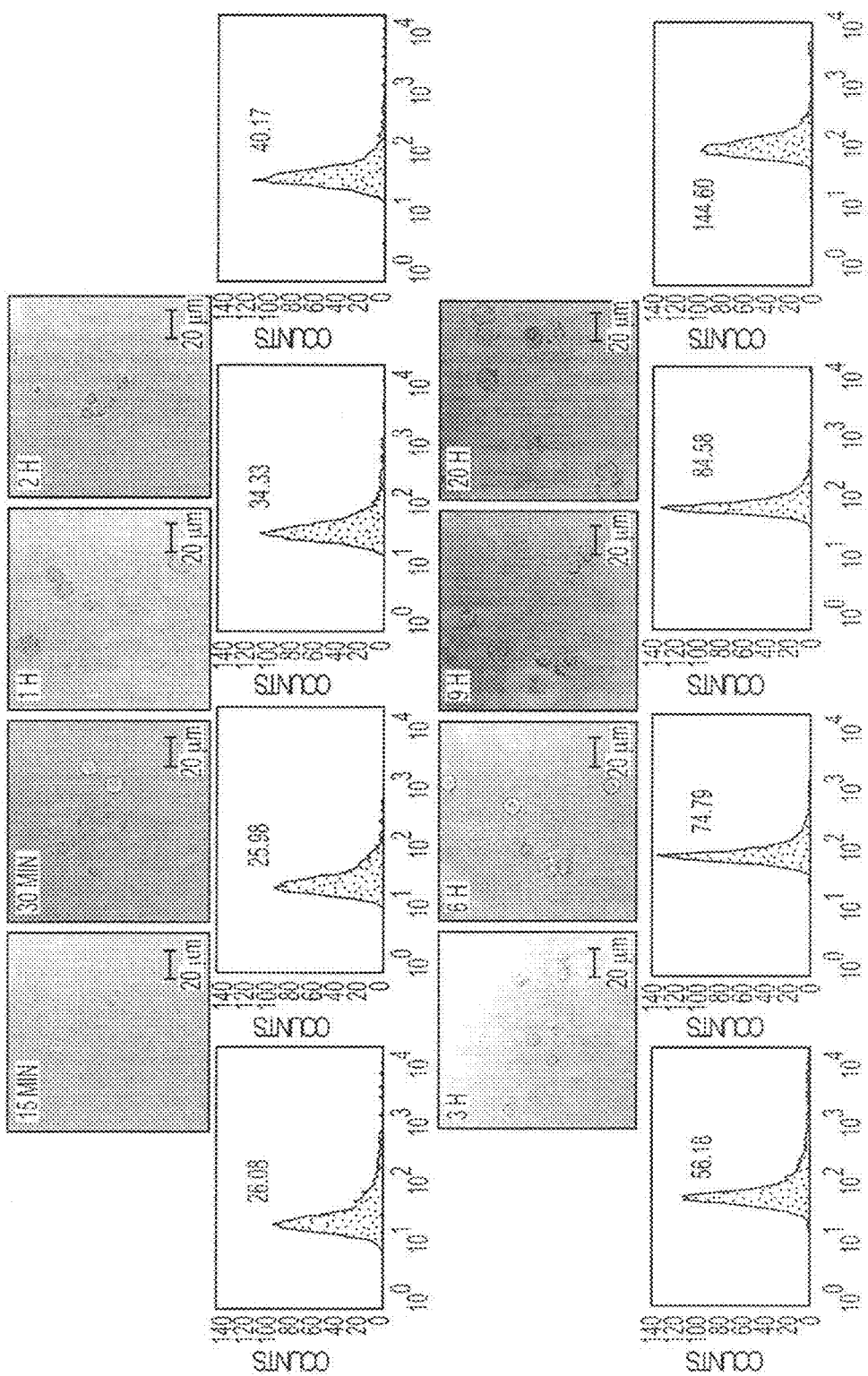
FIG. 2 is an assessment of the time-dependent internalization of theranostic conjugate 2 (5 μM) by RME in murine leukemia L1210FR (BR+) cell line based on the flow cytometry and confocal fluorescence microscopy analysis in the time period from 15 min to 24 h at 37° C.
Figure 3:
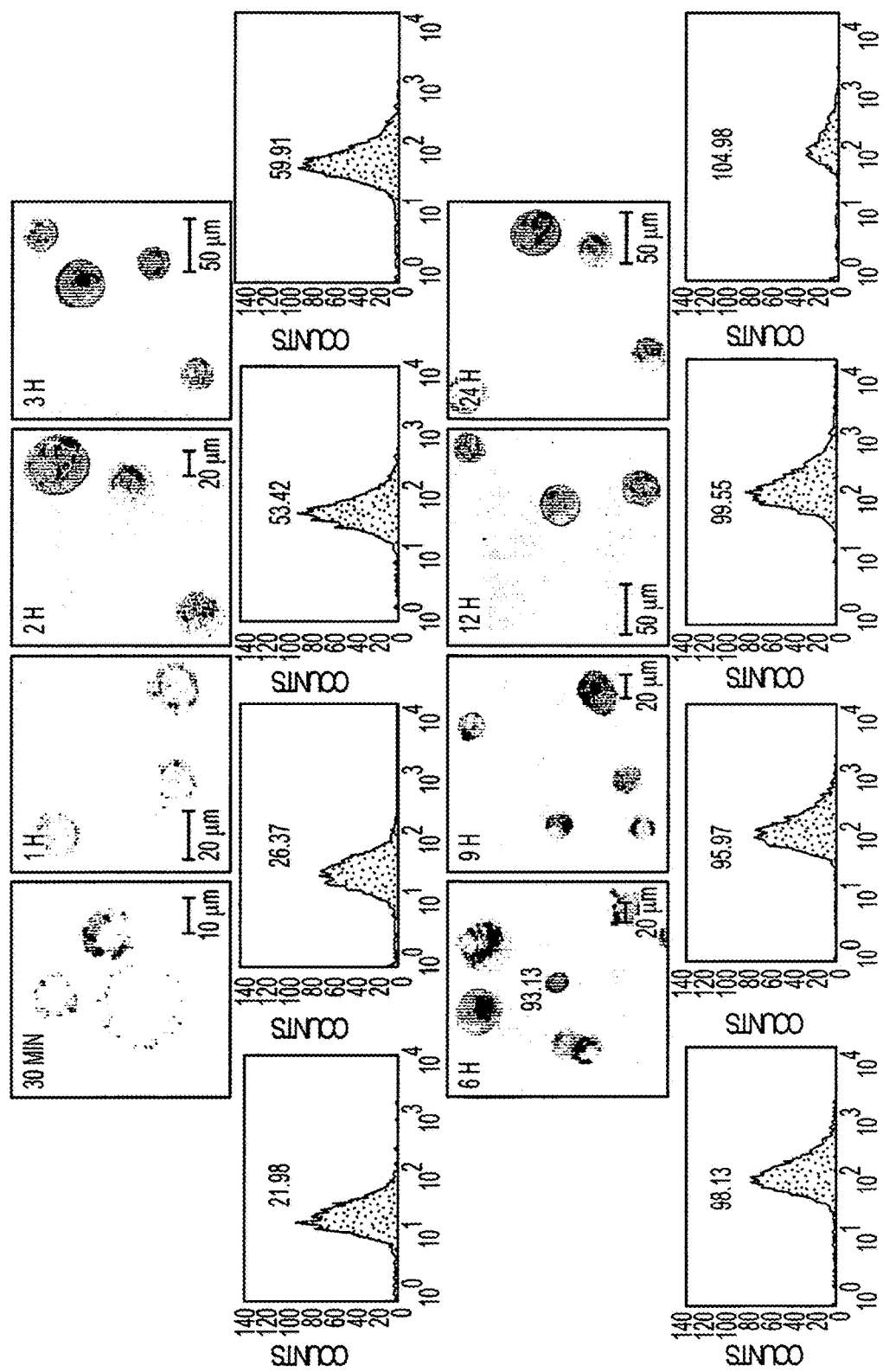
FIG. 3 is an assessment of the time-dependent internalization of 5 μM theranostic conjugate 2 by RME in human breast carcinoma MX-1 (BR+) cell line based on the flow cytometry and confocal fluorescence microscopy analysis in the time period from 30 min to 24 h at 37° C.

The present disclosure describes a TDDD that is a therapeutic agent. It contains both a modality that is overexpressed by the cancer cell on the surface thereof, such as a vitamin, e.g., folic acid or biotin and at least one cytotoxic agent thereon. The overexpressed modality is useful as a tumor-specific biomarker for TTDDS and targets the cancer cell. The cytotoxic agent thereon is cytotoxic to the cancer cell. In one embodiment, the therapeutic agent has one or two cytotoxic modalities thereon. Examples of cytotoxic modalities include a taxoid, such as depicted in compound 3 below, paclitaxel, docetaxel, camptothecin, topotecan or irinotecan, and the like.

In another embodiment, the present disclosure describes a TDDD that combines the modalities of therapy and diagnostic imaging. In other words, in this embodiment, the theranostic agent described herein delivers a therapeutic drug and diagnostic imaging agent at the same time within the same dose. By combining these features in one drug, the theranostic agent can overcome the undesirable differences in biodistribution and selectivity that currently exists between distinct imaging and therapeutic agents. Moreover, in this aspect, the theranostic agent of the present disclosure gives the physician the ability to image the cancer and monitor the tumor, the delivery kinetics, and the effectiveness of the therapeutic drug in one package and as a result fine-tune the therapy and dose thereof to the individual patient.

The therapeutic agent has thereon a triazine moiety, and more specifically 1,3,5-triazine. There are three substituents thereon, which are identified herein as legs. One leg contains the modality that is overexpressed in cancer cell, e.g., the vitamin, such as folic or biotin, such as the moiety identified as compound 3 herein. The second leg has the cytotoxic agent, such as the taxoid identified as compound 3, paclitaxel, docetaxel, camptothecin, topotecan or irinotecan, and the like. In the formula I herein, this moiety is depicted as Z. The cytotoxic drug has a hydroxyl group thereon, which forms an ester with the acyl group (C=O) of the C(=O)—(CH$_2$)n-Φ-S—S—(CRR')m-(CH$_2$)p-C(=O)— NH—(CH$_2$)q-NH— leg attached to the triazine. The third leg of the triazine contains either a radionuclide or halide or imaging agent or both a radionuclide and an imaging agent or another cytotoxic agent that has a hydroxyl group thereon. When the phenol or cytotoxic agent is part of this third leg, it form an ester linkage with the acyl group (C=O) of the NH—C(=O)—(CH$_2$)$_{p1}$[(CR1R2)$_{m1}$S—S—Φ-[(CH$_2$)$_{n1}$-]$_i$C(=O)-A that is attached to the A moiety depicted thereon.

Another portion of the TDDD is the linker. This linker is a disulfide linker, which is conjugated to a cytotoxic agent on one end and a tumor-targeting module on the other end.

These self-immolative linkers are stable during circulation in blood stream, but are readily cleavable in the tumor microenvironment. Once a drug conjugate is internalized into tumor cells following target-specific binding and receptor-mediated endocytosis (RME), the linker releases the drug warhead. Without wishing to be bound, it is believed that the linker is released through thiol-disulfide exchange with endogenous thiols, e.g., glutathione (GSH) and thioredoxin via facile benzothiolactonization. Since the GSH level in tumor tissues (2-8 mM) is more than 1,000 times higher than that in the blood stream (1-2 µM), GSH and other endogenous thiols serve as ideal tumor-specific triggers for drug release. The linker is a moiety of the formula —C(═O)—(CH$_2$)n-Φ-S—S—(CHR)m-(CH$_2$)p-C(═O)—, wherein Φ is a phenyl ring, R is hydrogen or alkyl group containing 1 or 2 or 3 carbon atoms and m and n and p are independently 1. 2, or 3.

It should be noted that when the therapeutic agent contains two cytotoxic modalities thereon, in one embodiment, both legs attached to the triazine has a disulfide linkage. Thus, the comments hereinabove regarding the thiol moiety are also applicable to this leg.

The other characteristic of the compounds of Formula I is that it has ethylene glycol oligomers thereon to enhance aqueous solubility.

An aspect of the present disclosure is directed to compounds of formula II, wherein Z, Φ, R, R', m, n, p, Y, r, X, T, a, W, Q, o, f, W, U, s, t and V are as defined hereinabove.

The compounds described hereinabove include pharmaceutically acceptable salts. The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The present disclosure is divided into three parts. All of the parts describe compounds which are generic to compounds of formula I. The first part describes in more detail the compounds of Formula II, while the second part describes in more detail the compounds of Formula III. The third part describes the compounds containing two cytotoxic agents or a cytotoxic agent and a surrogate. Since the compounds described herein are subgeneric to compounds of formula I, the comments hereinbelow in parts I, II and III are also applicable to the same variables in formula I.

I. The first two parts of the disclosure relates to therapeutic agents which contain the tumor-targeting modality, i.e. the leg of the triazine containing the moiety that is overexpressed on the surface of the cancer cells, e.g., folic acid or biotin, and the like; the cytotoxic moiety on the second leg of the triazine; and the imaging agent or radionuclide or both on the third leg of the triazine. When the therapeutic agent of the present invention has these three parts thereon, it is a theranostic agent, which has the characteristics described hereinabove.

The TDDD of this embodiment of the present disclosure consists of various parts. One part is a tumor-targeting module. It is a vitamin. Although vitamins are essential to the cellular growth and survival of all living cells, cancer cells require certain vitamins, such as biotin and folic acid, more than normal cells to sustain their growth and enhanced proliferation. In an embodiment, the tumor targeting module is biotin. Receptors for this vitamin are overexpressed on the surface of cancer cells to maintain extensive vitamin uptake.

Another portion of the TDDD is the cytotoxic agent, e.g., a taxoid of formula 3 indicated hereinbelow.

Another portion of the TDDD is the linker. This linker is a disulfide linker, which is conjugated to a cytotoxic agent on one end and a tumor-targeting module on the other end. As described hereinabove, these self-immolative linkers are stable during circulation in blood stream, but are readily cleavable in the tumor microenvironment. Once a drug conjugate is internalized into tumor cells following target-specific binding and receptor-mediated endocytosis (RME), the linker releases the drug warhead. Without wishing to be bound, it is believed that the linker is released through thiol-disulfide exchange with endogenous thiols, e.g., glutathione (GSH) and thioredoxin via facile benzothiolactonization. Since the GSH level in tumor tissues (2-8 mM) is more than 1,000 times higher than that in the blood stream (1-2 µM), GSH and other endogenous thiols serve as ideal tumor-specific triggers for drug release. The linker is a moiety of the formula —C(═O)—(CH$_2$)n-Φ-S—S—(CHR)m-(CH$_2$)p-C(═O)—, wherein Φ is a phenyl ring, R is hydrogen or alkyl group containing 1 or 2 or 3 carbon atoms and m and n and p are independently 1, 2, or 3.

In an embodiment, n is 1 or 2 and in another embodiment 1. The acyl moiety C(═O) forms an ester bond with the hydroxy moiety on compound 3. In another embodiment, m is 1 or 2 and in a further embodiment, m is 1. In another embodiment, p is 1 or 2 and in another embodiment, p is 2. In an embodiment, R is hydrogen, methyl or ethyl, or n-propyl, and R' is hydrogen or methyl. In a further embodiment, R is hydrogen or methyl and R' is hydrogen. In a further embodiment, R is methyl and R' is hydrogen. In a further embodiment, n is 1 or 2, m is 1 or 2, p is 1 or 2, and R is methyl and R' is hydrogen. In a further embodiment, R is methyl, R' is hydrogen, and m is 1 and n is 1 or 2 and p is 1 or 2. In a further embodiment, the —(CH$_2$)n and the S—S linkage are ortho substituted on the phenyl ring.

Another portion of the theranostic agent consists of a 1,3,5-triazine splitter module. This 1,3,5-triazine module is linked to the disulfide moiety described hereinabove by an amino-alkyl-amino linkage, i.e., NH—(CH$_2$)q-NH$_2$, wherein q is 1 to 3 in one embodiment, while in another embodiment, it is 1 or 2, and in another embodiment, it is 2 or 3 and in a further embodiment, it is 2. The splitter module which is a 1,3,5-triazine, is substituted on the 2, 4, and 6 positions of the triazine by three different legs. One leg is described hereinabove which is connected to the disulfide bridge by NH—(CH$_2$)q-NH—, another leg of the triazine molecule connects the imaging module to a triazine moiety described hereinabove through a click linker and the other leg of the triazine is connected through a linker to the biotin moiety.

Another portion of the theranostic agent consists of an imaging modality. The imaging modality is an imaging moiety for positron emission tomography (PET), e.g. a radioactive nuclide, or an imaging moiety for fluorescence imaging. This imaging modality is located on one of the legs of the triazine splitter moiety described hereinabove through a click linker and ethylene glycol oligomers. An example of the radioactive nuclide useful for PET is fluorine-18, cupper-64, gallium-68, and the like. When the theranostic agent contains the radioactive nuclide, the radioactive linker is linked to the click linker, as defined hereinbelow, by ethylene glycol bridges. Examples of fluorescent imaging agents are fluorescein, rhodamin, eosin, and the like. When the theranostic agent contains a fluorescent imaging agent, the fluorescent imaging agent is linked to a click linker by ethylene glycol bridges and aminothiocarbonylamino of the formula NH—C(=S)—NH.

The click linker is a 1,2, 3-triazole which is connected to the triazine by an aminoalkylene group of the formula NH—(CH$_2$)r, where r is 1, 2 or 3. In the theranostic agent, the NH group is connected directly to the triazine. In an embodiment, r is 1 or 2 and in another embodiment, it is 1.

Another leg of the triazine in this embodiment is connected to the tumor-targeting moiety, V, such as folic acid or biotin through NH—(CH$_2$—CH—O)t-(CH$_2$)s-NHC(=O)—(CH$_2$)uV, wherein s is 1-6, and t and u are independently 1,2, 3 or 4. In an embodiment, t is 2, 3, or 4, and in another embodiment, t is 2 or 3, and in another embodiment, t is 3. In an embodiment, s is 3-6, and in another embodiment, s is 4 or 5 and in another embodiment, s is 4. In an embodiment, u is 1 or 2 and in another embodiment, u is 1.

Examples of theranostic agents of Formula II are depicted herein below as compounds 1 and 2.

Compound 3 is the structure of taxoid 3 identified herein as SB-T-1214.

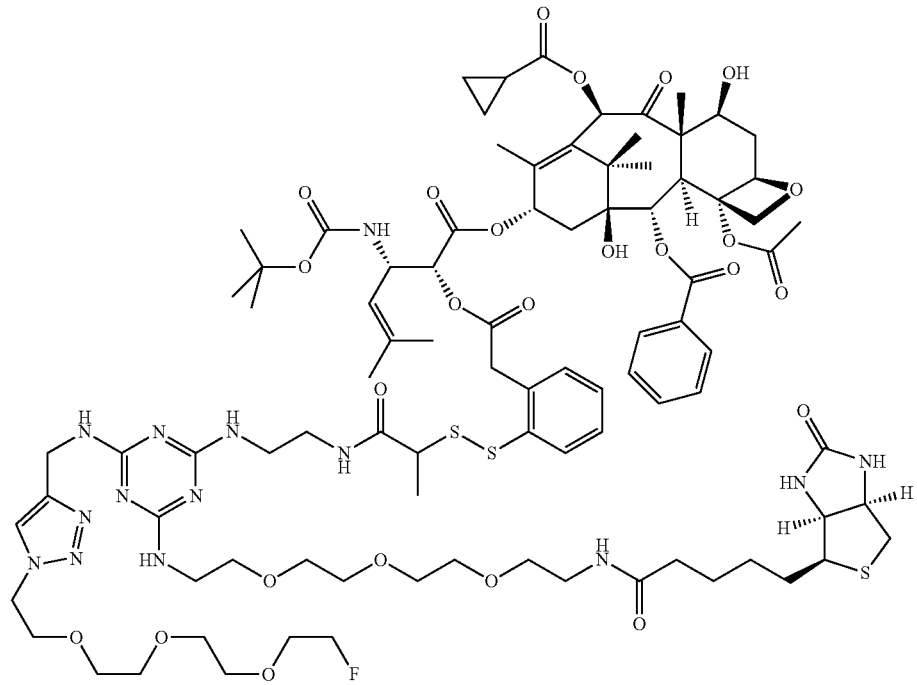

1

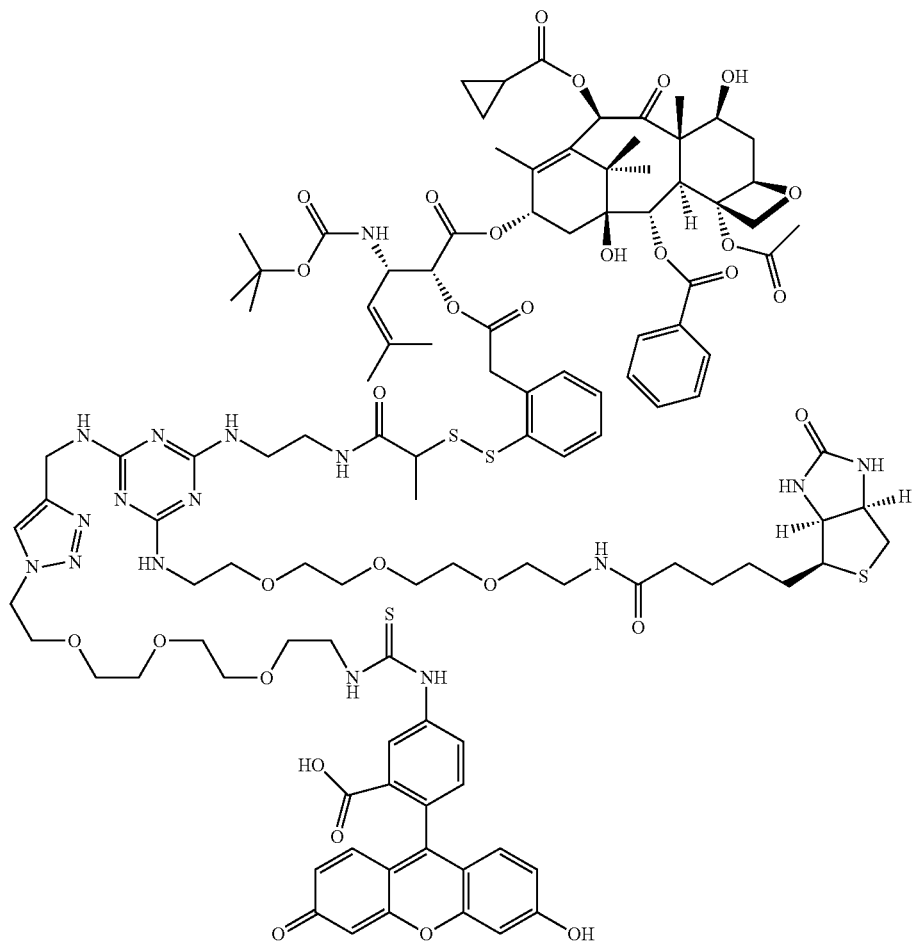

splitter
click linkage
PEG3 unit

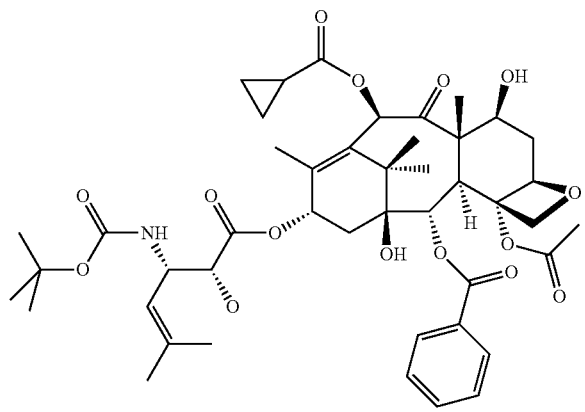

(SB-T-1214)

The compounds of the present invention are prepared by art recognized techniques. The procedures for preparing compounds 1 and 2 is exemplary of the procedures for preparing compounds of Formula II and, thus Formula I as well.

For the synthesis of theranostic conjugates 1 and 2, propargylaminotriazine-based biotin-linker-taxoid construct 7 was prepared, which is ready to attach an imaging module through "click" chemistry. The synthesis of construct 7 is illustrated in the following Scheme 1:

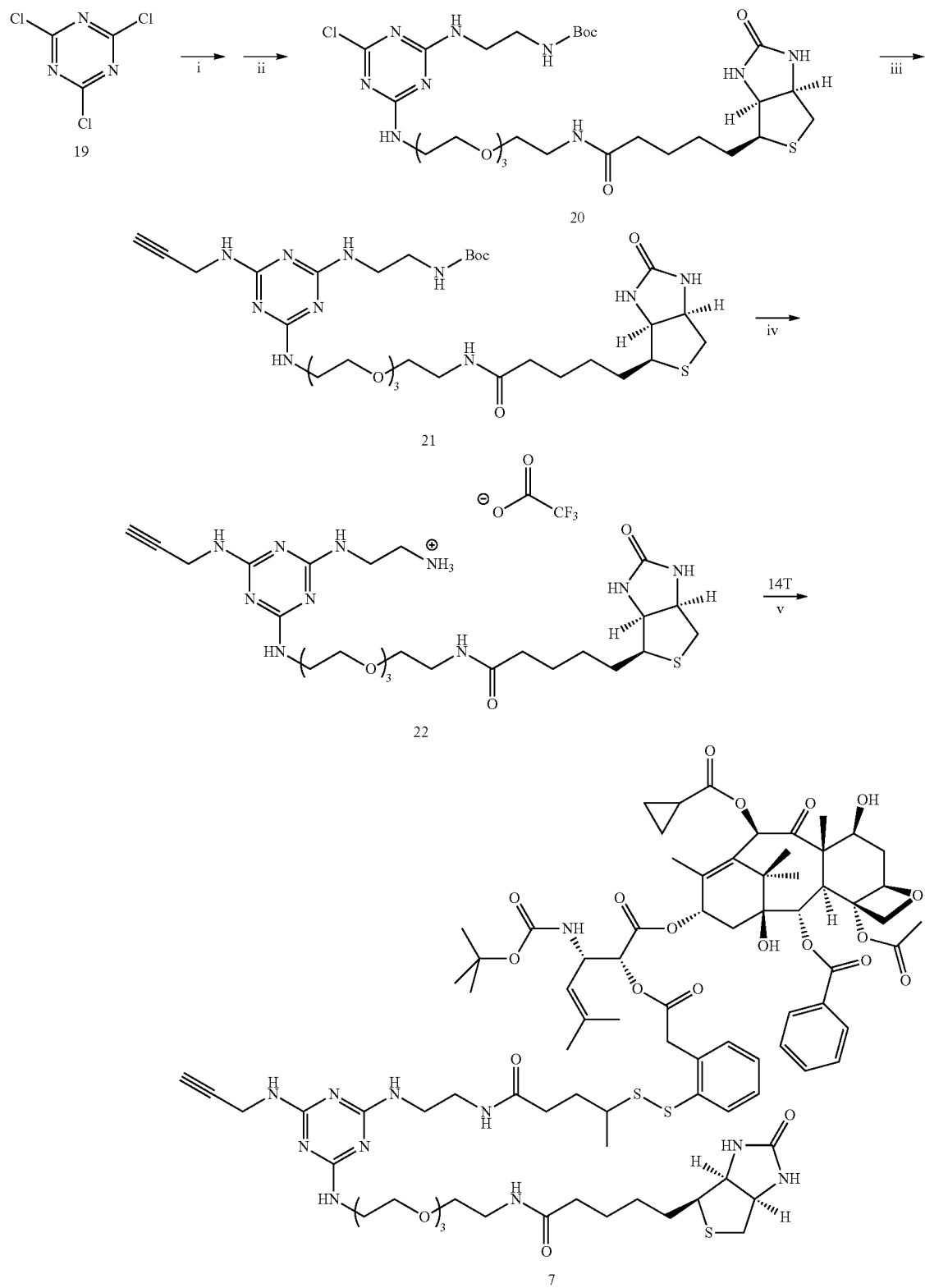
Scheme 1
aReagents and conditions: (i) N-Boc-ethylenediamine, DIPEA, 0° C.; 3 h (ii) biotinyl-NH-PEG3-NH2, DIPEA, 40° C., 16 h, 43% for two steps; (iii) propargylamine, DIPEA, THF, 50° C., 12 h, 69%; (iv) TFA, CH2Cl2, 25° C., 24 h, 99%; (v) CH2Cl2/pyridine, 25° C., 36 h, 73%

First, cyanuric acid (19) was reacted with N-Boc-ethylenediamine (1.0 equiv.) in the presence of N,N-diisopropylethylamine (DIPEA) at 0° C., followed by the subsequent substitution reaction with biotinyl-NH-PEG$_3$-NH$_2$ (6) (1.0 equiv.) in the presence of DIPEA at 40° C. to give 20 in moderate yield for 2 steps. The reaction of 20 with excess propargylamine in the presence of DIPEA at 50° C. afforded fully functionalized triazine 21 in 69% yield. The deprotection of 21 with TFA gave 22, which was reacted with 14T in the presence of pyridine in dichloromethane to give construct 7 as shown in Scheme 1.

Compound 14T is synthesized as follows:
The preparation of bifunctional disulfide linker unit 11 and its use for the synthesis of coupling-ready 14T is illustrated in Scheme 2. First, 4-sulfanylpentanoic acid (9) was prepared by ring-opening substitution of γ-valerolactone (8) with hydrobromic acid and thiourea, followed by basic hydrolysis. The thiol-disulfide exchange reaction of 9 with 4,4'-dipyridinedisulfide, followed by TIPS protection of the carboxylic acid moiety gave TIPS pyridinyldisulfanylpentanoate 10 in 92% yield for two steps. Another thiol-disulfide exchange reaction of 10 with 2-sulfanylphenylacetic acid afforded 11 in 68% yield. The coupling reactions of 11 with taxoid 3 in the presence of DIC and DMAP gave the corresponding drug-disulfide linker construct 12T in 79% yield. TIPS group of 12T, was removed with HF-pyridine to afford 13T.

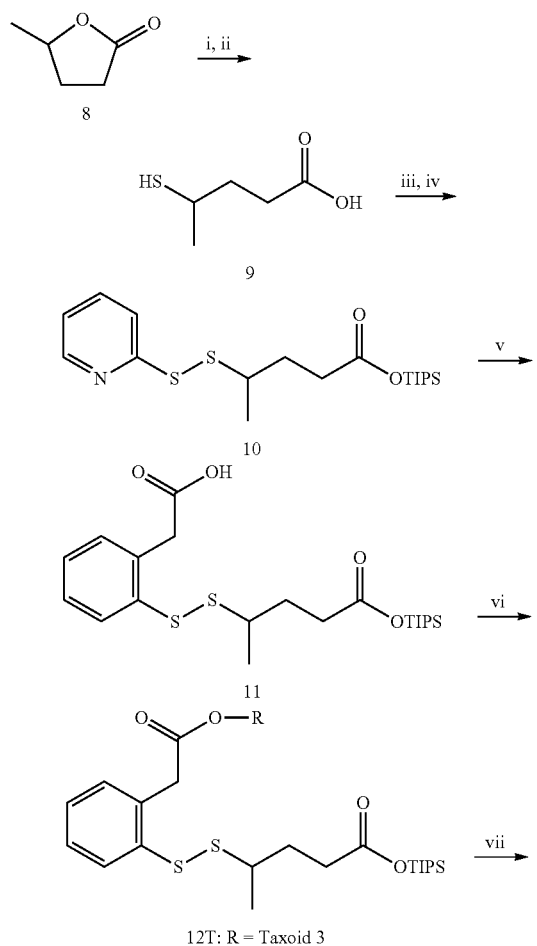

Scheme 2$^a$

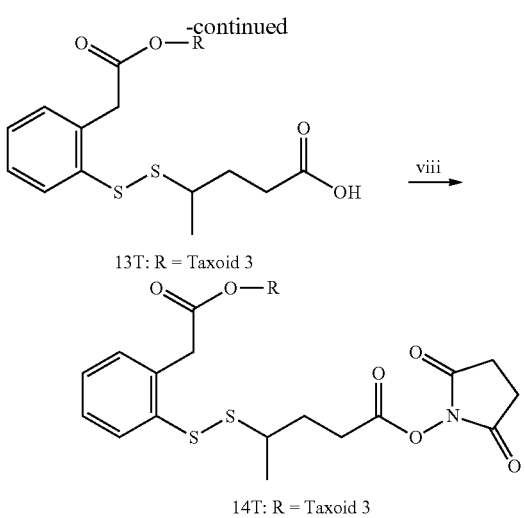

13T: R = Taxoid 3

14T: R = Taxoid 3

$^a$Reagents and conditions: (i) thiourea, 48% HBr, 100° C., 24 h; (ii) KOH, H$_2$O, 100° C., 24 h, 68%; (iii) 4,4'-dipyridinedisulfide, CH$_3$CH$_2$OH, 80° C., 2 h; (iv) i-Pr$_3$SiCl, Et$_3$N, CH$_2$Cl$_2$, 0→25° C., 24 h, 92%; (v) (2-sulfanylphenyl)acetic acid, THF, -10°C., 3 h, 68%; (vi) 1 or CPT or phenol, DIC, DMAP, CH$_2$Cl$_2$, 25° C., 24 h, 79%; (vii) 70% HF in pyridine, CH$_3$CN/pyridine (1:1), 0→25° C., 16 h, 91%; (viii) HOSu, EDC, THF/pyridine, 25° C., 36 h, 84%.

Then, the esterification of 13T with N-hydroxysuccinimide (HOSu) gave the corresponding coupling-ready taxoid-linker construct 14T, as an activated ester in high yield.

In the following scheme, reaction of 1-azido-11-methanesulfonyloxy-3,6,9-trioxaundecane (3) with TBAF at 85° C. gave fluorine-labeled-PEG$_3$-ethylazide 4 in 95% yield (Scheme 3). This process is amenable to fluorine-18. In a similar manner, the coupling of FITC with 1-amino-11-azido-3,6,9-trioxaundecane in the presence of DIPEA gave fluorescence-labeled-PEG$_3$-ethylazide 5 in 79% yield (Scheme 3). Then, construct 7, bearing an acetylene moiety, was subjected to copper(I)-catalyzed "click" reactions with azides 4 and 5 in the presence of copper(II) sulfate and ascorbic acid at 25° C. to give the corresponding conjugates 1 and 2 in 87 and 87% yields, respectively (Scheme 4).

Scheme 4$^a$

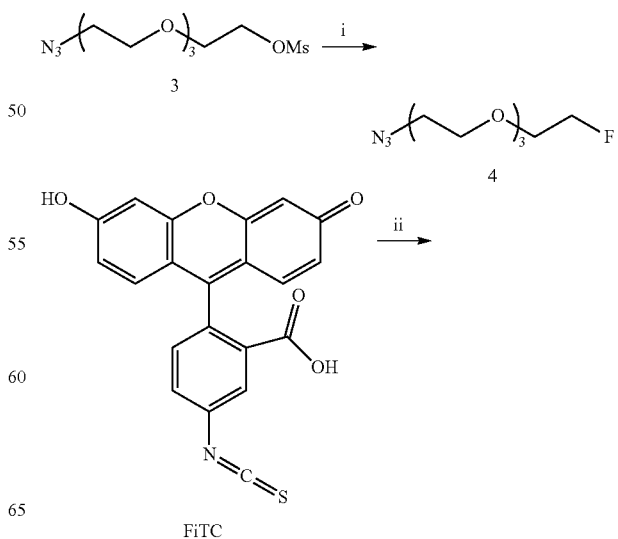

FITC

-continued

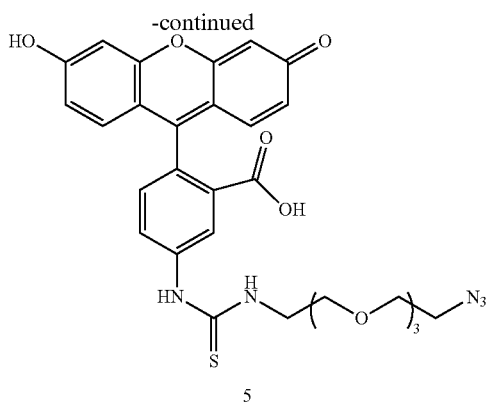

5

[a]Reagents and conditions: (i) TBAF, tert-amyl alcohol, 95%;
(ii) 1-1mino-11azido-3,6,9-trioxaundecne, Et₃N, DMSO, dark, 79%.

Scheme 4[a]

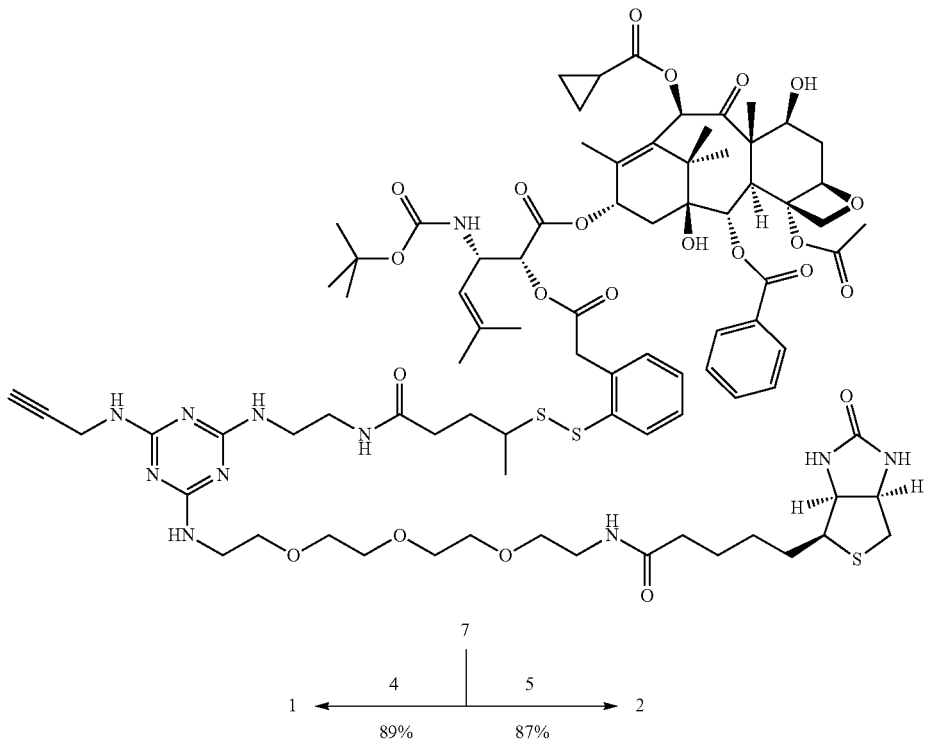

[a]Reagents and conditions: CuSO₄·5H₂O, ascorbic acid, THF/H₂O, pharmaceutical compositions, as discussed herein, in which a compound of formula I, such as compound 1 or 2, described herein is admixed together with one or more pharmaceutically acceptable carriers, which may additionally contain one or more excipients, buffers, adjuvants, stabilizers, or other materials, as described herein.

Suitable carriers, excipients, etc. can be found in standard pharmaceutical texts, for example, Remington's Pharmaceutical Sciences, 18th edition, Mack Publishing Company, Easton, Pa., 1990.

The pharmaceutical compositions may conveniently be presented in unit dosage form and may be prepared by any methods known in the art of pharmacy. Such methods include the step of bringing into association the active compound(s) with the carrier which constitutes one or more accessory ingredients. In general, the pharmaceutical compositions are prepared by uniformly and intimately bringing into association the active compound with liquid carriers or finely divided solid carriers or both, and then if necessary shaping the product.

While the compounds of Formula I, such as compound 1 or 2, herein may be administered alone in the methods described herein, it may also be presented as one or more pharmaceutical compositions (e.g., formulations). The aforementioned compounds may be formulated with one or more pharmaceutically acceptable carriers, adjuvants, excipients, diluents, fillers, buffers, stabilizers, preservatives, lubricants, or other materials well known to those skilled in the art. Accordingly, in an embodiment, a pharmaceutical composition is provided, comprising at least one compound of formula I, such as compound 1 or 2, and a pharmaceutically acceptable carrier therefor. The methods described herein include administration of one or more Pharmaceutical compositions may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Pharmaceutical compositions suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for parenteral administration (e.g. by injection, including cutaneous, subcutaneous, intramuscular, intravenous and intradermal), include aqueous and nonaqueous isotonic, pyrogen-free, sterile injection solutions which may contain anti-oxidants, buffers, preservatives, stabilizers, bacteriostats, and solutes which render the pharmaceutical composition isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such pharmaceutical compositions include Sodium Chloride Injection, Ringer's Solution, or Lactated Ringer's Injection. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Pharmaceutical compositions may be in the form of liposomes or other microparticulate systems which are designed to target the active compound to blood components or one or more organs.

Pharmaceutical compositions suitable for topical administration (e.g. transdermal, intranasal, ocular, buccal, and sublingual) may be formulated as an ointment, cream, suspension, lotion, powder, solution, past, gel, spray, aerosol, or oil. Alternatively, a pharmaceutical composition may comprise a patch or a dressing such as a bandage or adhesive plaster impregnated with active compounds and optionally one or more excipients or diluents.

Pharmaceutical compositions suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Pharmaceutical compositions suitable for topical administration to the eye also include eye drops wherein the active compound is dissolved or suspended in a suitable carrier, especially an aqueous solvent for the active compound.

Pharmaceutical compositions suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable pharmaceutical compositions wherein the carrier is a liquid for administration as, for example, nasal spray, nasal drops, or by aerosol administration by nebulizer, include aqueous or oily solutions of the active compound.

Pharmaceutical compositions suitable for administration by inhalation include those presented as an aerosol spray from a pressurized pack, with the use of a suitable propellant, such as dichlorodifluoromethane, trichlorofluoromethane, dichoro-tetrafluoroethane, carbon dioxide, or other suitable gases. Further pharmaceutical compositions suitable for inhalation include those administered in a nebulizer.

Pharmaceutical compositions suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical pharmaceutical compositions may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream pharmaceutical compositions.

Suitable emulgents and emulsion stabilizers include Tween 60, Span 80, cetostearyl alcohol, myristyl alcohol, glyceryl monostearate and sodium lauryl sulfate. The choice of suitable oils or fats for the pharmaceutical composition is based on achieving the desired cosmetic properties, since the solubility of the active compound in most oils likely to be used in pharmaceutical emulsion pharmaceutical compositions may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Pharmaceutical compositions suitable for rectal administration may be presented as a suppository with a suitable base comprising, for example, cocoa butter or a salicylate.

Pharmaceutical compositions suitable for vaginal administration may be presented as pessaries, tampons, creams, gels, pastes, foams or spray pharmaceutical compositions containing in addition to the active compound, such carriers as are known in the art to be appropriate.

It will be appreciated that appropriate dosages of the compounds and compositions comprising the active compounds of Formula I, including compound 1 or 2, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In an embodiment, a suitable dose of the active compound may be in the range of about 0.1 mg per kilogram to about 500 mg per kilogram body weight of the subject per day, in another embodiment, a suitable dose of the active compound may be in the range of about 1 mg per kilogram to about 100 mg per kilogram body weight of the subject per day, and in a still further embodiment, a suitable dose of the active compound may be in the range of about 5 mg per kilogram to about 50 mg per kilogram body weight of the subject per day.

The disclosure further provides a method of treating cancer in a subject in need of treatment, comprising administering the subject a therapeutically effective amount of a compound of Formula I, such as compound 1 or 2 described herein.

The disclosure further provides a method of reducing the proliferation of a cancer cell, comprising contacting the cancer cell with an effective amount of a compound of Formula I, such as compound 1 or 2, described herein.

Further, the disclosure further provides a method of diagnosing a tumor in a subject comprising administering to the subject in need thereof a diagnostically effective amount of the theranostic agent described herein. The amounts administered for the diagnostic utility are the same amounts described hereinabove for the therapeutic aspect.

In the present application, the term subject refers to a mammal. Examples include, but are not limited to, dog, cat, cow, sheep, donkey, mouse, rat, horse, human being, and the like. The preferred subject to which the compounds of Formula I is given is a human being.

The methods described herein can be used with any cancer, for example those described by the National Cancer Institute. The cancer can be a carcinoma, a sarcoma, a myeloma, a leukemia, a lymphoma or a mixed type. Exemplary cancers described by the National Cancer Institute include but are not limited to:

Digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

Endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor;

Eye cancers such as intraocular melanoma; and retinoblastoma;

Musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma;

Breast cancer such as breast cancer including childhood and male breast cancer and pregnancy;

Neurologic cancers such as childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor;

Genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Germ cell cancers such as childhood extracranial germ cell tumor; extragonadal germ cell tumor; ovarian germ cell tumor; and testicular cancer;

Head and neck cancers such as lip and oral cavity cancer; oral cancer including childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer;

Lymphoma (e.g., AIDS-related lymphoma; cutaneous T-cell lymphoma; Hodgkin's lymphoma including adult and childhood Hodgkin's lymphoma and Hodgkin's lymphoma during pregnancy; non-Hodgkin's lymphoma including adult and childhood non-Hodgkin's lymphoma and non-Hodgkin's lymphoma during pregnancy; mycosis fungoides; Sezary syndrome; Waldenstrom's macroglobulinemia; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders);

Lung cancer such as non-small cell lung cancer; and small cell lung cancer;

Respiratory cancers such as malignant mesothelioma, adult; malignant mesothelioma, childhood; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer;

Skin cancers such as Kaposi's sarcoma; Merkel cell carcinoma; melanoma; and childhood skin cancer;

AIDS-related malignancies;

Other childhood cancers, unusual cancers of childhood and cancers of unknown primary site;

and metastases of the aforementioned cancers.

In evaluating the biological activity of compounds of Formula II, such as compounds 1 or 2, additional probes were synthesized. One of such probes has the formula:

Z—C(=O)—(CH$_2$)n-Φ-S—S—(CRR')m-(CH$_2$)p-C(=O)—NHNHV    Formula V or pharmaceutically acceptable salt thereof, wherein Z, n, Φ, R, R', m, p, q, and V are as defined hereinabove. An example thereof has the Formula V, which is depicted hereinbelow. The compounds of Formula V, such as compound 15, are also tumor-specific cytotoxic agents and also useful for treating cancer. These compounds are smaller than compounds of Formula I and do not have ethylene glycol oligomers, or a triazine splitter module or the click linkage and are used for comparison with compounds of Formula I, such as compound 1, since it has exactly the same self-immolative disulfide linker unit thereof.

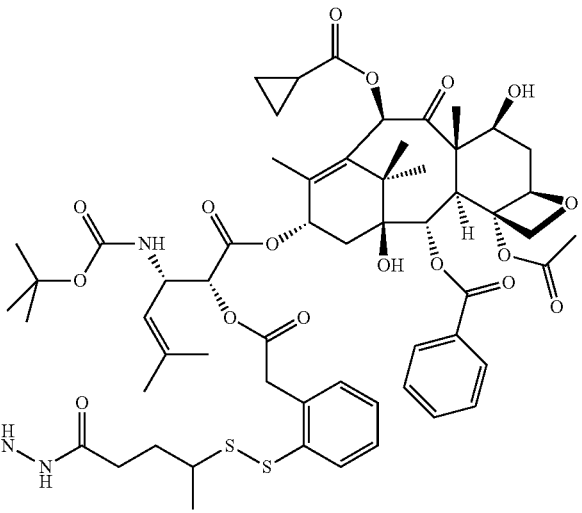

15

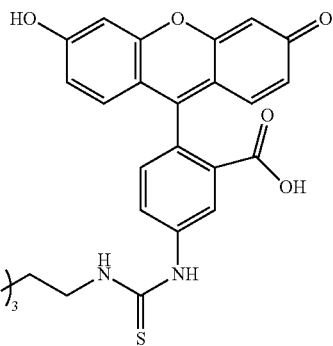

16

Other compounds were also prepared as fluorescent probes to examine a potential effect of molecular size on receptor-mediated endocytosis (RME) and ultimate efficacy of the TTTDS platform against cancer cell lines. Fluorescent probe 16 was designed as a small-molecule biotin probe to compare the effect of conjugate size on internalization via RME These compounds were prepared using art recognized techniques. The synthesis of compound 15 is exemplary for the synthesis of compounds of Formula V. Biotin-linkertaxoid conjugate 15 was synthesized through coupling of taxoid-linker activated ester 17 with biotinylhydrazine in moderate yield (Scheme 5).

Scheme 5[a]

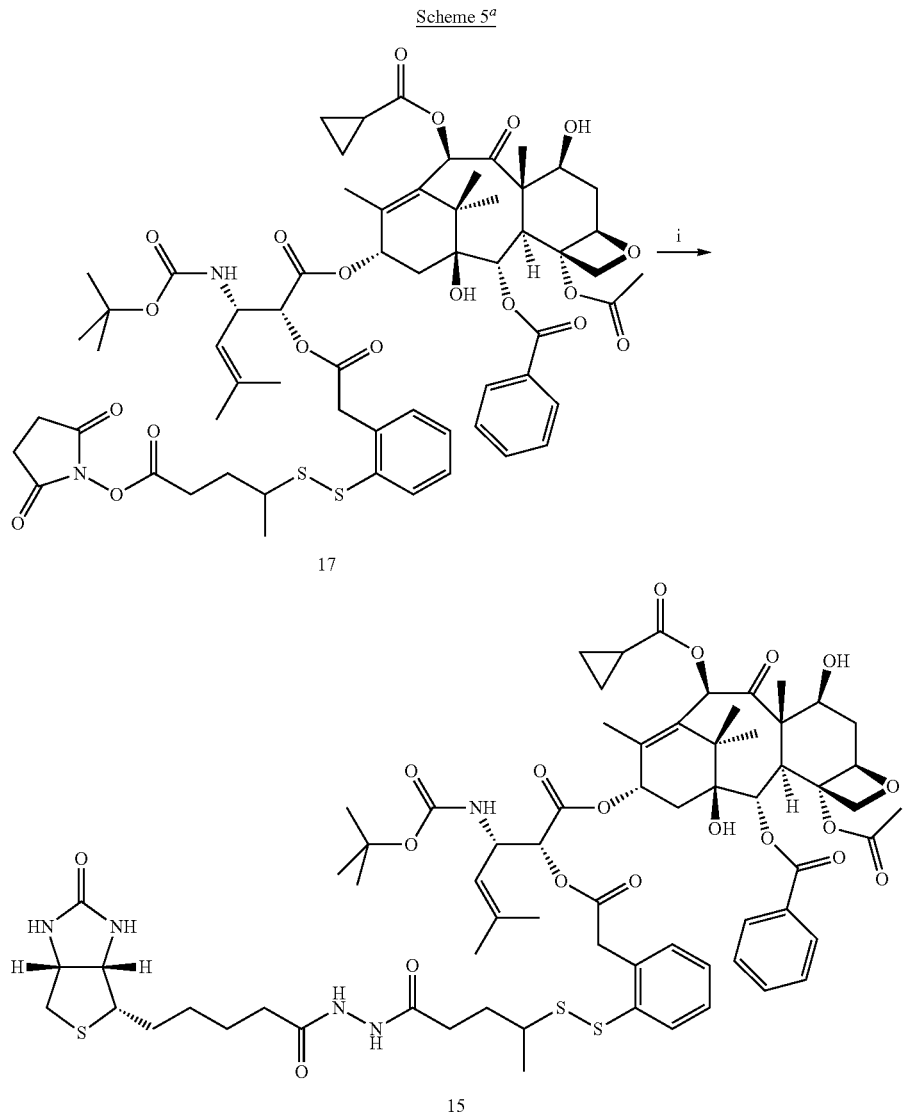

[a]Reagents and conditions: (i) biotinylhydrazine, pyridine, DMSO, 0 to 25C, 47%.

Biotin-linker-FITC probe 16 was synthesized through coupling of biotinyl-NH-PEG$_3$-(CH$_2$)$_2$—NH$_2$ with FITC in the same manner as that recently reported in Vineberg, J. G.; Zuniga, E. S.; Kamath, A.; Chen, Y. J.; Seitz, J. D.; Ojima, I. Design, Synthesis and Biological Evaluations of Tumor-Targeting Dual-Warhead Conjugates for a Taxoid-Camptothecin Combination Chemotherapy. *J. Med. Chem.* 2014, 57, 5777-5791, the contents of which are incorporated by reference.

It should be noted that the compounds of Formula V, such as compound 15, may be administered alone in the methods described herein, or they may also be presented as one or more pharmaceutical compositions (e.g., formulations). The aforementioned compounds may be formulated with one or more pharmaceutically acceptable carriers, adjuvants, excipients, diluents, fillers, buffers, stabilizers, preservatives, lubricants, or other materials well known to those skilled in the art. Accordingly, in an embodiment, a pharmaceutical composition is provided comprising at least one compound of Formula II, such as compound 15, and a pharmaceutically acceptable carrier therefor. The methods described herein include administration of one or more pharmaceutical compositions, as discussed herein, in which a compound of Formula II, such as compound 1 or 2, described herein is admixed together with one or more pharmaceutically acceptable carriers, which may additionally contain one or more excipients, buffers, adjuvants, stabilizers, or other materials, as described hereinabove for compounds of Formula I, the contents of which are incorporated by reference.

Suitable carriers, excipients, etc. can be found in standard pharmaceutical texts, for example, Remington's Pharmaceutical Sciences, 18th edition, Mack Publishing Company, Easton, Pa., 1990.

It will be appreciated that appropriate dosages of the compounds and compositions comprising the active compounds of Formula V, including compound 15, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In an embodiment, a suitable dose of the compound of formula II, such as compound 4, may be in the range of about 0.1 mg per kilogram to about 500 mg per kilogram body weight of the subject per day, in another embodiment, a suitable dose of the active compound may be in the range of about 1 mg per kilogram to about 100 mg per kilogram body weight of the subject per day, and in a still further embodiment, a suitable dose of the active compound may be in the range of about 5 mg per kilogram to about 50 mg per kilogram body weight of the subject per day.

The disclosure further provides a method of treating cancer in a subject in need of treatment, comprising administering the subject a therapeutically effective amount of a compound of Formula V, such as compound 15 described herein.

The disclosure further provides a method of reducing the proliferation of a cancer cell, comprising contacting the cancer cell with an effective amount of a compound of Formula V, such as compound 15, described herein. The cancers which compounds of Formula V, such as compound 15, are effective are the cancers listed hereinabove with respect to compounds of Formula V.

The following examples further illustrate the present disclosure.

EXAMPLES

General Methods. $^{1}$H, $^{13}$C and $^{19}$F NMR spectra were measured on a Bruker 300, 400, or 500 MHz spectrometer. Melting points were measured on a Thomas-Hoover capillary melting point apparatus and are uncorrected. TLC was performed on Sorbent Technologies aluminum-backed Silica G TLC plates (Sorbent Technologies, 200 μm, 20 cm×20 cm), and column chromatography was carried out on silica gel 60 (Merck, 230-400 mesh ASTM). Purity was determined with a Shimadzu L-2010A HPLC HT series HPLC assembly, using a Kinetex PFP column (4.6 mm×100 mm, 2.6 μm) with acetonitrile-water system. Two analytical HPLC conditions were used and noted as a part of the characterization data for literature unknown compounds, i.e., HPLC (A): flow rate 0.4 mL/min with a gradient of 15→95% acetonitrile for the 0-12 min period, then 95% acetonitrile for the 12-15 min period; HPLC (B): flow rate 0.4 mL/min, 95% acetonitrile flushing for the 0-15 min period. All new compounds possessed>95% purity. High resolution mass spectrometry analysis was carried out on an Agilent LC-UV-TOF mass spectrometer at the Institute of Chemical Biology and Drug Discovery, Stony Brook, N.Y. or at the Mass Spectrometry Laboratory, University of Illinois at Urbana—Champaign, Urbana, Ill.

Materials. The chemicals were purchased from Sigma-Aldrich, Fisher Scientific, and VWR International and used as received or purified before use by standard methods. Tetrahydrofuran was freshly distilled from sodium and benzophenone. Dichloromethane was also distilled immediately prior to use under nitrogen from calcium hydride. 10-Deacetylbaccatin III was a gift from Indena, SpA, Italy. 1-Azido-11-methanesulfonyl-oxy-3,6,9-trioxaundecane, 1-amino-11-azido-3,6,9-trioxaundecane, and biotinylhydrazine, were prepared by literature methods. 3-(4,5-Dimethylthiazol-2-yl)-2,5-diphenyltetrazolium bromide (MTT) was obtained from Sigma Chemical Co. Biological materials including RPMI-1640 and DMEM cell culture media, fetal bovine serum, NuSerum, PenStrep, and TrypLE were obtained from Gibco and VWR International, and used as received for cell-based assays.

Fluorine-labeled theranostic conjugate 1. To a solution of propargylaminotriazine construct 7 (27.8 mg, 0.0174 mmol) and ascorbic acid (3.4 mg, 0.0191 mmol) in THF (0.5 mL) was added 4 (4.2 mg, 0.0191 mmol) first, followed by an aqueous solution of $CuSO_4 \cdot 5H_2O$ (5 mg, 0.0191 mmol) in $H_2O$ (0.1 mL). The mixture was allowed to react at room temperature for 25 min, and the reaction mixture was diluted with $H_2O$ (10 mL) and extracted with $CH_2Cl_2$ (10 mL×3). The combined organic layers were dried over $MgSO_4$ and concentrated in vacuo to afford a milky white solid, which was triturated with hexanes (20 mL×4) and ethyl acetate (20 mL×4) to afford 1 (27 mg, 87%) as a white solid: mp 100-101° C.; $^{1}$H NMR (500 MHz, $CD_3OD$) δ 0.90-1.02 (m, 7H), 1.08 (m, 1H), 1.16 (s, 3H), 1.17 (s, 3H), 1.24 (d, J=6.8 Hz, 3H), 1.28 (m, 5H), 1.39 (m, 1H), 1.40 (s, 9H), 1.61 (m, 4H), 1.64 (s, 3H), 1.73 (s, 3H), 1.75 (s, 3H), 1.78 (m, 2H), 1.86 (m, 1H), 1.91 (s, 3H), 2.18 (t, J=7.5 Hz, 2H), 2.22 (m, 3H), 2.38 (s, 3H), 2.54 (m, 2H), 2.68 (d, J=12.8 Hz, 1H), 2.84 (m, 1H), 2.90 (dd, J=5.0, 12.8 Hz, 1H), 3.16 (m, 1H), 3.34 (m, 3H), 3.41 (bs, 2H), 3.48 (m, 2H), 3.52 (t, J=5.4 Hz, 2H), 3.61 (m, 4H), 3.65 (m, 20H), 3.71 (m, 2H), 3.85 (m, 3H), 4.00 (d, J=16.8 Hz, 1H), 4.09 (d, J=16.8 Hz, 1H), 4.20 (d, J=8.4 Hz, 1H), 4.24 (d, J=8.4 Hz, 1H), 4.27 (dd, J=4.4 Hz, 8.0 Hz, 1H), 4.31 (m, 1H), 4.46 (m, 1H), 4.49 (m, 2H), 4.52 (m, 2H), 4.92 (bs, 2H), 5.00 (d, J=8.4 Hz, 1H), 5.27 (bs, 1H), 5.67 (d, J=7.2 Hz, 1H), 6.31 (bt, J=8.5 Hz, 1H), 6.45 (s, 1H), 7.24 (m, 1H), 7.30 (m, 2H), 7.50 (t, J=7.7 Hz, 2H), 7.63 (t, J=7.5 Hz, 1H), 7.77 (m, 1H), 7.91 (bs, 1H), 8.12 (d, J=7.5 Hz, 2H); $^{13}$C NMR (125 MHz, $CD_3OD$) δ 7.79, 7.83, 9.05, 12.41, 13.04, 13.68, 14.04, 17.27, 19.59, 19.65, 20.97, 21.89, 22.30, 24.71, 25.47, 25.60, 27.41, 28.09, 28.37, 31.29, 31.35, 32.99, 33.08, 33.35, 36.15, 38.10, 38.99, 39.48, 39.77, 40.02, 43.21, 45.96, 46.06, 46.68, 50.09, 50.38, 55.69, 57.90, 60.20, 61.96, 65.52, 68.99, 69.19, 69.65, 69.74, 69.84, 69.90, 70.05, 70.13, 70.20, 70.23, 70.27, 70.93, 71.64, 74.94, 75.18, 75.33, 76.07, 79.31, 80.95, 82.10, 83.43, 84, 49, 119.83, 123.74, 127.58, 128.06, 128.30, 129.76, 130.02, 131.07, 132.79, 133.19, 133.45, 137.32, 141.18, 156.11, 164.68, 166.24, 168.94, 170.08, 170.97, 173.71, 174.01, 174.74, 203.78; $^{19}$F NMR (282 MHz, $CD_3OD$) δ −46.92 (m, 1F); HRMS (TOF) for $C_{92}H_{132}N_{14}O_{25}FS_3^+$ calcd: 1947.8629. Found: 1947.8647 (Δ=0.9 ppm). HPLC (A): t=6.3 min, purity >98%.

FITC-NH-PEG$_3$-(CH$_2$)$_2$—N$_3$ (11) To a solution of fluorescein isothiocyanate (FITC) (0.200 g, 0.514 mmol) and H$_2$N-PEG$_3$-(CH$_2$)$_2$—N$_3$ (0.131 g, 0.616 mmol) in DMSO (1 mL) was added triethylamine (75 μL, 0.514 mmol), and the mixture was stirred for 2 h at room temperature in the dark. The reaction mixture was concentrated in vacuo to afford a red oil. Purification of the crude product by column chromatography on silica gel with 7% CH$_3$OH in CH$_2$Cl$_2$ as eluent gave azide 5 (0.241 g, 79%) as an orange solid: $^1$H NMR (500 MHz, DMSO-d$_6$) δ 3.42 (t, J=5.0 Hz, 2H), 3.62 (m, 14H), 3.73 (bs, 2H), 6.57 (dd, J=2.3, 8.7 Hz, 2H), 6.62 (d, J=8.7 Hz, 2H), 6.71 (d, J=2.3 Hz, 2H), 7.22 (d, J=8.3 Hz, 1H), 7.78 (d, J=7.8 Hz, 1H), 8.13 (bs, 1H), 8.31 (s, 1H); $^{13}$C NMR (125 MHz, DMSO-d$_6$) δ 44.19, 50.46, 68.90, 69.72, 70.15, 70.28, 79.65, 102.70, 110.18, 113.04, 116.79, 124.54, 127.30, 129.50, 129.86, 141.79, 147.61, 151.34, 159.94, 168.98, 180.99; HRMS (TOF) for $C_{29}H_{30}N_5O_8S^+$ calcd: 608.1810. Found: 608.1822 (Δ=2.0 ppm).

Fluorescent Theranostic Conjugate 2. To a solution of 7 (29.0 mg, 0.0167 mmol) and ascorbic acid (3.3 mg, 0.0185 mmol) in THF (0.5 mL) was added azide 5 (10.2 mg, 0.0167 mmol) first, followed by an aqueous solution of CuSO$_4$.5H$_2$O (4.6 mg, 0.0185 mmol) in H$_2$O (0.1 mL). The mixture was allowed to react at room temperature for 24 h in the dark. The reaction mixture was diluted with H$_2$O (10 mL) and extracted with CH$_2$Cl$_2$ (10 mL×3). The combined organic layers were dried over MgSO$_4$ and concentrated in vacuo to afford a yellow solid, which was re-dissolved in CH$_2$Cl$_2$ and CH$_3$OH (9:1) and lyophilized afford 2 (0.0331 g, 85%) as a yellow solid: $^1$H NMR (500 MHz, DMSO-d$_6$) δ 0.92 (m, 2H), 1.00 (m, 2H), 1.10 (s, 3H), 1.22 (d, J=6.8 Hz, 3H), 1.27 (s, 3H), 1.32 (m, 2H), 1.42 (s, 9H), 1.52 (m, 4H), 1.55 (s, 3H), 1.63 (s, 3H), 1.69 (m, 2H), 1.74 (s, 3H), 1.84 (s, 3H), 1.86 (m, 1H), 2.09 (t, J=7.5 Hz, 2H), 2.20 (t, J=7.0 Hz, 1H), 2.25 (m, 1H), 2.36 (s, 3H), 2.60 (d, J=12.5, 1H), 2.86 (dd, J=5.0, 12.5, 1H), 2.95 (m, 1H), 3.12 (m, 1H), 3.22 (m, 4H), 3.29 (m, 2H), 3.41 (t, J=5.5 Hz, 4H), 3.53 (m, 18H), 3.62 (m, 2H), 3.71 (d, J=7.2 Hz, 2H), 3.81 (m, 2H), 4.00 (s, 2H), 4.09 (m, 2H), 4.15 (m, 2H), 4.33 (m, 1H), 4.50 (m, 2H), 4.75 (m, 1H), 4.85 (d, J=7.9 Hz, 1H), 4.96 (m, 3H), 5.20 (m, 1H), 5.52 (d, J=7.2 Hz, 1H), 6.03 (m, 1H), 6.35 (s, 1H), 6.39 (s, 1H), 6.45 (s, 1H), 6.60 (dd, J=2.3, 8.7 Hz, 2H), 6.64 (d, J=8.7 Hz, 2H), 6.71 (d, J=2.3 Hz, 2H), 7.25 (m, 2H) 7.30 (t, J=7.7 Hz, 1H), 7.34 (m, 1H), 7.40 (t, J=7.7 Hz, 1H), 7.57 (t, J=7.7 Hz, 2H), 7.71 (t, J=7.4 Hz, 1H), 7.76 (bs, 1H), 7.78 (d, J=8.0 Hz, 1H), 7.85 (m, 1H), 7.90 (bs, 1H), 8.04 (d, J=7.6 Hz, 2H), 8.22 (bs, 1H); $^{13}$C NMR (125 MHz, DMSO-d$_6$) δ 8.75, 8.83, 10.24, 13.15, 14.20, 14.23, 18.36, 19.64, 20.45, 20.52, 21.90, 22.99, 25.74, 25.95, 26.81, 28.50, 28.65, 31.57, 32.42, 32.98, 33.07, 35.56, 37.03, 38.31, 38.91, 40.91, 43.49, 46.04, 46.15, 46.69, 49.75, 55.39, 55.91, 57.96, 59.66, 61.50, 69.63, 70.02, 70.11, 70.19, 70.22, 70.89, 73.74, 75.00, 75.03, 75.06, 75.10, 75.12, 75.15, 75.27, 75.78, 77.22, 78.61, 80.88, 83.48, 84.07, 88.37, 102.71, 110.13, 110.45, 113.04, 120.71, 127.89, 128.83, 129.11, 129.50, 129.99, 130.40, 131.63, 133.32, 133.81, 133.87, 133.88, 136.45, 137.33, 137.35, 139.99, 152.37, 155.41, 159.94, 163.18, 165.50, 169.25, 170.07, 170.65, 171.92, 172.60, 172.64, 203.02; HRMS (TOF) calcd for $C_{113}H_{145}N_{16}O_{30}S_4^+$ calcd: 2333.9190. Found: 2333.9130 (Δ=−2.6 ppm). HPLC (B): RT=5.3 min, purity >96%.

Biotin-(SS-Linker)-SB-T-1214 (15). A solution of SB-T-1214-(SS-linker)-OSu (0.069 g, 0.269 mmol) and biotinyl-hydrazine (0.336 g, 0.269 mmol) in a 3:1 mixture of DMSO-pyridine (2.7 mL) was cooled to 0° C., and the mixture was reacted for 4 d at room temperature. Purification of the crude product by column chromatography on silica gel with 7% CH$_3$OH in CH$_2$Cl$_2$ as eluent gave 15 (0.175 g, 47%) as a white solid: $^1$H NMR (400 MHz, CD$_3$OD) δ 1.02 (m, 2H), 1.10 (m, 2H), 1.20 (s, 6H), 1.30 (d, J=6.8 Hz, 3H), 1.44 (s, 9H), 1.49 (m, 2H), 1.63 (m, 4H), 1.68 (s, 3H), 1.76 (s, 3H), 1.78 (s, 3H), 1.81 (m, 3H), 1.94 (s, 3H), 1.99 (m, 2H), 2.28 (t, J=7.6 Hz, 2H), 2.35 (m, 2H), 2.41 (s, 3H), 2.48 (m, 2H), 2.71 (d, J=12.7 Hz, 1H), 2.93 (dd, J=5.0, 12.7 Hz, 1H), 2.98 (m, 1H), 3.22 (m, 1H), 3.87 (d, J=7.2 Hz, 1H), 4.03 (d, J=2.4, 16.7, 1H), 4.13 (d, J=1.8, 16.7 Hz, 1H), 4.20 (d, J=8.4 Hz, 1H), 4.24 (d, J=8.4 Hz, 1H), 4.32 (m, 2H), 4.50 (dd, J=4.4, 8.0 Hz, 1H), 4.59 (s, 2H), 4.94 (d, J=2.4 Hz, 2H), 5.03 (d, J=7.6 Hz, 1H), 5.28 (bs, 1H), 5.69 (d, J=7.2 Hz, 1H), 6.16 (bt, J=9.0 Hz, 1H), 6.48 (s, 1H), 7.33 (m, 3H), 7.53 (t, J=8.0 Hz, 2 Hz), 7.66 (t, J=7.4 Hz, 1H), 7.83 (d, J=7.8 Hz, 1H), 8.15 (d, J=7.2 Hz, 2H); $^{13}$C NMR (125 MHz, CD$_3$OD) δ 7.81, 7.84, 9.06, 12.41, 13.64, 17.27, 19.46, 19.57, 20.99, 21.89, 24.73, 24.98, 25.59, 27.41, 27.96, 28.14, 30.61, 30.90, 32.98, 35.35, 36.14, 38.13, 39.03, 39.67, 43.20, 45.78, 45.90, 46.68, 49.32, 55.54, 57.88, 60.25, 61.85, 70.92, 71.58, 74.92, 75.18, 75.34, 76.06, 77.70, 79.11, 80.93, 84.49, 119.83, 127.51, 128.06, 128.30, 129.75, 130.01, 130.09, 130.12, 131.01, 133.19, 133.37, 133.53, 137.28, 137.40, 137.54, 141.24, 156.09, 164.75, 166.20, 168.91, 170.08, 170.10, 170.89, 172.67, 173.47, 173.72, 203.76; HRMS (TOF) for $C_{68}H_{90}N_5O_{19}S_3^+$ calcd: 1376.5387. Found: 1376.5397 (Δ=0.7 ppm). HPLC (A): RT=12.1 min, purity >99%.

Biological Testing

Two of the drug molecules described hereinabove were tested for their efficacy.

Cell Culture. All cell lines were obtained from ATCC unless otherwise noted. Cells were cultured in RPMI-1640 cell culture medium (Gibco) or DMEM (Gibco), both supplemented with 5% (v/v) heat-inactivated fetal bovine serum (FBS), 5% (v/v) NuSerum, and 1% (v/v) penicillin and streptomycin (PenStrep) at 37° C. in a humidified atmosphere with 5% CO$_2$. MX-1 and ID8 (obtained from University of Kansas Medical Center) cells were cultured as monolayers on 100 mm tissue culture dishes in supplemented RPMI-1640. L1210 and L1210FR (a gift from Dr. Gregory Russell-Jones, Access Pharmaceuticals Pty Ltd., Australia) were grown as a suspension in supplemented RPMI-1640, and WI-38 as a monolayer in supplemented DMEM. Cells were harvested, collected by centrifugation at 850 rpm for 5 min, and resuspended in fresh culture medium. Cell cultures were routinely divided by treatment with trypsin (TrypLE, Gibco) as needed every 2-4 days and collected by centrifugation at 850 rpm for 5 min, and resuspended in fresh cell culture medium, containing varying cell densities for subsequent biological experiments and analysis.

Incubation of Cells with Fluorescent Probes 2 and 16. Cell suspensions (3 mL) at 5×10$^5$ cells/mL were added to each individual well of 6-well plates, and subsequently incubated overnight in the appropriate cell culture media. The cell culture media was replaced with 5 μM solutions of 2 and 16 in cell culture media (3 mL). The cells were then incubated with the probes for various time intervals ranging from 30 min to 24 h at 37° C. In the case of leukemia cell lines (L1210, L1210FR), each probe (1 mM) in DMSO (15 μM) was injected directly into fresh cell suspensions to give a final concentration of 5 μM, and incubated for similar time intervals. After incubation, the cells were removed by treating with trypsin (as needed), washed twice with PBS, collected by centrifugation, and resuspended in PBS (150 µL) for CFM and flow cytometry analysis.

Flow Cytometry Analysis of the Treated Cells. Flow cytometry analysis of the cells treated with probes 2 and 16 was performed with a flow cytometer, FACS Calibur, operating at a 488 nm excitation wavelength and detecting 530 nm emission wavelengths with a 30 nm bandpass filter (515-545 nm range). Cells treated as described above were resuspended in 0.5 mL of PBS. Approximately 10,000 cells were counted for each experiment using CellQuest 3.3 software (Becton Dickinson), and the distribution of FITC fluorescence was analyzed using WinMDI 2.8 freeware (Joseph Trotter, Scripps Research Institute).

Confocal Fluorescence Microscopy Imaging of the Treated Cells. Cells treated as described above were resuspended in 150 µL of PBS after each experiment, and dropped onto an uncoated microslide with coverslip (MatTek Corp). Confocal fluorescence microscopy (CFM) experiments were performed using a Zeiss LSM 510 META NLO two-photon laser scanning confocal microscope system, operating at a 488 nm excitation wavelength and at 527±23 nm detecting emission wavelength using a 505-550 nm bandpass filter. Images for 2 and 16 were captured using a C-Apochromat 63×/1.2 water (corr.) objective. Acquired data were analyzed using LSM 510 Meta software.

In Vitro Cytotoxicity Assays. The cytotoxicities ($IC_{50}$, nM) of paclitaxel, taxoid 3, and conjugates 1 and 15 were evaluated against various cancer cell lines by means of the standard quantitative colorimetric MTT assay.[39] The inhibitory activity of each compound is represented by the $IC_{50}$ value, which is defined as the concentration required for inhibiting 50% of the cell growth. Cells were harvested, collected, and resuspended in 100 µL cell culture medium at concentrations ranging from 0.5-1.5×10⁴ cells per well in a 96-well plate. For adhesive cell types, cells were allowed to descend to the bottom of the wells overnight, and fresh medium was added to each well upon removal of the old medium.

For the MTT assay (Table 1 and the Assay 1 in Table 2) of paclitaxel, taxoid 3 and conjugates 1 and 15, cells were resuspended in 200 µL medium with 8,000 to 10,000 cells per well of a 96-well plate and incubated at 37° C. for 24 h before drug treatment. In DMSO stock solutions, each drug or conjugate was diluted to a series of concentrations in cell culture medium to prepare test solutions. After removing the old medium, these test solutions were added to the wells in the 96-well plate to give the final concentrations ranging from 0.5 to 5,000 nM (100 µL), and the cells were subsequently cultured at 37° C. for 48 h (Table 1) or 72 h (Table 2, Assay 1). For the leukemia cell lines, L1210 and L1210FR, cells were harvested, collected, and resuspended in the test solutions ranging from 0.5 to 5,000 nM (100 µL) at 0.5 to 0.8 ×10⁴ cells per well in a 96-well plate and subsequently incubated at 37° C. for 48 h (Table 1) or 72 h (Table 2, Assay 1).

In the Assay 2 (Table 2), cells were incubated with 1 or 15 at 37° C. for 24 h, and the drug medium was removed. Then, treated cells were thoroughly washed with PBS, and GSH-OEt (6 equiv. to conjugate) in cell culture medium (200 µL) was added to the wells. These cells were incubated at 37° C. for an additional 48 h, i.e., the total incubation time was 72 h.

In the Assay 3 (Table 2), cells were incubated with 1 or 15 at 37° C. for 24 h, and GSH-OEt (6 equivalents) in cell culture medium (100 µL) was directly added to the wells. These cells were incubated at 37° C. for an additional 48 h, i.e. the total incubation time was also 72 h.

For all experiments, after removing the test medium, fresh solution of MTT in PBS (40 µL of 0.5 mg MTT/mL) was added to the wells, and the cells were incubated at 37° C. for 3 h. The MTT solution was then removed, and the resulting insoluble violet formazan crystals were dissolved in 0.1 N HCl in isopropanol with 10% Triton X-100 (40 µL) to give a violet solution. The spectrophotometric absorbance measurement of each well in the 96-well plate was run at 570 nm using a Labsystems Multiskan Ascent microplate reader. The $IC_{50}$ values and their standard errors were calculated from the viability-concentration curve using Four Parameter Logistic Model of Sigmaplot. The concentration of DMSO per well was ≤1% in all cases. Each experiment was run in triplicate.

Biological Evaluation of Theranostic Conjugates 1 and 2
Internalization of Fluorescent Conjugate 2 and Probe 16 by Confocal Fluorescence Microscopy (CFM) and Flow Cytometry. Probe 16 serves as an excellent reference to examine the efficiency of the internalization of theranostic conjugate 2 into BR+ cancer cells via RME and to assess a possible effect of molecular size on the efficiency. In addition, fluorescence-labeled paclitaxel was employed to assess the non-specific internalization of paclitaxel into BR+ and BR− cells, including a human normal cell line. Thus, the internalization study on these three probes should give us a fair and accurate assessment of the cancer cell targeting specificity of theranostic conjugate 2.

Figure 4:
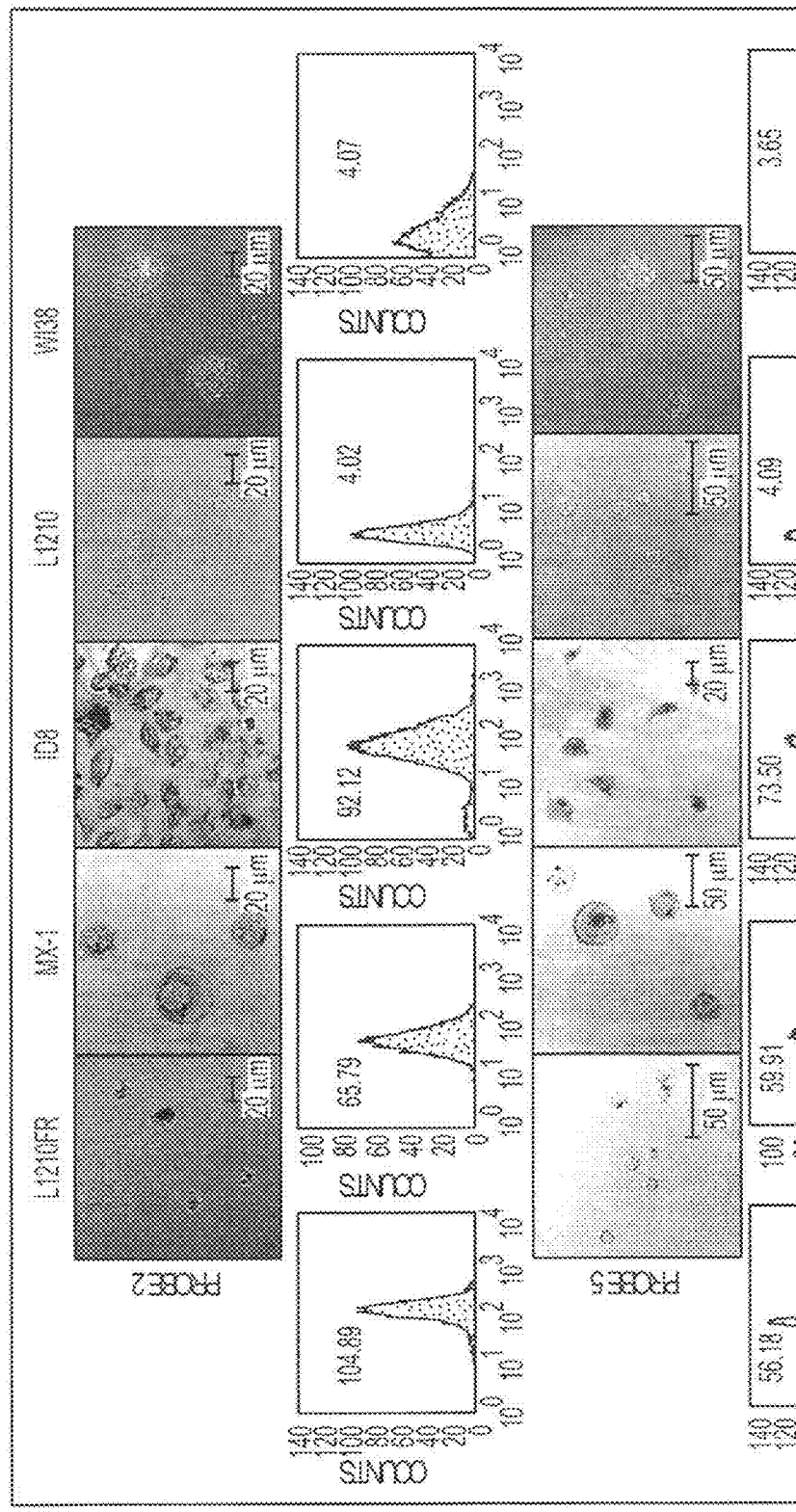
FIG. 4 shows CFM images and flow cytometry analysis of L1210FR (BR+), MX-1 (BR+), ID8 (BR+), L1210 (BR−), and WI38 (BR−) cell lines after incubation with theranostic conjugate 2 (5 μM) (upper row) or probe 16 (5 μM) (lower row) at 37° C. for 3 hours.
Figure 5:
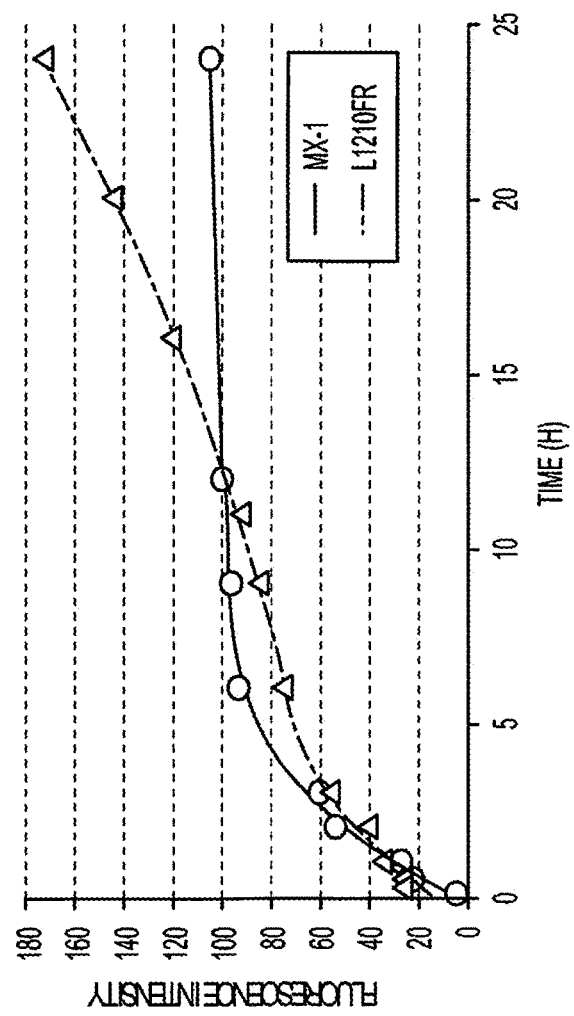
FIG. 5 shows time-course of the internalization of theranostic conjugate 2 (5 μM) in L1210FR (BR+, solid triangle) and MX-1 (BR+, solid circle) cells at 37° C. by flow cytometry analysis.

Internalization of probes 2 and 16 was visualized by CFM, and the fluorescence intensity was quantified using flow cytometry. Cellular uptake of two probes 2 and 16 across three BR+ cancer cell lines, L1210FR (murine leukemia), MX-1 (human breast) and ID8 (murine ovary), as well as BR− cell lines, L1210 (murine leukemia) and WI38 (human lung fibroblast), is summarized in FIG. 4. As FIG. 4 shows, the extent of internalization of theranostic conjugate 2 is comparable to that of probe 5. Nevertheless, there is a consistent trend that smaller probe 16 shows appreciably higher fluorescence intensity. Thus, there is some effect of molecular size on the internalization via RME, although there is no practical issue associated. There was no appreciable internalization of 2 and 16 into BR− cell lines, L1210 and WI38 (FIG. 4), indicating excellent BR+ specificity of these probes. In sharp contrast, fluorescence-labeled paclitaxel clearly exhibited non-specific internalization across both BR+ and BR− cell lines (data not shown). Consequently, the highly target-specific and efficient internalization of 2 and 16 into BR+ cancer cell lines has been confirmed.

Biological Evaluation of Theranostic Conjugate 1. The cytotoxicities of 1 and 15 were evaluated in four sets of assays against three BR+ cancer cell lines, L1210FR, MX-1, and ID8, and two BR− cell lines, L1210 and WI38, using the standard MTT assay.[39] Results are summarized in Tables 1 and 2. Potency of paclitaxel and taxoid 3 on these cell lines were also examined for comparison purpose.

First, L1210FR, MX-1, and ID8 (BR⁺) cancer cell lines were incubated with conjugates 1 and 15 for 48 h, and the corresponding $IC_{50}$ values were determined. As Table 1 shows, the cytotoxicity ($IC_{50}$) of 1 was in a range of 6-21 nM (entry 3). In sharp contrast, its cytotoxicity against normal cell line WI38 ($IC_{50}$ 709 nM), as well as BR− leukemia cell line L1210 ($IC_{50}$ 593 nM) was one-two orders of magnitude weaker in potency. The results clearly indicate that conjugate 1 was selectively internalized into BR+ cancer cells via RME and released the cytotoxic warhead, taxoid 3. On the other hand, paclitaxel and taxoid 3 were practically non-selective against BR⁺ and BR⁻ cell lines, although MX-1 and ID8 cell lines appeared to be more sensitive to these two drugs (entries 1 and 2). Smaller conjugate 15 exhibited similar results to those for conjugate 1, but with somewhat higher potency against all cell lines used (entry 4). The results for conjugates 1 and 15 also indicate that their observed potency was 3-30 times lower than the free warhead, i.e., taxoid 3, against three BR+ cancer cell lines. This implies that not all warheads were released after the internalization of conjugates into these cancer cells. Without wishing to be bound, it is believed that this result is probably due to the lack of sufficient endogenous thiols such as glutathione (GSH) under in vitro assay conditions. Also, 48 h incubation time might be insufficient for drug release.

smaller, indicating that an additional 24 h incubation increased the cytotoxic effect of conjugates (entries 3 and 4). However, only a slight increase in the cytotoxic effect was observed for L1210FR cell line. Also, there was practically no difference in their cytotoxic effect against WI38 cell line (entries 3 and 4). Paclitaxel and taxoid 3 showed a slight increase in potency in this 72-h assay (entries 1 and 2), as compared to that in the 48-h assay (Table 1).

As the Assay 2 columns for MX-1 and L1210FR cell lines show, there were clear increases in potency, especially against the L1210FR cell line. The results represent the level of internalization of conjugates at the 24 h period, which show that the intracellular concentration of the released

TABLE 1

Cytotoxicities ($IC_{50}$, nM) of Paclitaxel, Taxoid 3, Conjugates 1 and 15 against BR+ and BR− Cell Lines (Incubation at 37° C. for 48 h)

| Entry | Compound | MX-1[a] | ID8[b] | L1210FR[c] | L1210[d] | WI38[e] |
|---|---|---|---|---|---|---|
| 1[f] | paclitaxel | 7.23 ± 0.68 | 14.36 ± 1.81 | 38.7 ± 17.7 | 77.1 ± 12.8 | 61.4 ± 12.7 |
| 2[f] | Taxoid 3 | 4.13 ± 2.59 | 0.17 ± 0.14 | 4.18 ± 1.8 | 7.05 ± 1.38 | 5.23 ± 0.27 |
| 3[f] | 1 | 21.2 ± 4.6 | 6.62 ± 0.86 | 14.7 ± 4.0 | 593 ± 123 | 709 ± 55 |
| 4[f] | 4 | 15.4 ± 4.2 | 4.32 ± 1.58 | 13.4 ± 6.8 | 481 ± 34 | 670 ± 89 |

[a]human breast carcinoma cell line (BR+);
[b]murine ovarian carcinoma cell line (BR+);
[c]murine lymphocytic leukemia cell line (BR+);
[d]murine lymphocytic leukemia cell line (BR−);
[e]Human lung fibroblast cell line (BR−);
[f]Cells were incubated with a drug or conjugate at 37° C. for 48 h.

Three more sets of assays were performed to assess the extent of the RME of conjugates 1 and 15 as well as that of drug release: (i) In the Assay 1, MX-1, L1210FR and WI38 cells were incubated with conjugates 1 and 15 for 72 h, and their $IC_{50}$ values were determined; (ii) In the Assay 2, (a) the three cell lines were incubated with conjugates 1 and 15 for 24 h, (b) the cell culture medium was removed by thorough washing of the cells with PBS, (c) cells were resuspended and glutathione ethyl ester (GSH-OEt) (6 equivalents to conjugate) was added, and (d) the cells were incubated for additional 48 h (i.e., total incubation time was 72 h); (iii) In the Assay 3, (a) the three cells were incubated with conjugates 1 and 15 for 24 h, (b) GSH-OEt (6 equivalents to conjugate) was added to the medium, and (c) the cells were incubated for additional 48 h (total incubation time was 72 h). Thus, the Assay 1 results provide the potency of conjugates in the same manner as that for the first assay summarized in Table 1, but for longer incubation time (48 h vs. 72 h). The Assay 2 results indicate the extent of the internalization of conjugates in the first 24 h period with sufficient drug release inside cells, i.e., only conjugate molecules internalized into cells exert cytotoxic effect through drug release. Accordingly, this assay may mimic the corresponding in vivo assay conditions, wherein non-internalized conjugates would be removed from the tumor, redistributed and eventually excreted. The Assay 3 results exhibit the mass balance of conjugates inside as well as outside of cells, by releasing the cytotoxic warhead in the whole cell culture medium at 24 h period. Thus, in principle, the results ($IC_{50}$ values) in this assay should be very close to those for the control using taxoid 3 (entry 2). Results are summarized in Table 2.

As the Assay 1 columns for MX-1 and L1210FR cell lines show, the $IC_{50}$ values against MX-1 cell lines are ca. 3 times warhead did not reach that of free taxoid 3 given externally. Nevertheless, the cancer cell selectivity (BR-specificity) of conjugates 1 and 15 is quite impressive, i.e., two-orders of magnitude difference between BR+\cancer cells and BR−\WI38 cells. The results also indicate that there is no practical difference in potency between conjugate 1 and smaller-conjugate 15. Thus, the theranostic conjugate 1 (with $^{18}F$) exhibits the same level of efficacy as that for smaller-conjugate 15 in animal tumor models in vivo. The cytotoxicity against WI38 was unchanged within experimental error from that observed in the Assay 1, which means that essentially no internalization of conjugates into WI38 cells occurred in both cases.

The Assay 3 results against MX-1 and L1210FR cell lines exhibited the same level of potency as that for free taxoid 3, as anticipated. The results clearly indicate that some of each conjugate was not internalized into cancer cells. The non-internalized conjugates released free taxoid 3 in the cell culture medium upon addition of GSH-OEt, and the released taxoid 3 diffused into the cancer cell to exert its cytotoxic effect. The results proved that the mass balance in these assays are excellent and thus these assay results are valid. Interestingly, there was a 2~3-fold difference in the potency of conjugates against WI38, for some reason, which needs further investigation.

Without wishing to be bound, it is believed that that non-internalized conjugates are removed from tumor tissues and eventually excreted. Thus, the putative systemic toxicity of conjugates is believed to be represented by the results in Assays 1 and 2, i.e., conjugates are essentially benign against normal cells (BR) at the drug concentration to be used for chemotherapy.

TABLE 2

Cytotoxicities (IC$_{50}$, nM) of Paclitaxel, Taxoid 3, Conjugate 1 and Conjugate 15 in the Absence and Presence of GSH-OEt

| | | MX-1[a] | | | L1210FR[c] | | | WI38[e] | | |
|---|---|---|---|---|---|---|---|---|---|---|
| Entry | Compound | Assay 1[b] | Assay 2[d] | Assay 3[f] | Assay 1[b] | Assay 2[d] | Assay 3[f] | Assay 1[b] | Assay 2[d] | Assay 3[f] |
| 1 | paclitaxel | 4.07 ± 0.80 | | | 35.6 ± 8.2 | | | 55.7 ± 9.54 | | |
| 2 | taxoid 3 | 2.66 ± 0.16 | | | 2.32 ± 1.41 | | | 4.89 ± 2.24 | | |
| 3 | 1 | 6.27 ± 2.06 | 4.79 ± 0.12 | 2.56 ± 0.15 | 10.2 ± 3.0 | 6.60 ± 3.96 | 2.79 ± 1.43 | 682 ± 110 | 615 ± 97 | 12.9 ± 4.3 |
| 4 | 4 | 4.66 ± 0.87 | 3.85 ± 0.14 | 2.40 ± 0.18 | 12.3 ± 2.8 | 5.15 ± 2.85 | 2.92 ± 2.34 | 645 ± 97 | 590 ± 164 | 11.0 ± 3.1 |

[a,c,e] See captions for cell lines in Table 1;
[b] Cells were incubated with a drug or conjugate at 37° C. in a 5% CO$_2$ atmosphere for 72 h;
[d] Cells were initially incubated with 1 or 4 at 37° C. in a 5% CO$_2$ atmosphere for 24 h, followed by washing of the drug media with PBS, then addition of GSH-OEt (6 equiv. to conjugate) for drug release and additional incubation for 48 h;
[f] Cells were initially incubated with 1 or 4 at 37° C. in a 5% CO$_2$ atmosphere for 24 h, followed by addition of GSH-OEt (6 equiv. to conjugate) for drug release and additional incubation for 48 h. Total drug or conjugate incubation was 72 h for all experiments.

Other biological results showing efficacy of the compounds of the present disclosure are provided in FIGS. 1, 2, 3 and 5.

Thus, novel tumor-targeting therapeutic conjugates of Formula I and II, such as 1 and 2, which consist of biotin as the tumor-targeting module, taxoid 3 as the cytotoxic agent, a self-immolative disulfide linker for drug release, 1,3,5-triazine as the splitter module, ethylene glycol oligomers to increase aqueous solubility, and an imaging modality, such as either a fluorine-labeled prosthetic in 1 for potential $^{18}$F-PET imaging in vivo or an FITC tether in 2 for internalization and drug-release studies in vitro have been synthesized. The multi-functionalized 1,3,5-triazine-based TTDDS platform is highly versatile and applicable to a variety of imaging modalities, such as those for PET, SPECT or MRI. Rapid late-stage introduction of a fluorine prosthetic by "click" chemistry is readily applicable to multistep synthesis of $^{18}$F-labeled tumor-targeting drug conjugates.

There was efficient internalization of conjugate 2 in BR$^+$ cancer cells via RME based on flow cytometry and CFM analyses. This TTDDS exhibited very high specificity to BR+ cancer cells. Based on the comparison with a small-molecule biotin probe 16 (MW: 808), it was concluded that conjugate 2 (MW: 2,334) was internalized at a very similar level to that of smaller conjugate 16, and thus the size of conjugate 2 imposes little effect on the efficiency of RME.

The potency and selectivity of conjugates 1 and 15 were evaluated against MX-1, L1210FR and ID8 cancer cells (BR+), as well as L1210 and WI38 cells (BR−) in the absence and presence of GSH-OEt. In the absence of GSH-OEt addition, it was found that there was 30-120 times higher selectivity (BR specificity) in three BR+ cancer cell lines for 48 h and 72 h incubation times. However, the potencies of conjugates 1 and 15 were 2-30 times lower than the free taxoid 3 in the same assay, which indicated insufficient drug release by the endogenous GSH in these cells under the in vitro cell culture conditions.

Accordingly, in another assay, the extent of the internalization of conjugates 1 and 15 into MX-1 (BR+), L1210FR (BR+) and WI38 (BR−) cells was examined in the first 24 h period with sufficient drug release inside cells by addition of GSH-OEt, i.e., only conjugate molecules internalized into cells exert cytotoxic effect through drug release with additional 48 h incubation (total 72 h). This assay may mimic the corresponding in vivo assay conditions, wherein non-internalized conjugates would be removed from tumor, redistributed and eventually excreted. In this assay, it was found that the intracellular concentration of the released warhead did not reach that of free taxoid 3 given externally, while the cancer cell selectivity (BR-specificity) of conjugates 1 and 15 was remarkable with two-orders of magnitude difference between BR+ cancer cells (IC$_{50}$ 3.85-6.60 nM) and BR− WI38 cells (IC$_{50}$ 590615 nM). No practical difference in potency between conjugate 1 and conjugate 15 was observed. The cytotoxicity against W138 was unchanged within error from that observed in the first assay, confirming that essentially there was little internalization of conjugates 1 and 15 into WI38 cells in both cases.

In the third assay, which was a control experiment, GSH-OEt was added to the cell culture medium after 24 h incubation without PBS washing, followed by additional 48 h incubation. Thus, this assay against MX-1 and L1210FR cell lines reveals the mass balance of conjugates inside as well as outside of cells. In fact, conjugates 1 and 15 showed exactly the same level of potency (IC$_{50}$ 2.40-2.92 nM) as that for free taxoid 3 (IC$_{50}$ 2.32-2.66 nM). This means that that a certain amount of conjugates, which were not internalized into cancer cells in the 24 h incubation period, existed in the cell culture medium. The results demonstrated an excellent mass balance, confirming the validity of these three assays.

Since non-internalized conjugates would be removed from tumor tissues and eventually excreted in vivo, conjugates 1 and 15 are essentially benign against normal cells (BR−) at the drug concentration to be used for chemotherapy.

II. Another embodiment of the present invention is directed to a theranostic agent of Formula III:

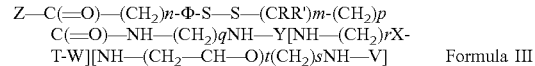

Z—C(=O)—(CH$_2$)n-Φ-S—S—(CRR')m-(CH$_2$)p
C(=O)—NH—(CH$_2$)qNH—Y[NH—(CH$_2$)rX-
T-W][NH—(CH$_2$—CH—O)t(CH$_2$)sNH—V]     Formula III or a pharmaceutically acceptable salt thereof,
wherein,
Z is a taxoid identified by compound 3 wherein the hydroxyl group therein is replaced by O;
Φ is a phenyl ring;
R, R' is hydrogen or alkyl group containing 1 or 2 or 3 carbon atoms;
m and n and p are independently 1. 2, or 3,
Y is a triazine, including a 1,3,5-triazine;
r is 1, 2, or 3;
X is a triazole, including 1,2,3-triazole, to which is optionally fused a cycloalkyl ring containing 5, 6, 7, 8, 9, or 10 carbon ring atoms;
T is O—(CH$_2$)a-C(=O)—;
a is 1, 2, or 3;
W is Q-U;
Q is a radionuclide;
U is an imaging modality;

s is 1-6;

t is 1, 2, 3, 4, 5, or 6; and

V is biotin or folic acid wherein the COOH moiety forms an amide bond with the NH group.

Another aspect of this disclosure is a pharmaceutical composition comprising the theranostic agent of Formula III and a pharmaceutically acceptable carrier therefor.

A further aspect of the present disclosure is directed to a method of treating a tumor in a subject comprising administering to the subject in need thereof a therapeutically effective amount of the theranostic agent of formula III.

A further aspect is directed to a method of diagnosing a tumor in a subject comprising administering to the subject in need thereof a diagnostically effective amount of the theranostic agent of Formula III.

The TDDD of this embodiment consists of various parts. One part is a tumor-targeting module. It is a vitamin. Although vitamins are essential to the cellular growth and survival of all living cells, cancer cells require certain vitamins, such as biotin, more than normal cells to sustain their growth and enhanced proliferation. More specifically, the tumor targeting module is biotin. Receptors for this vitamin are overexpressed on the surface of cancer cells to maintain extensive vitamin uptake.

Another portion of the TDDD is the cytotoxic agent, e.g., a taxoid of formula 3 indicated hereinabove.

Another portion of the TDD is the linker. This linker is a disulfide linker, which is conjugated to a cytotoxic agent on one end and a tumor-targeting module on the other end. These self-immolative linkers are stable during circulation in blood stream, but are readily cleavable in the tumor microenvironment. Once a drug conjugate is internalized into tumor cells following target-specific binding and receptor-mediated endocytosis (RME), the linker releases the drug warhead. Without wishing to be bound, it is believed that the linker is cleaved through thiol-disulfide exchange with endogenous thiols, e.g., glutathione (GSH) and thioredoxin via facile benzothiolactonization. Since the GSH level in tumor tissues (2-8 mM) is more than 1,000 times higher than that in the blood stream (1-2 μM), GSH and other endogenous thiols serve as ideal tumor-specific triggers for drug release. The linker is a moiety of the formula —C(=O)—(CH$_2$)n-Φ-S—S—(CRR')m-(CH$_2$)p-C(=O)—, wherein Φ is a phenyl ring, R, R' is hydrogen or alkyl group containing 1 or 2 or 3 carbon atoms and m and n and p are independently 1. 2, or 3.

In an embodiment, n is 1 or 2 and in another embodiment 1. The acyl moiety C(=O) forms an ester bond with the hydroxyl moiety on compound 3. In another embodiment, m is 1 or 2 and in a further embodiment, m is 1. In another embodiment, p is 1 or 2 and in another embodiment, p is 2. In an embodiment, R is methyl or ethyl, n-propyl or iso-propyl. In a further embodiment, R is methyl or ethyl and a further embodiment, R is methyl. In a further embodiment, n is 1 or 2, m is 1 or 2, p is 1 or 2, and R is methyl. In a further embodiment, R is methyl and m is 1 and n is 1 or 2 and p is 1 or 2. In a further embodiment, the —(CH$_2$)n and the S—S linkage are ortho substituted on the phenyl ring.

Another portion of the therapeutic agent consists of a 1,3,5-triazine splitter module. This 1,3,5-triazine module is linked to the disulfide moiety described hereinabove by an amino alkyl amino linkage, i.e., NH—(CH$_2$)q-NH$_2$, wherein q is 1 to 3 in one embodiment, while in another embodiment, it is 1 or 2, and in another embodiment, it is 2 or 3 and in a further embodiment, it is 2. The splitter which is a 1,3, 5-triazine, is substituted on the 2, 4, and 6 positions of the triazine by three different legs. One leg is described hereinabove which is connected to the disulfide bridge by NH—(CH$_2$)q-NH—, another leg of the triazine molecule connects the imaging module to a triazine moiety described hereinabove through a click linker and the other leg of the triazine is connected through a linker to the biotin moiety.

Another portion of the therapeutic agent consists of an imaging modality. The imaging modality is an imaging moiety for positron emission tomography (PET) or SPEC imaging to track the progress Radioisotopes are used with PET or SPECT imaging to track the progress of the cytotoxic drug conjugate within the body. PET (positron emission tomography) and SPECT (single photon emission computed tomography) both utilize the emission of particles of radioisotopes as they decay. In the case of PET scans, radioisotopes that undergo positron decay are used. When the emitted positron collides with an electron, they annihilate and produce two gamma rays emitted at almost 180 degrees apart from each other. Therefore it is possible to localize the annihilation along a line of coincidence, or line of response (LOR), producing a three-dimensional image. SPECT detects a single gamma photon emitted by a radioisotope, so the radioactive material must undergo gamma decay. This also produces three-dimensional information about the presence of the radioisotope, and thus the drug conjugate as well. To acquire SPECT images, the gamma camera is rotated around the patient. Projections are acquired at defined points, typically every 4 or 5 degrees. A 360-degree rotation is used to obtain an optimal reconstruction. The gamma camera acquires multiple 2-D images from multiple angles. Then, using a tomographic reconstruction algorithm, it is able yield a 3-D view of the distribution of the radionuclide. Tomographic reconstruction makes use of attenuation, which is the gradual loss in intensity of any kind of flux in a medium.

This imaging modality is located on one of the legs of the triazine splitter moiety described hereinabove through a click linker and ethylene glycol oligomers. An example of the radioactive nuclide useful for PET is $^{18}$F, $^{64}$Cu, $^{68}$Ga and the like. For longer duration and less expensive imaging, the use of Tc-99m with a SPECT scanner is common and effective. The technetium radioisotope is relatively easy to produce and it has a longer half-life (6.0058 hours). The ideal would be to rely on PET scans, which are more accurate, but also use a tracer that has a longer half-life. Cu-64 has a half-life of 12.701 hours and decays by positron emission, giving it the proper requirements for a PET scan. This allows for accurate imaging of both smaller molecules and larger, slower clearing proteins and nanoparticles.

The theranostic agent contains the radioactive nuclide, which is linked to the click linker by T, which is O—(CH$_2$)a-C(=O)p. In an embodiment, a is 1 or 2 and in another embodiment, a is 1.

The imaging agent is an imaging agent that is normally used in this art. Examples include the imaging agents depicted hereinbelow.

Another leg of the triazine is connected to the biotin V through NH—(CH$_2$—CH—O)t-(CH$_2$)s-NHC(=O)—(CH$_2$)uV, wherein s is 1-6, and t and u are independently 1,2, 3 or 4. In an embodiment, t is 2, 3, or 4, and in another embodiment, t is 2 or 3, and in another embodiment, t is 3. In an embodiment, s is 3-6, and in another embodiment, s is 4 or 5 and in another embodiment, s is 4. In an embodiment, u is 1 or 2 and in another embodiment, u is 1.

An embodiment of Formula III is depicted hereinbelow:

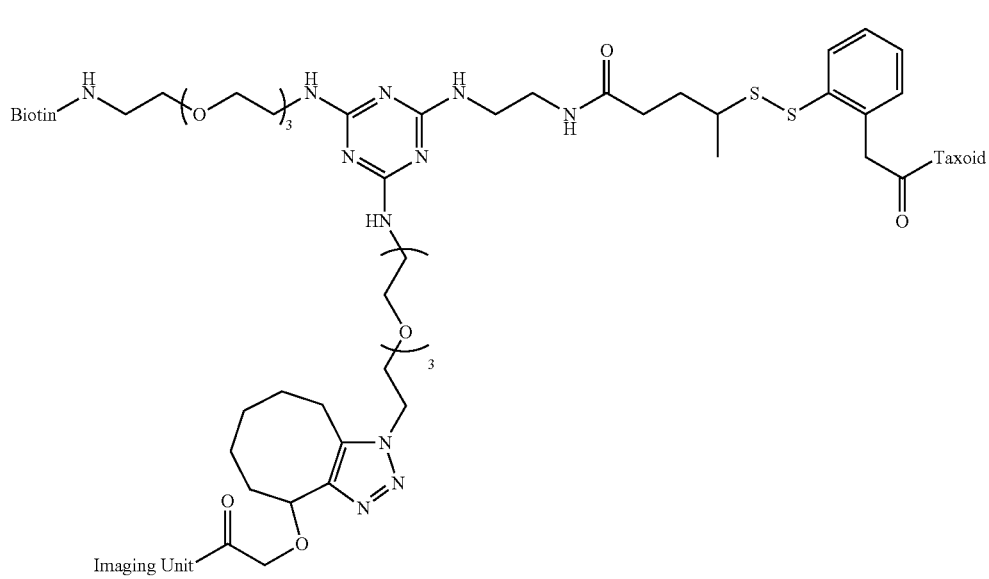

Compound 100

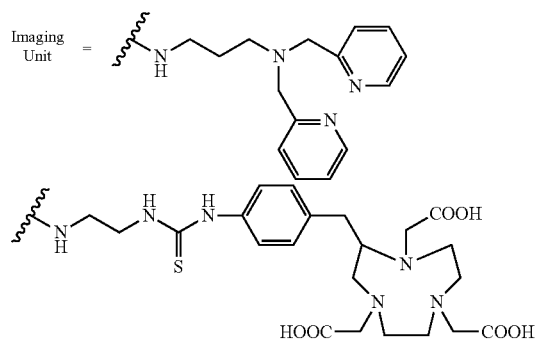

or Imaging Unit = $^{99m}$Tc or $^{64}$Cu

The following is exemplary for preparing the compounds of Formula III.

Cyanuric chloride as triazine splitter core was selected to afford three arms for different functionalities including a biotin molecule as tumor-targeting moiety, an anti-cancer drug molecule (e.g., taxoid 3) with a self-immolative disulfide linker, and an imaging arm for chelation with radiotracer. To increase the water solubility, a polyethylene glycol trimer in the biotin arm and the imaging arm. As discussed above, $^{99m}$Tc and $^{64}$Cu were selected as radioactive tracers for SPECT and PET imaging studies, respectively. Therefore, $^{186}$Re and $^{65}$Cu were investigated as surrogates for the two chelating arms bearing a di-picolylamine (DPA) moiety and a 1,4,7-triazacyclononane-N,N', N"-triacetic acid (NOTA) moiety for capturing $^{186}$Re and $^{65}$Cu, respectively. To efficiently and orthogonally install the ligand to the whole conjugate, click chemistry was used to introduce the third arm bearing the chelating ligands in the presence of biotin and linker-drug arms. A click condition SPAAC (Strain-Promoted Alkyne-Azide Cycloaddition) was used to avoid the usage of copper catalyst.

Three different arms in sequence were installed by controlling the reaction temperature based on its temperature-related reactivity (Scheme 1'). The first arm was installed on the cyanuric chloride in the presence of DIPEA as base using 11-azido-3,6,9-trioxaundecan-1-amine (1'), which is commercially available or can be readily prepared.[5,6] This step was run under 0° C. for 3 hours, followed by the addition of the biotin-PEG$_3$-(CH$_2$)$_2$—NH$_2$ (2') as the second arm under room temperature. Compound 2' was readily prepared from biotin and commercially available 11-azido-3,6,9 trioxaundecan-1-amine 1' through amide coupling, followed by Staudinger reduction of the resulting azide. The monochloro intermediate 3' was isolated in moderate yield. Then the third arm was installed using mono-Boc protected ethylene 1,4-diamine 4' under reflux condition to give intermediate 5'. Then, the Boc protecting group was removed by using trifluoroacetic acid to generate 6', followed by treating with N,N-diisopropylethylamine to generate primary amine in situ. The primary amine was used to react with taxoid-linker-activated OSu ester 7' to form the click-ready biotin-triazine-linker-drug intermediate 8' (Scheme 1').

Scheme 1'
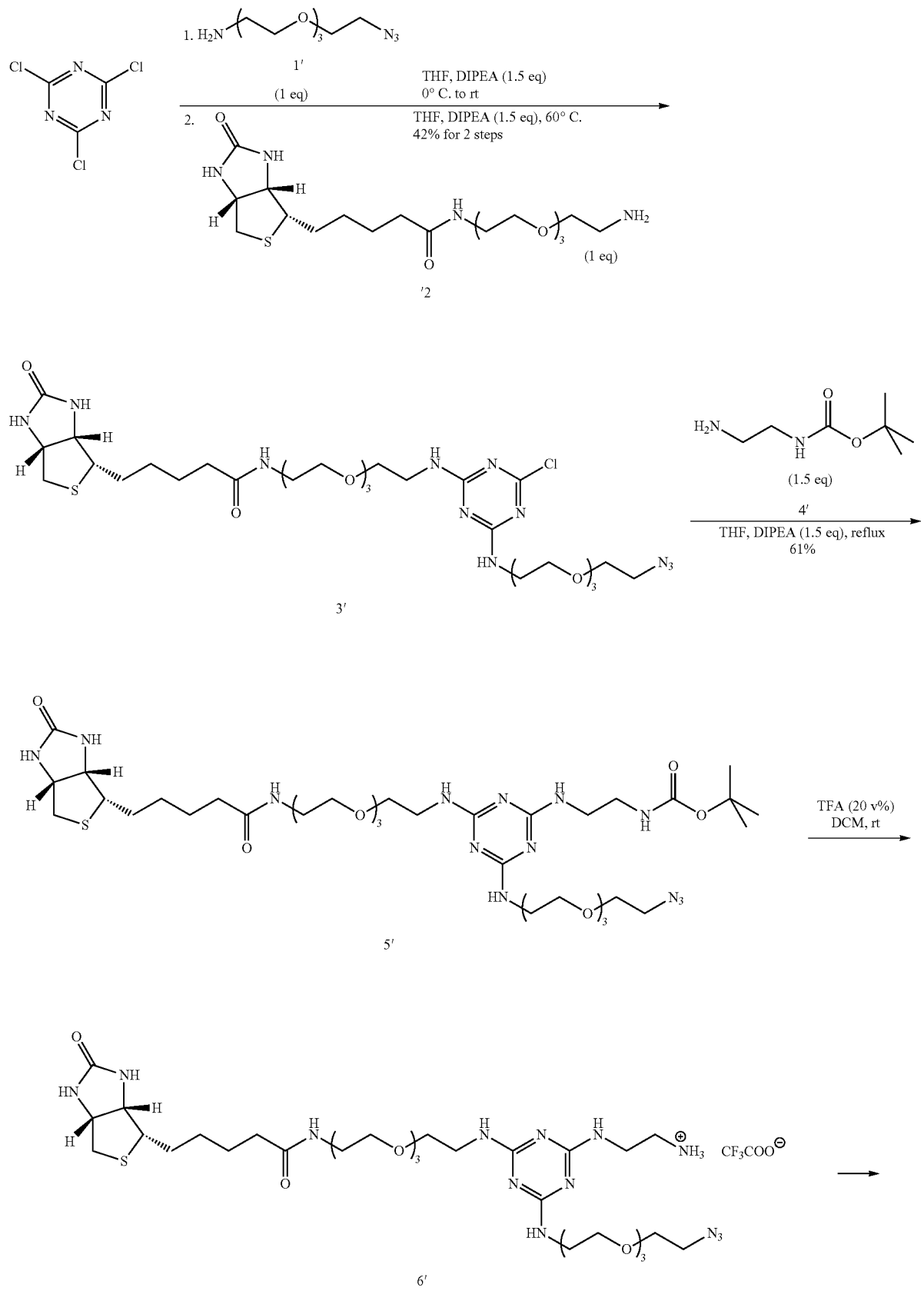

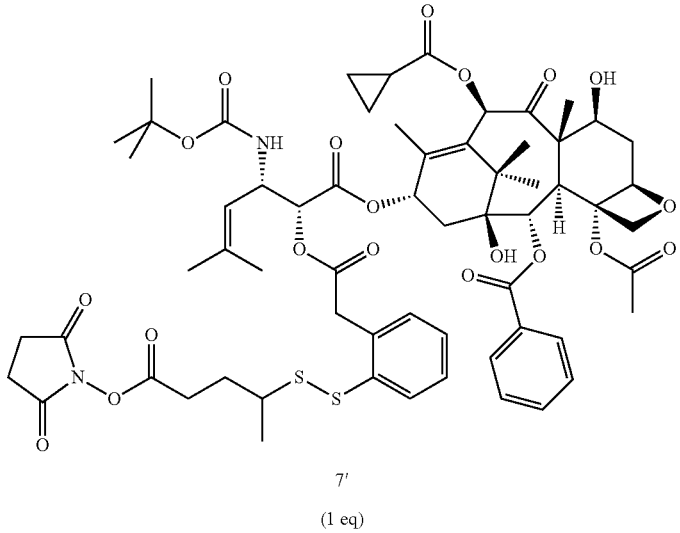

7'
(1 eq)

DIPEA (1.5 eq), DCM, rt
65% for 2 steps

8'

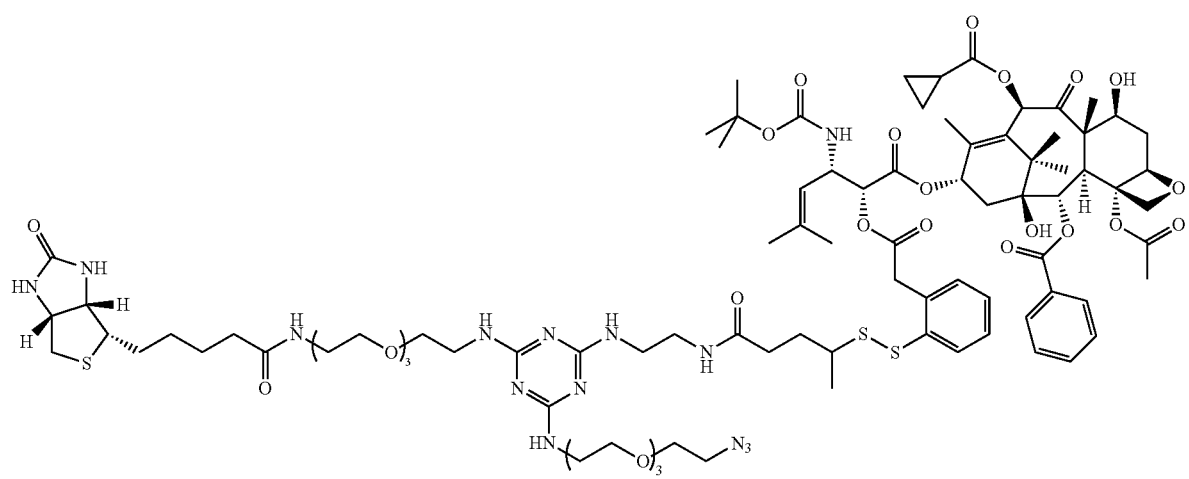

The cyclooctyne moiety was synthesized starting from the cycloheptene through a carbene reaction to obtain the dibromobicicyclo intermediate 9', followed by the ring expansion and formation of vinyl bromo intermediate 10' in the presence of silver perchlorate, and elimination to generate cyclooctyne-acid 11' by using sodium methoxide (Scheme 2'). The cyclooctyne-DPA trident chelating ligand 15' was synthesized according to the reported procedures in Yamanaka, S.; Ōkawa, H.; Motoda, K.-i.; Yonemura, M.; Fenton, D. E.; Ebadi, M.; Lever, A. B. P. Tetracopper Assembly Complexes Comprised of One Dimetallic Core and Two Monometallic Auxiliaries: Intramolecular Electron-Transfer Relevant to Multicopper Oxidases. *Inorganic Chemistry* 1999, 38, 1825-1830, and Pimentel, L. C. F.; de Souza, A. L. F.; Fernández, T. L.; Wardell, J. L.; Antunes, 0. A. C. Microwave-assisted synthesis of N,N-bis-(2-pyridylmethyl)amine derivatives. Useful ligands in coordination chemistry, *Tetrahedron Letters* 2007, 48, 831-833, the contents of which are incorporated by reference. To obtain 15', di-(2-picolyl)amine was treated with acrylonitrile under microwave for 30 minutes, and reduced to 14' using Raney-Nickel solution with NaBH$_4$. Then, 11' was connected with 14' under EDC coupling condition to give 15' as a modified trident ligand for capturing rhenium (Scheme 3').

Scheme 2'

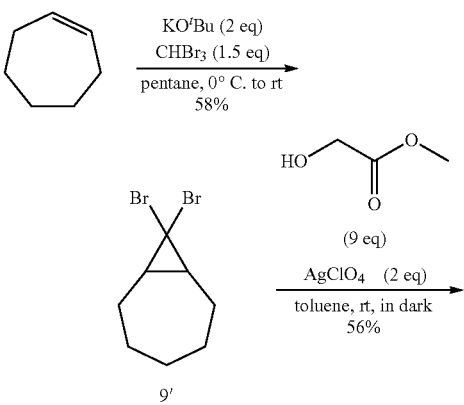

43
-continued

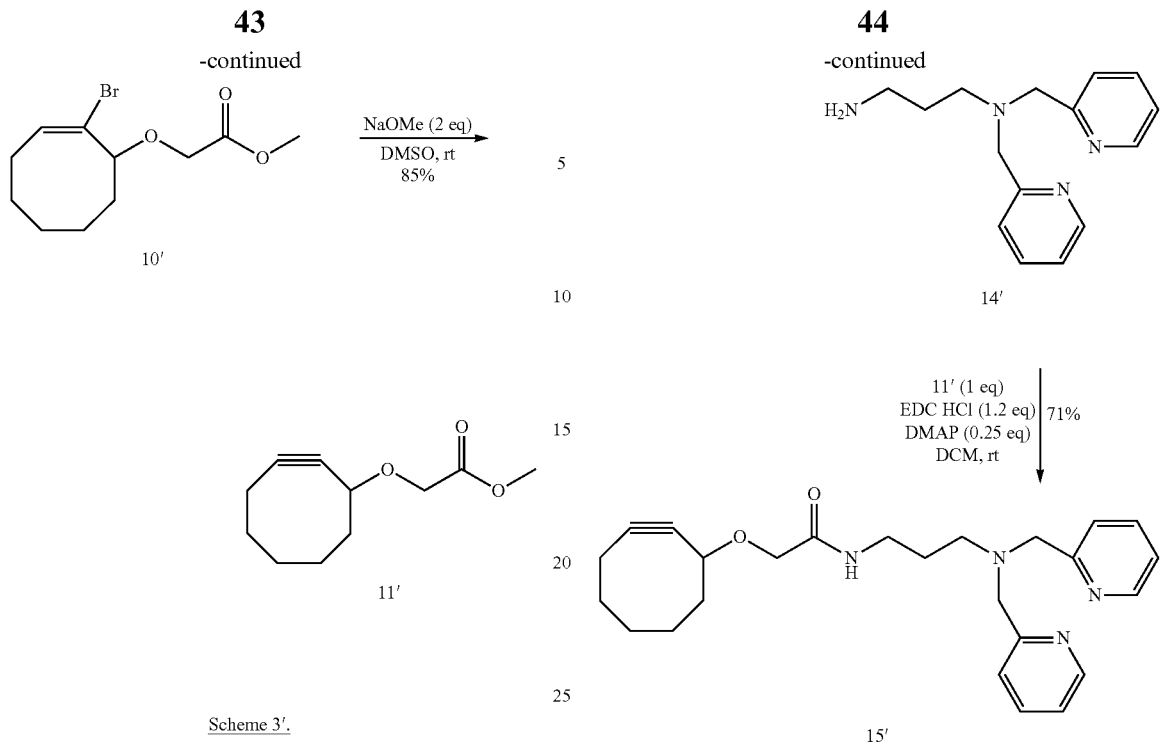

Scheme 3'.

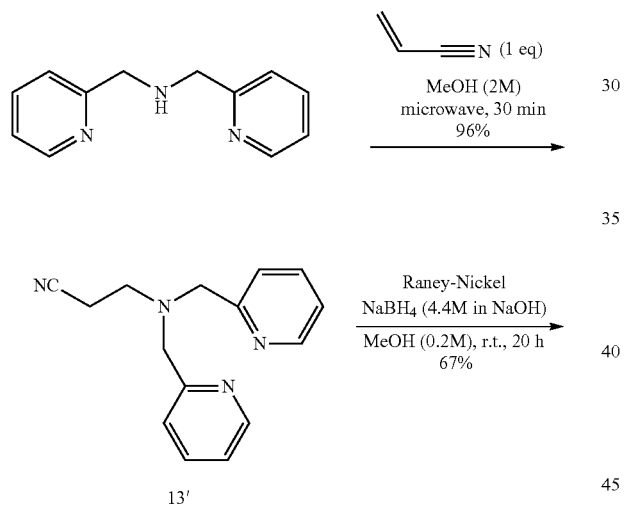

44
-continued

Synthesis of Biotin-Triazine-Linker-Drug-DPA-Re(CO)₃ Conjugate. Re complex, [Re(CO)₃(H₂O)₃]⁺Br⁻ (16'), was prepared from commercial available bromopentacarbonyl-rhenium(I) (Re(CO)₅Br) followed by the reported procedure in Lazarova, N.; James, S.; Babich, J.; Zubieta, J. A convenient synthesis, chemical characterization and reactivity of [Re(CO)₃(H₂O)₃]Br: the crystal and molecular structure of [Re(CO)₃(CH₃CN)₂Br]. *Inorganic Chemistry Communications* 2004, 7, 1023-1026, the contents of which are incorporated by reference (Scheme 4').

Scheme 4'

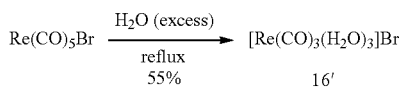

Compound 8' was reacted with compound 15', where n is 3 to generate compound 18', as shown in Scheme 5'.

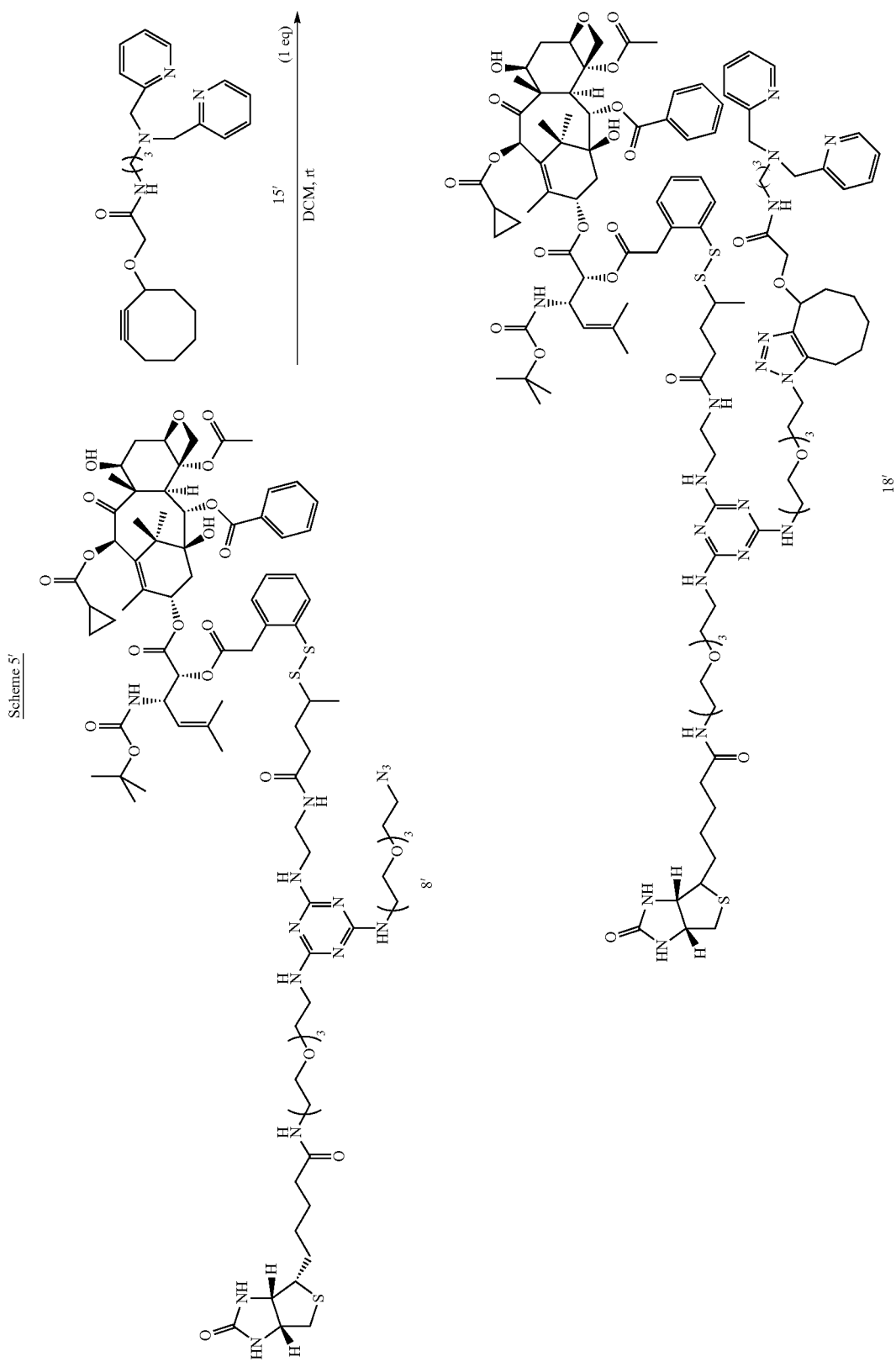
Scheme 5'

A dpa chelating ligand 15' was used to yield 18', as depicted in Scheme 5'. Conjugate ligand 18 could use a free sp$^a$ N instead of the amide sp$^2$ N to coordinate with metal. Compound 22' was generated under microwave conditions (Scheme 6'), which was confirmed by LC-MS-TOF. Compound 22' was isolated by preparative HPLC as a white solid. For hot synthesis with $^{99m}$Tc tricarbonyl species, conjugate ligand 18' is readily used for capturing $^{99m}$Tc under the same reaction condition. The reaction time has been optimized to 10 minutes and the purification has been established for in vivo SPECT study.

(p-SCN-Bn-NOTA) chelating ligand (28'). To chelate Cu species for PET study, an NOTA moiety was selected which was commonly used to chelate gallium-68 ($^{68}$Ga), copper-64 ($^{64}$Cu) or indium 111 ($^{111}$In). To attach the copper-free click cyclooctyne with NOTA to generate compound 28', extra steps were required. Because one amino group was planned to react with p-SCN-Bn-NOTA, instead of directly coupling 11' with ethylenediamine, activated OSu ester 26' was generated. Then, to a solution of 10 eq excess diamine in dichloromet, 26' was dissolved previously and slowly added under 0° C. Then commecially available p-SCN-Bn-NOTA was reacted with 27' to yield 28' (Scheme 7'). Purification of 28' was done by preparative HPLC.

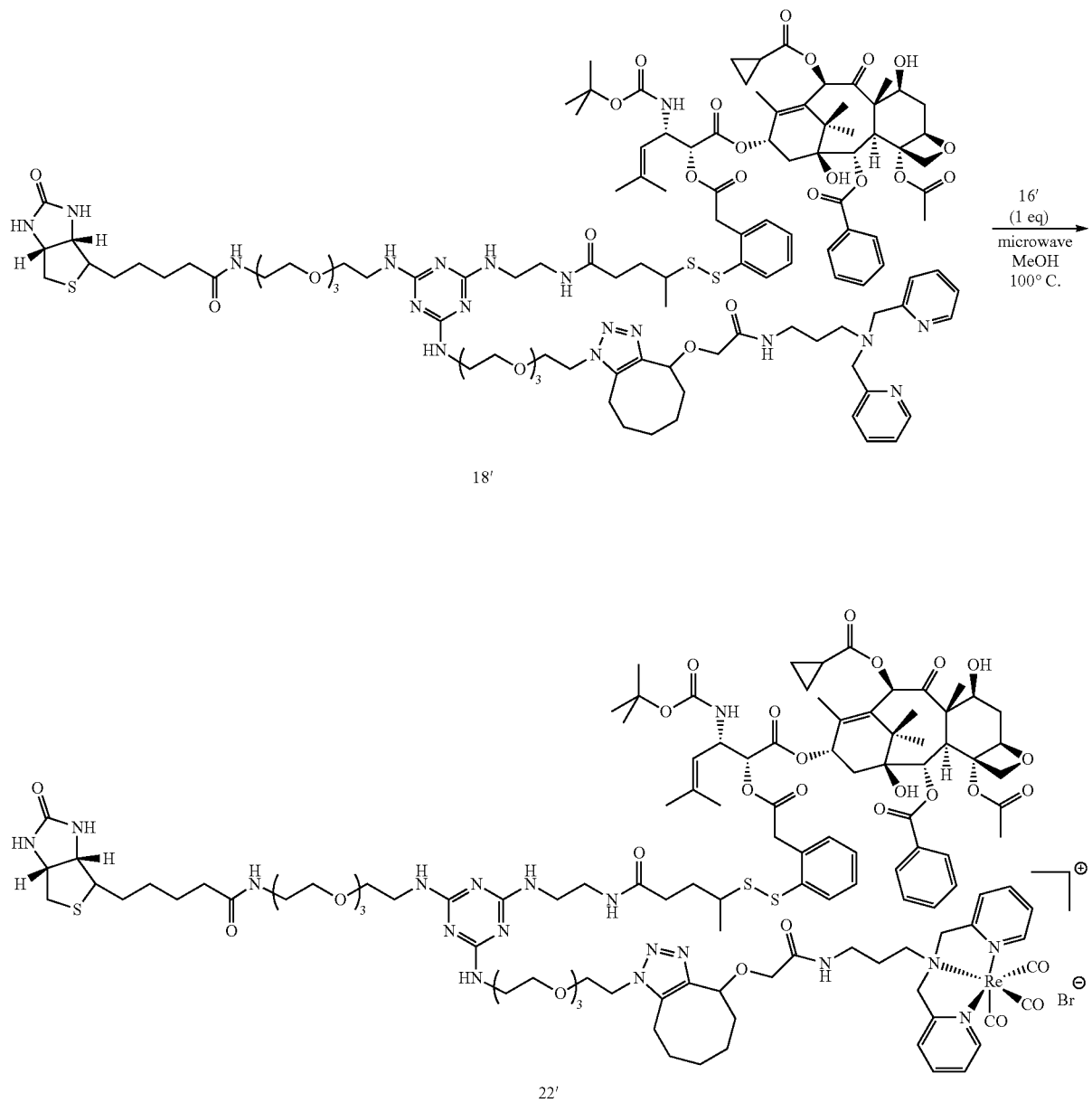

Synthesis of click-ready cyclooctyne-p-isothiocyanato-benzyl-1,4,7-triazacyclononane-N,N',N''-triacetic acid

Scheme 7'
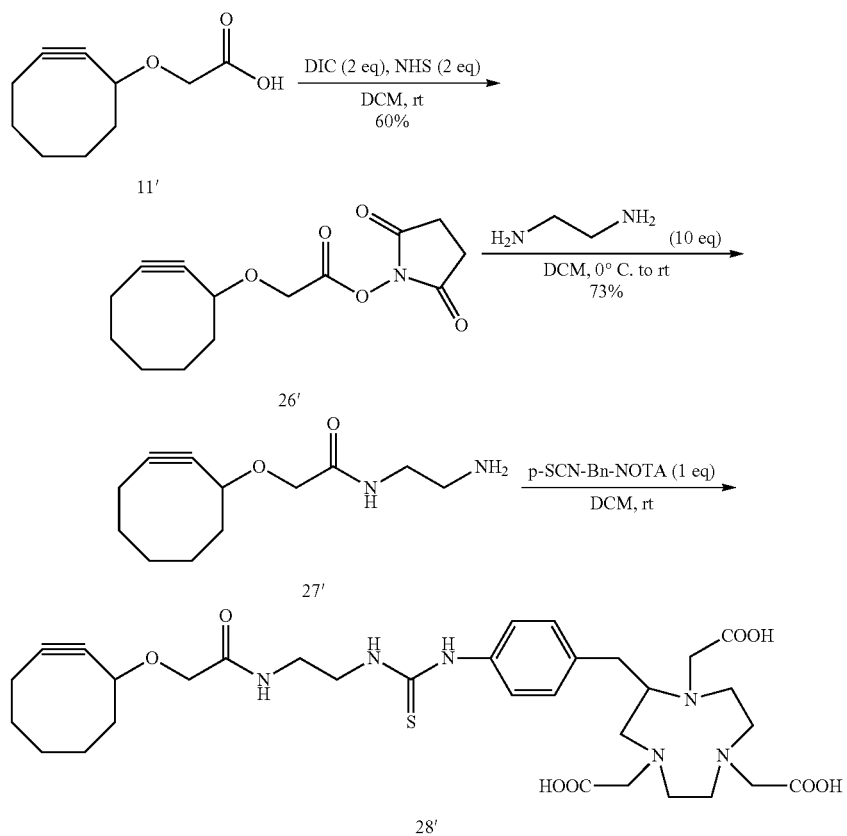
Synthesis of Biotin-Triazine-Linker-Drug-NOTA-Cu conjugate. The biotin-triazine-linker-taxoid-NOTA-Cu conjugate 30' was synthesized by Cu-free click between intermediates 8 and 28 under microwave irridation, followed by addition of copper(II) chloride to generate theranostic Cu-complex 30' (Scheme 8').
Scheme 8'
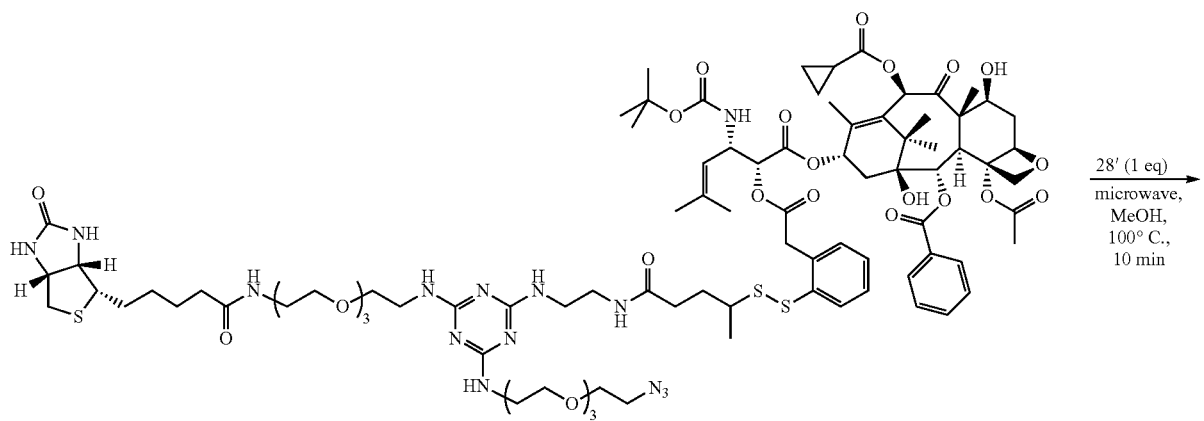

It should be noted that the compounds of Formula III, such as compound 30', may be administered alone in the methods described herein, or they may also be presented as one or more pharmaceutical compositions (e.g., formulations). The aforementioned compounds may be formulated with one or more pharmaceutically acceptable carriers, adjuvants, excipients, diluents, fillers, buffers, stabilizers, preservatives, lubricants, or other materials well known to those skilled in the art. Accordingly, in an embodiment, a pharmaceutical composition is provided comprising at least one compound of Formula III, such as compound 30', and a pharmaceutically acceptable carrier therefor. The methods described herein include administration of one or more pharmaceutical compositions, as discussed herein, in which a compound of Formula III, such as compound 30', described herein is admixed together with one or more pharmaceutically acceptable carriers, which may additionally contain one or more excipients, buffers, adjuvants, stabilizers, or other materials, as described hereinabove for compounds of Formula I, the contents of which are incorporated by reference.

Suitable carriers, excipients, etc. can be found in standard pharmaceutical texts, for example, Remington's Pharmaceutical Sciences, 18th edition, Mack Publishing Company, Easton, Pa., 1990.

It will be appreciated that appropriate dosages of the compounds and compositions comprising the active compounds of Formula III, including compound 30', can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In an embodiment, a suitable dose of the compound of formula III, such as compound 30', may be in the range of about 0.1 mg per kilogram to about 500 mg per kilogram body weight of the subject per day, in another embodiment, a suitable dose of the active compound may be in the range of about 1 mg per kilogram to about 100 mg per kilogram body weight of the subject per day, and in a still further embodiment, a suitable dose of the active compound may be in the range of about 5 mg per kilogram to about 50 mg per kilogram body weight of the subject per day.

The disclosure further provides a method of treating cancer in a subject in need of treatment, comprising administering the subject a therapeutically effective amount of a compound of Formula IV described herein.

The disclosure further provides a method of reducing the proliferation of a cancer cell, comprising contacting the cancer cell with an effective amount of a compound of Formula IV, described herein. The cancers for which compounds of Formula IV are effective are the cancers listed hereinabove.

The following examples further illustrate the present invention.

General Methods: $^1$H NMR was measured on a Varian 300 MHz NMR spectrometer. The melting points were measured on a "Uni-melt" capillary melting point apparatus from Arthur H. Thomas Company, Inc. TLC analyses were performed on Merck DC-alufolien with Kieselgel 60F-254 and were visualized with UV light and stained with sulfuric acid-EtOH, 10% PMA-EtOH, 10% Vanillin-EtOH with 1% sulfuric acid or Ninhydrin-butanol with 10% AcOH. Column chromatography was carried out on silica gel 60 (Merck; 230-400 mesh ASTM). Chemical purity was determined with a shimazu HPLC, using a Phenomenex Curosil-B column, employing CH$_3$CN/water as the solvent system with a flow rate of 1 mL/min. Chiral HPLC analysis for the determination of enantiomeric excess was carried out with a shimazu HPLC, using a DAICEL-CHIRACEL OD chiral column (25×0.46 cm i.d.), employing hexane/2-propanol as the solvent system with a flow rate of 1.0 mL/min. Matrix-assisted laser desorption/ionization (MALDI)-TOF analysis for determination of molecular weight was facilitated by ICB&DD using matrix. LC-TOF analysis for determination of molecular weight was facilitated by ICB&DD, using Kinetex C18 analytical column with 2.6 μm, 100 A, 2.1×100 mm. Solvents are 0.1% Ac-0.02% TFA as solvent A and CH$_3$CN as solvent B. Running temperature is 35° C., flow rate is 0.5 mL/min.

Materials: The chemicals were purchased from Sigma Aldrich Company, Fischer Company or Acros Organic Company. Dichloromethane and methanol were dried before use by distillation over calcium hydride under nitrogen. Ether and THF were dried before use by distillation over sodium-benzophenone kept under nitrogen. Dry DMF was purchased from EMD chemical company, and used without further purification. Reaction flasks were dried in a 100° C. oven and allowed to cool to room temperature in a desiccator over "Drierite" (calcium sulfate) and assembled under an inert nitrogen gas atmosphere.

2-Chloro-4-(11-biotinylamino-3,6,9-trioxaundecyl) amino-6-(11-azido-3,6,9-trioxaundecyl)amino-1,3,5-triazine (3'). To a 100 mL round-bottomed flask was added cyanuric chloride (124 mg, 0.67 mmol) dissolved in 0.02 THF (33.5 mL) under 0° C. in an ice-water bath. To this solution was slowly added 1 equivalent of 1' (146 mg, 0.67 mmol) dissolved in 2 mL THF, followed by addition of 1.5 equivalents of DIPEA (86.6 mg, 0.67 mmol, 0.12 mL). The resulting solution was allowed to warm to room temperature and stirred for 2 hours. Then the reaction mixture was transferred to another rbf containing 1 equivalent of 2' (280 mg, 0.67 mmol), followed by addition of 1.5 eq DIPEA (86.6 mg, 0.67 mmol, 0.12 mL). The reaction mixture was heated to 60° C. and allowed to stir overnight. Upon completion, the solvent was removed and the product was purified by silica gel column chromatography eluting 0-10% methanol in dichloromethane to yield 3' as a white sticky solid (210 mg, 0.28 mmol, 42%): $^1$H NMR (500 MHz, CDCl$_3$) δ 0.74-0.77 (m, J=6.37 Hz, 1 H), 0.78 (t, J=6.93 Hz, 1 H), 1.02 (d, J=6.51 Hz, 1 H), 1.16-1.20 (m, 2 H), 1.32-1.35 (m, 3 H), 1.43-1.46 (m, 2 H), 1.54-1.59 (m, 3 H), 1.64-1.65 (m, 1 H), 2.10-2.14 (m, 2 H), 2.65 (d, J=12.67 Hz, 1 H), 2.79 (dd, Ja=4.76 Hz, Jb=12.74 Hz, 1 H), 3.00-3.05 (m, 2 H), 3.30-3.33 (m, 3 H), 3.48-3.58 (m, 26 H), 3.58-3.68 (m, 1 H), 4.22 (m, 1 H), 4.41 (t, J=5.53 Hz, 1 H), 6.14 (m, 1 H). $^{13}$C NMR (500 MHz, CDCl$_3$) δ 11.3, 11.9, 14.0, 17.3, 18.5, 22.5, 23.4, 25.5, 25.6, 28.1, 28.3, 28.9, 29.5, 31.4, 34.5, 35.8, 35.9, 35.9, 39.0, 40.4, 40.5, 40.6, 40.7, 41.9, 42.8, 50.6, 53.6, 55.6, 56.6, 60.2, 61.7, 69.2, 69.9, 69.9541, 70.0, 70.3, 70.5, 70.5, 71.2, 164.3, 165.5, 165.6, 168.1, 168.9, 169.0, 173.3, 173.4. HRMS (TOF) [M+H]$^+$ m/z calcd. for C$_{29}$H$_{51}$ClN$_{11}$O$_8$S$^+$: 748.3326, found 748.3321.

2-(N-Boc-aminoethyl)amino-4-(11-biotinylamino-3,6,9-trioxaundecyl)amino-6-(11-azido-3,6,9-trioxaundecyl) amino-1,3,5-triazine (5') Compound 3' (210 mg, 0.28 mmol) was dissolved in 0.02 M THF (14 mL). To the solution was added 1.5 equivalents of 4' (67.3 mg, 0.42 mmol), followed by addition of 1.5 equivalents of DIPEA (54 mg, 0.42 mmol, 0.07 mL). The resulting solution was allowed to heat to reflux overnight. The reaction was monitored by FIA. Upon completion, the solvent was removed and the product was purified by silica gel column chromatography eluting 0-15% methanol in dichloromethane to yield 5' as a white sticky solid (150 mg, 0.17 mmol, 61%). $^1$H NMR (500 MHz, CDCl$_3$) δ 0.78 (m, 1 H), 0.79 (t, J=6.8 Hz, 2 H), 1.17 (m, 2 H), 1.34 (s, 9 H), 1.54-1.57 (m, 3 H), 1.64-1.65 (m, 1 H), 2.14 (m, 2 H), 2.70 (d, J=12.75 Hz, 1 H), 2.81 (dd, Ja=4.7 Hz, Jb=12.55 Hz, 1 H), 3.03-3.07 (m, 2 H), 3.20 (m, 2 H), 3.32 (m, 3 H), 3.51-3.62 (36 H), 4.27 (m, 1 H), 4.44 (m, 1 H), 6.70 (m, 1 H). $^{13}$C NMR (500 MHz, CDCl$_3$) δ 11.3, 14.0, 18.7, 20.6, 22.6, 25.2, 25.6, 28.0, 28.3, 29.0, 29.6, 31.5, 34.4, 34.6, 35.6, 38.3, 39.1, 40.2, 40.3, 40.4, 40.6, 50.1, 50.6, 53.4, 55.7, 60.2, 60.3, 62.0, 69.8, 69.9, 70.0, 70.1, 70.2, 70.3, 70.5, 70.5, 79.0, 79.5, 156.2, 156.5, 164.3, 173.8. HRMS (TOF) [M+H]$^+$ m/z calcd. for C$_{36}$H$_{66}$N$_{13}$O$_{10}$S$^+$: 872.4771, found 872.4766.

2-(2-Aminoethyl)amino-4-(11-biotinylamino-3,6,9-trioxaundecyl)amino-6-(11-azido-3,6,9-trioxaundecyl)amino-1, 3,5-triazine trifluoroacetic acid salt (6'). To a 10 mL round-bottomed flask was added 5' (150 mg, 0.17 mmol) dissolved in 0.02 M dichloromethane (9 mL). To this solution was added 20 volume % trifluoroacetic acid (1.8 mL) and the resulting solution was stirred for 2 hours under room temperature. The reaction was monitored by TLC. Upon completion, the solvent was removed by lyophilizer to afford the formation of crude 6' (234 mg), which was directly taken for the next step: $^1$H NMR (700 MHz, CD$_3$OD) δ 1.16-1.1'8 (m, 2 H), 1.31-1.48 (m, 6 H), 1.77 (s, 2 H), 1.96 (s, 2 H), 2.44 (d, J=12.74 Hz, 1 H), 2.65 (dd, Ja=4.83 Hz, Jb=12.74 Hz, 1 H), 2.94 (m, 3 H), 3.05 (s, 2 H), 3.09 (m, 3 H), 3.28 (m, 3 H), 3.38 (m, 32 H), 4.04 (m, 1 H), 4.23 (m, 1 H). $^{13}$C NMR (700 MHz, CD$_3$OD) δ 25.4, 28.1, 28.3, 35.3, 37.9, 38.8, 38.9, 39.1, 39.6, 40.2, 40.3, 50.3, 55.5, 60.2, 62.0, 68.5, 69.1, 69.2, 69.6, 69.8, 69.9, 70.0, 70.1, 113.2, 114.9, 116.5, 116.7, 118.2, 155.0, 155.7, 156.3, 57.3, 159.6, 159.8, 162.7, 163.4, 164.0, 164.6, 174.7. HRMS (TOF) [M+H]$^+$ m/z calcd. for $C_{31}H_{58}N_{13}O_8S^+$: 772.4247, found 386.7166, 772.4257.

2-[2-(Taxoid-SS-Linker)amidoethyl]amino-4-(11-biotinylamino-3,6,9-trioxaundecyl)amino-6-(11-azido-3,6,9-trioxaundecyl)amino-1,3,5-triazine (8'). To a 25 mL round-bottomed flask were added crude 6' (234 mg) and 1.2 equivalents of 7' (246 mg, 0.2 mmol). 0.01 M dichloromethane (17 mL) was added to partially dissolve the mixture, followed by the addition of 1.5 equivalents of diisopropylethylamine (DIPEA) (33 mg, 0.26 mmol, 0.045 mL). The reaction mixture was allowed to stir under room temperature for 15 hours. Upon completion, the solvent was removed and the product was purified by silica gel column chromatography eluting 0-20% methanol in dichloromethane to yield 8' as a white solid (209 mg, 0.11 mmol, 65% for two steps). $^1$H NMR (500 MHz, CDCl$_3$) δ 0.91-0.92 (m, 3 H), 1.05 (m, 2 H), 1.10 (m, 2 H), 1.30 (s, 9 H), 1.60 (s, 2 H), 1.66 (s, 3 H), 1.67 (s, 3 H), 1.79-1.81 (m, 2 H), 1.85 (s, 3 H), 2.03 (s, 1 H), 2.13 (m, 2 H), 2.30 (s, 3 H), 2.46 (m, 1 H), 2.68 (m, 1 H), 2.82 (m, 2 H), 3.50-3.66 (m, 40 H), 3.74 (d, J=6.75 Hz, 1 H), 3.90 (d, J=16.55 Hz, 1 H), 4.02 (d, J=16.4 Hz, 1 H), 4.11 (d, J=8.05 Hz, 1 H), 4.23 (s, 2 H), 4.35 (m, 1 H), 4.43 (m, 1 H), 4.89-4.92 (m, 3 H), 5.08 (s, 1 H), 5.26 (s, 2 H), 5.61 (d, J=6.6 Hz, 1 H), 6.12 (m, 1 H), 6.26 (s, 1 H), 7.17-7.20 (m, 2 H), 7.41 (t, J=7.45 Hz, 2 H), 7.54 (t, J=7.25 Hz, 1 H), 7.73 (d, J=7.6 Hz, 1 H), 8.04 (d, J=7.55 Hz, 2 H), 10.74 (broad, 1H). $^{13}$C NMR (500 MHz, CDCl$_3$) 9.1, 9.2, 9.5, 11.8, 13.0, 14.7, 17.5, 18.4, 18.7, 20.3, 20.6, 22.0, 22.4, 25.2, 25.6, 26.5, 27.8, 29.0, 29.6, 31.2, 33.3, 34.4, 34.6, 35.5, 35.6, 36.0, 38.6, 39.0, 40.1, 41.9, 43.1, 45.8, 46.1, 50.6, 53.0, 55.5, 58.3, 60.5, 62.1, 69.2, 69.9, 70.0, 70.2, 70.4, 71.7, 71.9, 75.0, 75.1, 75.4, 76.3, 79.0, 79.7, 80.8, 84.4, 113.2, 115.6, 117.9, 119.8, 120.2, 127.6, 128.3, 128.6, 129.2, 130.1, 130.9, 132.4, 133.1, 133.6, 137.4, 137.5, 137.8, 143.0, 155.0, 161.2, 161.5, 161.8, 162.1, 164.6, 166.8, 168.2, 169.7, 170.4, 173.1, 173.9, 174.8, 204.0. HRMS (TOF) [M+H]$^+$ m/z calcd. for $C_{89}H_{129}N_{14}O_{25}S_3^+$: 1889.8410, found 1890.8429.

N-(3-(Bis(pyridin-2-ylmethyl)amino)propyl)-2-(cyclooct-2-yn-1-yloxy)acetamide (15'). To a 25 mL round-bottomed flask was added 11' (67 mg, 0.37 mmol), 0.25 eq DMAP (11.3 mg, 0.09 mmol), and 1.2 equivalents of EDC HCl salt (85 mg, 0.44 mmol) dissolved in 8 mL dichloromethane under room temperature. To this solution was added 1 equivalent of 14' (95 mg, 0.37 mmol) dissolved in 2 mL dichloromethane dropwise. The reaction was allowed to stir under room temperature overnight and monitored by TLC. Upon completion, the product was purified straight away by column chromatography, eluting with 0-10% methanol in dichloromethane to afford 15' as a yellow oil (110 mg, 0.26 mmol, 71%). $^1$HNMR (500 MHz, CDCl$_3$) δ 1.22-1.29 (m, 1 H), 1.36-1.43 (m, 1 H), 1.53-1.59 (m, 1 H), 1.58-1.64 (m, 2 H), 1.69-1.83 (m, 4 H), 1.85-1.93 (m, 1 H), 2.04-2.09 (m, 1 H), 2.15-2.20 (m, 1 H), 2.20-2.25 (m, 1 H), 2.57 (t, 0.1=6.7 Hz, 2 H), 3.27 (t, J=7 Hz, 2 H), 3.79 (s, 4 H), 3.98 (d, J=14.9 Hz, 1 H), 7.11 (dt, Ja=1.05 Hz, Jb=4.85 Hz, 2 H), 7.46 (d, J=7.85 Hz, 2 H), 7.61 (dt, Ja=1.8 Hz, Jb=7.65 Hz, 2 H), 8.85 (dd, Ja=1.8 Hz, Jb=4.2 Hz, 2 H). $^{13}$C NMR (500 MHz, CDCl$_3$) δ 20.6, 23.5, 26.2, 26.8, 29.6, 34.2, 37.3, 42.1, 51.9, 60.4, 68.4, 73.0, 91.3, 101.5, 122.0, 123.0, 123.1, 136.4, 149.0, 159.4, 169.4. HRMS (TOF) [M+H]$^+$ m/z calcd. for $C_{25}H_{33}N_4O_2^+$: 421.2598, found 421.2625.

Biotin-Triazine-Linker-DPA Conjugate (18'). To a 5 mL round-bottomed flask was added 8' (50 mg, 26 μmol) dissolved in 0.05 M dichloromethane (0.5 mL). To the solution was added 1.1 equivalents of 15' (12 mg, 30 μmop dissolved in 0.1 mL dichloromethane. The resulting solution was allowed to stir under room temperature for 72 hours and the reaction was monitored by TLC. Upon completion, the solvent was removed and the product was purified by silica gel column chromatography eluting 0-30% methanol in dichloromethane to yield 18' as a white solid (40 mg, 17 μmol, 67%): $^1$H NMR (700 MHz, CDCl$_3$) δ 0.83-0.84 (m, 2 H), 0.86-0.88 (t, J=7.1 Hz, 2 H), 0.95 (d, J=6.7 Hz, 1 H), 1.10 (m, 2 H), 1.14 (s, 2 H), 1.23 (s, 3 H), 1.24 (s, 3 H), 1.34 (s, 3 H), 1.40 (broad, 4 H), 1.43-1.44 (t, J=7.4 Hz, 2 H), 1.55 (m, 3 H), 1.65 (s, 3 H), 1.69 (s, 3 H), 1.71 (s, 3 H), 1.89 (s, 2 H), 2.20 (m, 2 H), 2.34 (s, 2 H), 2.50 (quinine, 1 H), 2.60 (m, 1 H), 2.69 (m, 1 H), 2.74-2.76 (m, 1 H), 2.86 (m, 2 H), 3.08-3.11 (quart, J=7.4 Hz, 4 H), 3.30 (s, 2 H), 3.45 (t, J=4 Hz, 2 H), 3.54-3.62 (m, 16 H), 3.67 (quinine, J=6.8 Hz, 2 H), 3.79 (d, J=6.9 Hz, 2 H), 3.81 (s, 2 H), 3.86 (s, 1 H), 3.94 (m, 1 H), 4.06 (d, J=16.7, 1 H), 4.16 (d, J=8.5, 1 H), 4.28 (d, J=8.5 Hz, 1 H), 4.38 (m, 1 H), 4.48 (m, 1 H), 4.67 (s, 1 H), 4.94 (m, 2 H), 5.11 (s, 1 H), 5.65 (d, J=7 Hz, 1 H), 6.16 (t, 1 H), 6.30 (s, 1 H), 7.14 (s, 2 H), 7.20 (t, J=7.3 Hz, 1 H), 7.27 (t, J=7.6 Hz, 1 H), 7.45 (t, J=7.6 Hz, 3 H), 7.58 (t, J=7.4 Hz, 1 H), 7.64 (t, 2 H), 7.71 (m, 1 H), 7.77 (d, J=7.3 Hz, 1 H), 8.09 (d, J=7.6 Hz, 2 H), 8.15 (m, 1 H). $^{13}$C NMR (700 MHz, CDCl$_3$) δ 9.1, 9.2, 9.6, 11.4, 11.8, 13.0, 14.1, 14.8, 18.5, 18.8, 20.4, 20.7, 22.1, 22.4, 22.6, 25.3, 25.7, 26.6, 28.2, 29.1, 29.7, 31.6, 33.4, 34.5, 34.7, 35.5, 36.1, 38.7, 39.0, 40.5, 41.9, 43.2, 45.8, 46.3, 47.6, 49.1, 50.7, 51.8, 58.4, 60.3, 61.9, 68.4, 69.4, 69.8, 70.1, 70.2, 70.4, 70.5, 71.8, 72.0, 75.0, 75.1, 75.5, 76.4, 79.1, 79.8, 80.1, 84.5, 115.9, 117.6, 119.9, 122.1, 123.1, 127.7, 128.3, 128.6, 129.3, 130.2, 132.6, 133.6, 134.3, 136.7, 137.6, 137.9, 143.0, 149.1, 155.0, 162.1, 166.9, 168.3, 169.7, 170.5, 172.9, 173.5, 174.9, 204.1. HRMS (TOF) [M+H]$^+$ m/z calcd. for $C_{114}H_{161}N_{18}O_{27}S_3^+$: 2310.0935, found 771.0345, 1156.0487 (via deconvolution).

Biotin-Triazine-Linker-DPA-Re Conjugate (22'). To a 10 mL microwave tube was added 18' (2.3 mg, 1 μmol) and 1 equivalent of 16' (0.4 mg, 1 μmop dissovled in 1 mL MeOH. The tube was sealead and allowed to heated by microwave under 100° C. for 10 minutes with stirring. Then the solution was cooled down to room temperature and filter out to remove undissovled solid. Then, the filtrate was concentrated to afford crude product, which was purified by preparative HPLC to give 22' as a white solid (3 mg, 1 μmol, 99%): $^1$H NMR (700 MHz, CDCl$_3$) δ 0.85-0.87 (m, 2 H), 0.88-0.89 (t, J=6.9 Hz, 2 H), 0.96 (d, J=6.7 Hz, 1 H), 1.10 (m, 1 H), 1.15 (s, 2 H), 1.24 (s, 3 H), 1.25 (s, 3 H), 1.35 (s, 3 H), 1.43 (d, J=6.7 Hz, 4 H), 1.50-1.54 (m, 5 H), 1.65 (s, 3 H), 1.71 (s, 2 H), 1.76 (broad, 4 H), 1.89 (s, 2 H), 2.24 (m, 2 H), 2.35 (s, 2 H), 2.52 (m, 1 H), 2.88 (m, 1 H), 3.11-3.14 (m, 2 H), 3.35 (s, 1 H), 3.43 (broad, 2 H), 3.64 (m, 8 H), 3.70 (m, 2 H), 3.79 (d, J=5.8 Hz, 2 H), 3.97 (m, 1 H), 4.07 (m, 1 H), 4.17-4.19 (m, 2 H), 4.29 (d, J=8.1 Hz, 1 H), 4.40 (m, 1 H), 4.48 (m, 1 H), 4.95 (m, 2 H), 5.11 (s, 1 H), 5.6 (d, J=6.7 Hz, 1 H), 6.16 (m, 1 H), 6.30 (s, 1 H), 7.10 (s, 1 H), 7.41 (s, 1 H), 7.46 (t, J=7.4 Hz, 1 H), 7.59 (t, J=6.9 Hz, 1 H), 7.78 (m, 2 H), 7.84 (s, 2 H), 8.10 (d, J=7.4 Hz, 2 H), 8.65 (m, 2 H). $^{13}$C NMR (700 MHz, CDCl$_3$) δ 9.1, 9.6, 11.4, 11.9, 13.0, 14.1, 14.8, 17.4, 18.5, 18.6, 18.8, 20.4, 20.7, 22.1, 22.5, 22.7, 25.3, 25.7, 26.6, 28.2, 29.1, 29.4, 29.7, 31.6, 31.9, 34.5, 34.7, 35.5, 38.7, 42.1, 43.2, 53.8, 58.4, 70.1, 71.8, 75.1, 75.5, 79.2, 80.1, 84.5, 115.9, 117.5, 128.4, 128.7, 129.3, 130.2, 133.6, 140.4, 162.3, 166.9. HRMS (TOF) [M+H]$^+$ m/z calcd. for $C_{117}H_{160}N_{18}O_{30}ReS_3^+$: 2580.0267, found 861.0172, 1291.0206, 2581.0318.

2,5-Dioxopyrrolidin-1-yl 2-(cyclooct-2-yn-1-yloxy)acetate (26'). Compound 11' (180 mg, 1 mmol) was dissolved in 0.1 M dichloromethane (10 mL) at room temperature. To the resulting solution was added 2 equivalents of N-hydroxysuccinimide (NHS) (228 mg, 2 mmol), followed by addition of 2 equivalents of DIC (280 mg, 2 mmol, 0.3 mL) dropwise. The reaction was allowed to stir under room temperature for 28 hours. The white precipitate was filtered out and solvent was removed by rotary evaporation. The crude material was purified by silica gel column chromatography eluting 0-35% ethyl acetate in hexanes to yield 26' as a slight yellow solid (172 mg, 0.6 mmol, 60%): $^1$H NMR (500 MHz, CDCl$_3$) δ 1.43-1.50 (m, 1 H), 1.59-1.64 (m, 2 H), 1.74-1.91 (m, 3 H), 1.99-2.05 (m, 1H), 2.09-2.18 (m, 2 H), 2.21-2.27 (m, 1 H), 2.82 (s, 4 H), 4.36-4.39 (d, J=17.05 Hz, 1 H), 4.49-4.53 (d, J=17.1 Hz, 1H). $^{13}$C NMR (500 MHz, CDCl$_3$) δ 20.6, 23.4, 25.5, 26.0, 29.5, 34.2, 42.1, 63.8, 73.4, 90.7, 102.3, 165.8, 168.8. HRMS (TOF) [M+H]$^+$ m/z calcd. for C$_{14}$H$_{18}$NO$_5^+$: 280.1179, found 280.1167.

N-(2-Aminoethyl)-2-(cyclooct-2-yn-1-yloxy)acetamide (27). To 26' (172 mg, 0.6 mmol) was dissolved in 5 mL dichloromethane. In another round bottom flask was 'dissolved 10 eq ethylenediamine (360 mg, 6 mmol) dissolved in 0.01 M dichloromethane (60 mL) at 0° C. in an ice-water bath. To this solution was added the 26' in dichloromethane dropwise. Solution turned cloudy while adding. The reaction mixture was allowed to warm to room temperature and stirred overnight. Upon completion, the precipitate was filtered out. 50 mL of water was added and the product was extracted with dichloromethane (30 mL×3). The combined organic layers were dried over MgSO$_4$ and concentrated in vacuum to give 27' as yellow oil (99 mg, 0.44 mmol, 73%): $^1$H NMR (500 MHz, CDCl$_3$) δ 1.43-1.49 (m, 1 H), 1.61-1.68 (m, 2 H), 1.80-2.01 (m, 3 H), 2.14-2.24 (m, 2 H), 2.84 (t, J=5.75 Hz, 2 H), 3.34 (m, 2 H), 3.88-3.91 (d, J=15.15 Hz, 1 H), 4.04-4.07 (d, J=15.15 Hz, 1 H). 4.24 (m, 1 H), 6.81 (broad, 1 H). $^{13}$C NMR (500 MHz, CDCl$_3$) δ 20.6, 26.3, 29.6, 29.7, 34.2, 41.5, 41.7, 42.2, 68.4, 73.3, 91.2, 101.8, 170.0. HRMS (TOF) [M+Fi]$^+$ m/z calcd. for C$_{12}$H$_{21}$N$_2$O$_2^+$: 225.1598, found 225.1597.

2,2',2"-(2-(4-(3-(2-(2-(Cyclooct-2-yn-1-yloxy)acetamido)ethyl)thioureido)-benzyl)-1,4,7-triazonane-1,4,7-triyl)triacetic acid (28'). To a round-bottom flask was added 27' (40 mg, 0.18 mmol) and 1 equivalent of commercially available p-SCN-Bn-NOTA HCl salt (100 mg, 0.18 mmol) dissolved in dichloromethane (2 mL). To the suspension was added 3 equivalents of triethylamine (0.11 mL) and the reaction mixture was allowed to stir at room temperature for 18 hours and monitored by FIA. Upon completion, the crude product was purified by preparative HPLC and 28' was isolated as a cotton-like solid (24 mg): $^1$H NMR (700 MHz, D$_2$O) δ 1.19-1.21 (m, 6 H), 1.24 (t, J=7.21 Hz, 1 H), 1.32-1.36 (m, 1 H), 1.46-1.51 (m, 1 H), 1.57-1.61 (m, 1 H), 1.67 -1.74 (m, 2 H), 1.82-1.83 (m, 1H), 1.87-1.91 (m, 1 H), 2.06-2.09 (m, 2 H), 2.15-2.17 (m, 1 H), 2.73 (m, 1 H), 2.93 (m 2 H), 3.11-3.14 (m, 4 H), 3.31-3.37 (m, 6 H), 3.47 (m, 1 H), 3.51 (m, 1 H), 3.64 (m, 3 H), 3.72-3.81 (m, 6 H), 3.93 (s, 2 H), 4.29 (s, 1 H), 7.17 (d, J=7.35 Hz, 2 H), 7.32 (s, 1 H). $^{13}$C NMR (700 MHz, D$_2$O) δ 6.5, 8.2, 20.0, 25.7, 29.0, 33.8, 41.5, 46.6, 52.1, 52.4, 67.5, 73.7, 91.1, 103.7, 126.2, 130.5, 172.7. HRMS (TOF) [M+H]$^+$ m/z calcd. for C$_{32}$H$_{47}$N$_6$O$_8$S$^+$: 675.3171, found 675.3184.

Biotin-Triazine-Linker-Taxoid-NOTA-Cu Conjugate (29'). To a microwave vial was added 8' (81 mg, 43 μmop and 1 equivalent of 28' (29 mg, 43 μmol) dissolved methanol/distilled water=3:1 (total 4 mL). The vial was sealed and heated to 100° C. for 10 minutes by microwave. Then, the product was purified by preparative HPLC to give 29' as a white solid (56 mg, 22 μmol, 51%): $^1$H NMR (700 MHz, CD$_3$OD) δ 0.99 (m, 2 H), 1.03 (m, 1 H), 1.09 (m, 1 H), 1.19 (s, 4 H), 1.27 (m, 3 H), 1.38 (d, J=6.65 Hz, 1 H), 1.43 (s, 9 H), 1.60-1.65 (m, 4 H), 1.67 (s, 3 H), 1.76-1.78 (d, J=14.7 Hz, 2 H), 1.81 (m, 3 H), 1.91 (m, 1 H), 1.94 (s, 2 H), 2.05 (m, 2 H), 2.14 (m, 2 H), 2.21 (t, J=5.2 Hz, 2 H), 2.27 (m, 3 H), 2.40 (s, 2 H), 2.46 (m, 2 H), 2.61 (m, 2 H), 2.70 (d, J=12.7 Hz, 2 H), 2.72 (m, 1 H), 2.87 (m, 3 H), 2.91 (dd, Ja=4.9 Hz, Jb=12.7 Hz, 2 H), 3.05 (m, 2 H), 3.19 (m, 3 H), 3.22 (m, 3 H), 3.36 (m, 3 H), 3.47 (m, 2 H), 3.54-3.65 (m, 20 H), 3.73 (m, 1 H), 3.81 (broad, 2 H), 3.86 (t, J=7.35 Hz, 2 H), 3.95 (m, 2 H), 3.99 (m, 2 H), 4.02 (m, 2 H), 4.11 (m, 2 H), 4.20 (q, J=8.05 Hz, 2 H), 4.30 (m, 1 H), 4.34 (m, 1 H), 4.47 (m, 3 H), 4.60 (m, 1 H), 5.02 (m, 1 H), 5.29 (s, 1 H), 5.68 (t, J=7.14 Hz, 2 H), 6.15 (s, 1 H), 6.47 (s, 1 H), 7.27 (m, 3 H), 7.33 (m, 2 H), 7.52 (t, J=7.63 Hz, 2 H), 7.64 (t, J=7.35 Hz, 1 H), 7.81 (t, 1 H), 8.14 (d, J=7.56 Hz, 2 H). $^{13}$C NMR (700 MHz, CD$_3$OD) δ 7.7, 7.8, 9.0, 11.7, 12.4, 13.7, 15.6, 15.7, 15.8, 15.9, 16.0, 17.2, 19.6, 20.2, 20.9, 21.4, 21.8, 24.7, 25.1, 25.4, 25.5, 26.4, 27.4, 28.1, 28.3, 31.2, 32.9, 33.0, 35.3, 36.1, 38.1, 38.9, 39.6, 43.1, 46.6, 54.4, 55.6, 55.9, 56.0, 56.1, 57.8, 60.2, 61.9, 67.8, 69.1, 69.5, 69.8, 69.9, 70.0, 70.1, 70.2, 70.9, 74.9, 75.1, 75.3, 76.0, 77.6, 79.0, 80.9, 84.4, 119.8, 124.5, 127.5, 128.0, 128.2, 129.7, 130.0, 131.0, 133.1, 133.4, 135.4, 137.2, 137.3, 141.1, 143.6, 164.6, 166.2, 168.9, 170.0, 173.6, 174.6, 203.7. HRMS (TOF) [M+H]$^+$ m/z calcd. for C$_{121}$H$_{175}$N$_{20}$O$_{33}$S$_4^+$: 2564.1508, found 2564.1445 (via deconvolution).

Biotin-Triazine-Linker-Drug-NOTA-Cu Conjugate (30'). To a microwave vial was added 29' (6 mg, 2.3 μmol) dissolved in acetonitrile/distilled water=1:1 (2 mL total). To this solution was added 1 equivalent of colorless copper (II) chloride (0.3 mg, 2.3 μmol) solution in 300 μL distilled water, and the reaction changed to blue upon addition of CuCl$_2$ (aq). The reaction was allowed to stir under room temperature monitored by FIA-MS. Upon completion, the crude mixture was purified by preparative HPLC to yield 30' as a blue solid (6 mg, 2.3 μmol, 85%). $^1$H NMR (700 MHz, 85% ACN-d$_3$+15% D$_2$O) δ 0.97 (m, 4 H), 1.03 (m, 2 H), 1.09 (m, 12 H), 1.19 (s, 8 H), 1.35 (m, 19 H), 1.57 (m, 16 H), 1.66-1.70 (m, 22 H), 1.82 (m, 6 H), 1.96 (m, 36 H), 2.15 (m, 8 H), 2.31 (s, 5 H), 2.34 (m, 1 H), 2.41 (s, 1 H), 2.65 (d, J=12.25 Hz, 1 H), 2.79 (m, 1 H), 2.85 (m, 3 H), 2.97 (m, 1 H), 3.10 (m, 3 H), 3.16 (m, 2 H), 3.24 (m, 3 H), 3.28 (m, 4 H), 3.48-3.56 (m, 58 H), 3.82 (broad, 4 H), 3.92 (m, 3 H), 3.98 (m, 3 H), 4.14 (m, 3 H), 4.21-4.26 (m, 3 H), 4.40 (m, 1 H), 4.50 (m, 1 H), 4.83 (m, 2 H), 4.86 (s, 1 H), 4.97 (d, J=8.82 Hz, 1 H), 5.18 (s, 1 H), 5.57 (d, J=6.86 Hz, 1 H), 6.04 (s, 1 H), 6.33 (s, 1 H), 7.27 (s, 3 H), 7.35 (s, 2 H), 7.52 (t, J=7.42 Hz, 4 H), 7.58 (broad, 2 H), 7.64 (t, J=7.21 Hz, 2 H), 7.78 (s, 2 H), 8.06 (d, J=7.14 Hz, 4H). $^{13}$C NMR (700 MHz, 85% ACN-d$_3$+15% D$_2$O) δ 8.1, 8.4, 9.4, 12.7, 13.9, 17.6, 19.8, 20.3, 21.2, 21.4, 22.0, 22.2, 23.5, 25.0, 25.3, 25.9, 26.3, 27.6, 27.9, 28.1, 31.1, 33.0, 33.1, 33.8, 35.4, 35.9, 38.3, 38.8, 39.9, 43.1, 43.7, 46.0, 46.5, 47.7, 48.7, 55.3, 57.9, 60.0, 61.7, 67.9, 69.0, 69.2, 69.6, 69.7, 69.8, 70.1, 70.9, 71.5, 74.8, 74.9, 75.1, 75.2, 76.1, 77.7, 80.7, 84.2, 119.5, 125.8, 127.8, 128.6, 128.7, 129.7, 129.8, 130.0, 130.1, 131.2, 133.3, 133.4, 133.7, 135.6, 137.3, 137.4, 137.8, 140.9, 143.8, 155.5, 164.3, 166.2, 169.0, 170.5, 171.1, 171.9, 174.1, 175.0, 181.1, 204.0. HRMS (TOF) [M+H]$^+$ m/z calcd. for C$_{121}$H$_{173}$CuN$_{20}$O$_{33}$S$_4^+$: 2625.0647, found 2626.0593 (via deconvolution).

III. Another aspect of the present disclosure relates to therapeutic drugs which contain either two cytotoxic agents thereon or one cytotoxic agent and one surrogate. These compounds are of the formula:

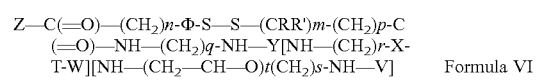

Formula VI or a pharmaceutically acceptable salt thereof, wherein,

Z is a hydroxy containing cytotoxic agent wherein the hydroxyl group thereon is replaced by O or O-Φ;

Φ is a phenyl ring;

R and R' are independently hydrogen or alkyl group containing 1 or 2 or 3 carbon atoms;

m and n and p are independently 1, 2, or 3;

Y is a triazine, including a 1,3,5-triazine;

r is 1, 2, or 3;

X is a triazole, including 1,2,3-triazole to which is optionally fused a cycloalkyl ring containing 5, 6, 7, 8, 9, or 10 carbon ring atoms;

T is (CH$_2$—CH$_2$—O)o-(CH$_2$)f;

a is 1, 2, or 3;

W is or NH—C(=O)—(CH$_2$)$_{p1}$[(CR1R2)$_{m1}$S—S-Φ-[(CH$_2$)$_{n1}$]$_i$-C(=O)-A];

R1 and R2 are independently hydrogen or alkyl group containing 1 or 2 or 3 carbon atoms;

m$_1$ and n$_1$ and p$_1$ are independently 1, 2, or 3;

i is 0 or 1;

s is 1-6;

t is 1, 2, 3, 4, 5, or 6;

A is a hydroxy containing cytotoxic agent or O-Φ and

V is biotin or folic acid wherein the COOH moiety forms an amide bond with the NH group, wherein at least one of A and Z is a cytotoxic agent.

In an embodiment, p$_1$ and p are the same, m$_1$ and m are the same and n$_1$ and n are the same.

The disclosure further provides a method of treating cancer in a subject in need of treatment, comprising administering the subject a therapeutically effective amount of a compound of Formula VI, such as compound 116 described herein.

The disclosure further provides a method of reducing the proliferation of a cancer cell, comprising contacting the cancer cell with an effective amount of a compound of Formula VI such as compound 116, described herein.

An example of the compound of formula VI is

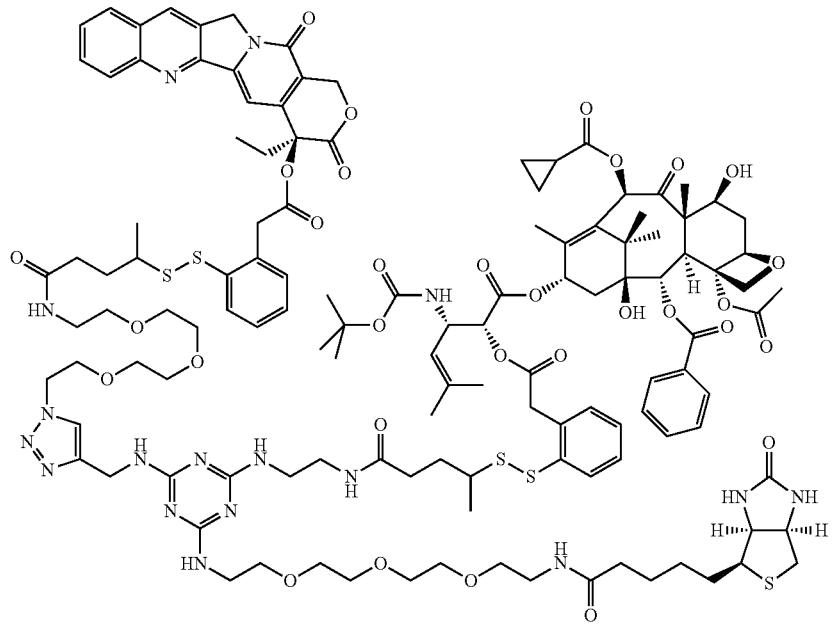

116

The compounds of formula VI are prepared by art recognized methods. An exemplary procedure is as follows:

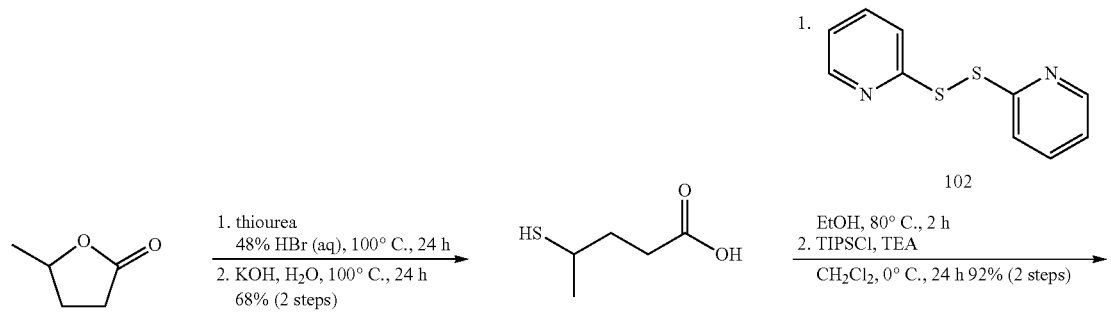

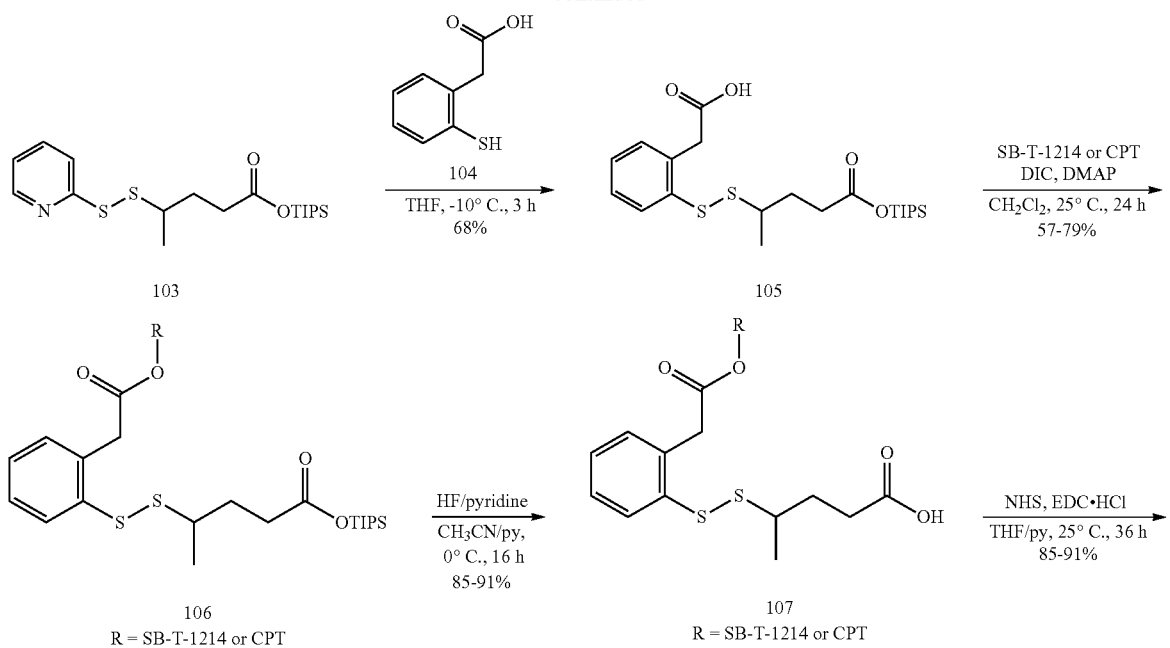
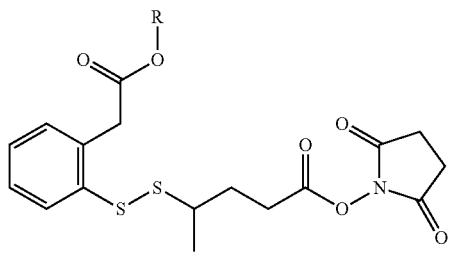
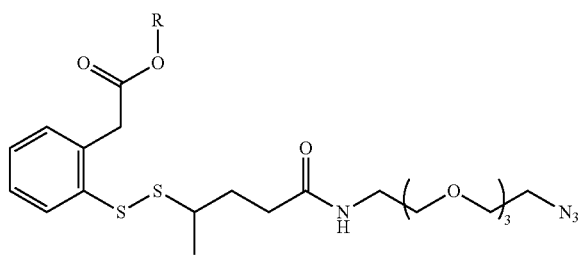

-continued
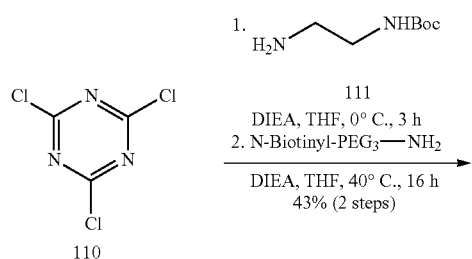
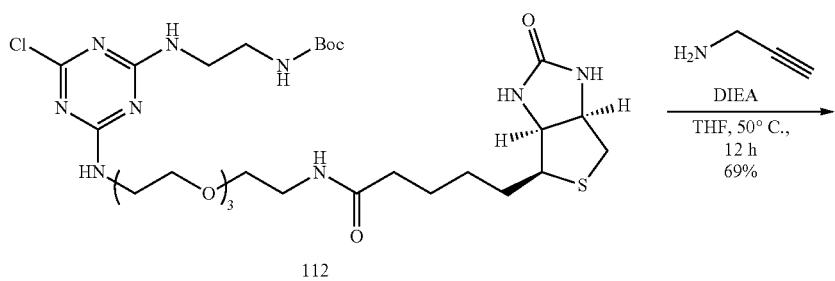
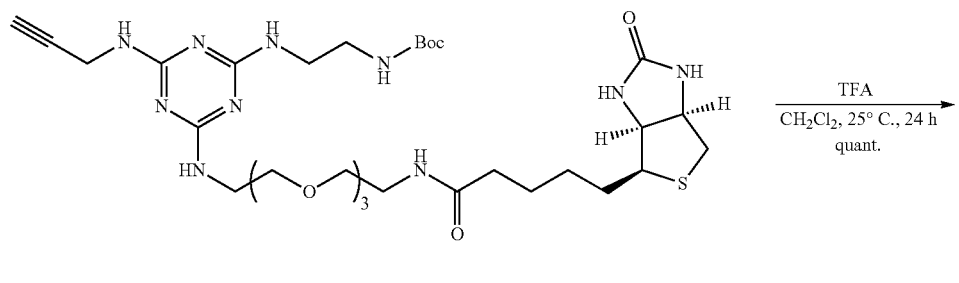
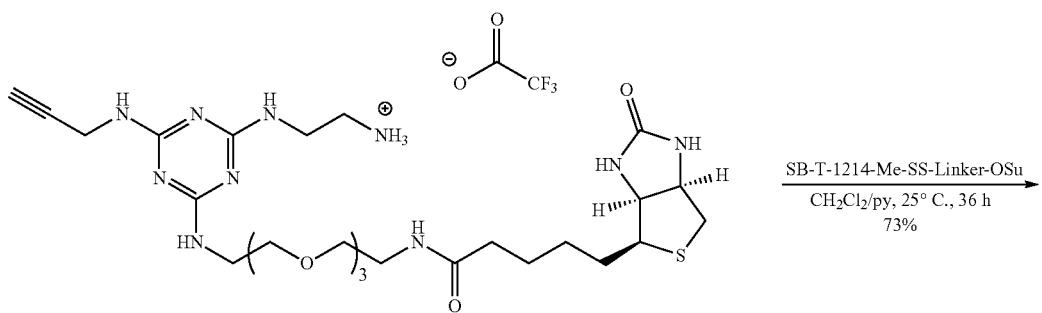

-continued
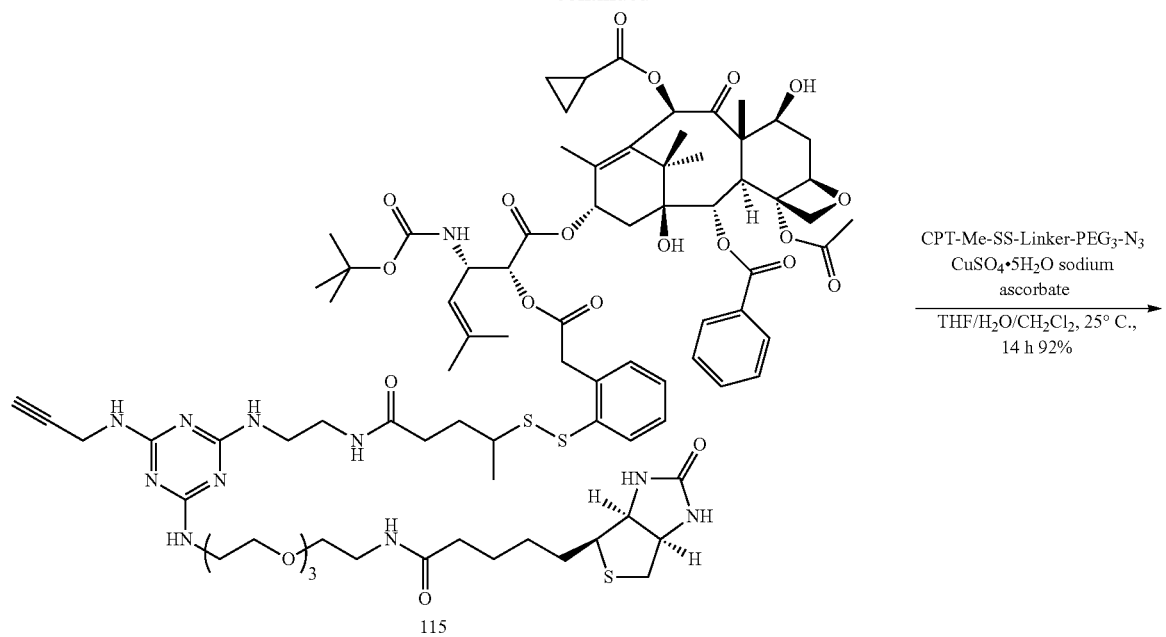
CPT-Me-SS-Linker-PEG$_3$-N$_3$
CuSO$_4$·5H$_2$O sodium ascorbate
———————————→
THF/H$_2$O/CH$_2$Cl$_2$, 25° C.,
14 h 92%
115
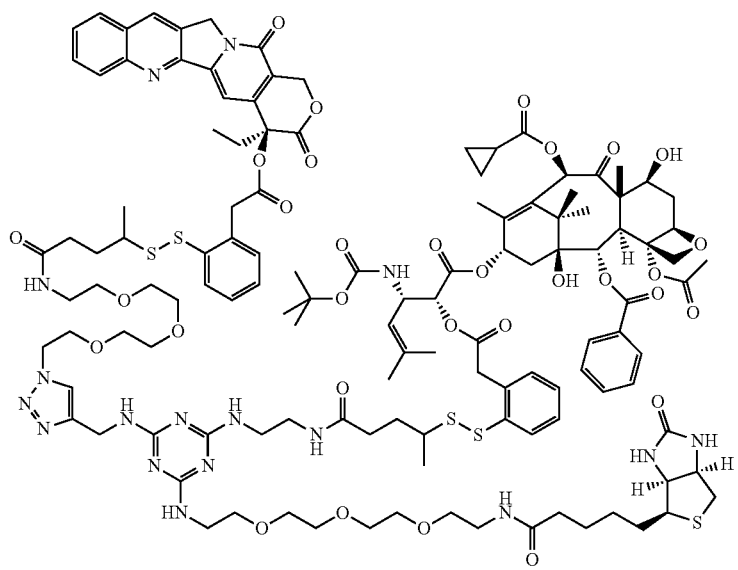
116
Double-Warhead Biotin Conjugate of SB-T-1214 and CPT Other examples include
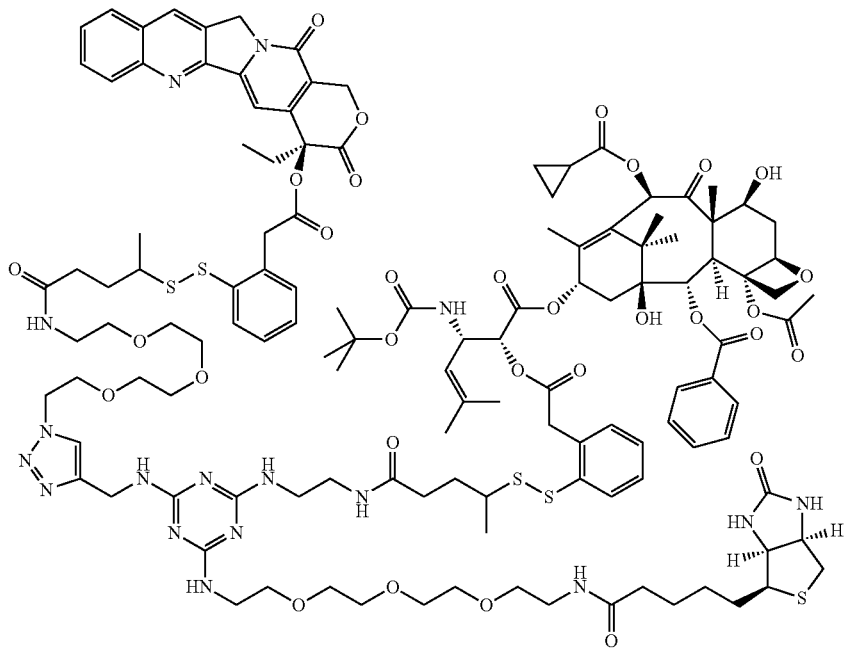
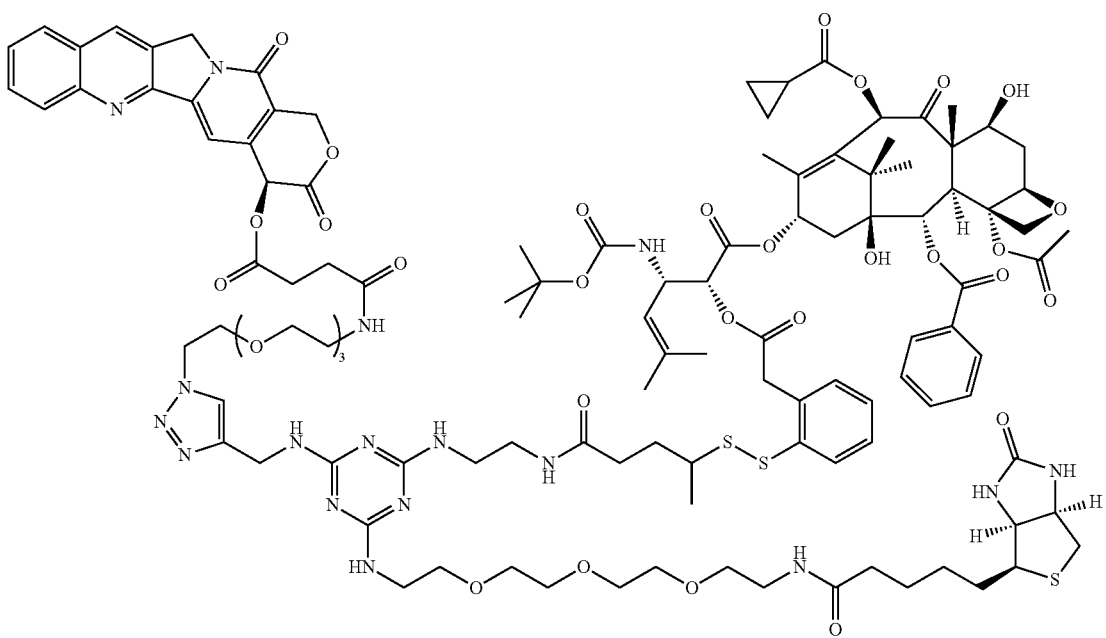

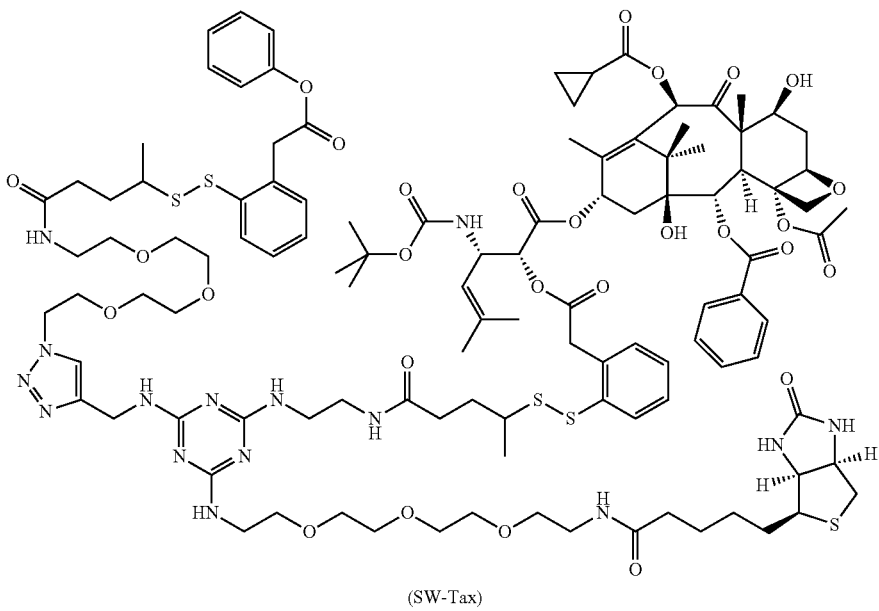

(SW-Tax)

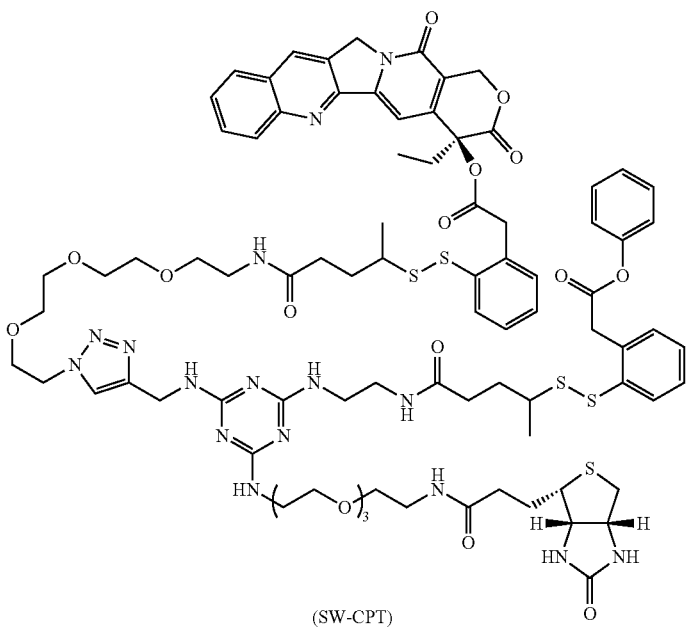

(SW-CPT)

It is noted that the compound designated as DW-2 does not have a disulfide bridge between the triazole and the cytotoxic agent. Thus, another embodiment of the therapeutic agent has the formula:

Z—C(=O)—(CH$_2$)n-Φ-S—S—(CRR')m-(CH$_2$)p-C(=O)—NH—(CH$_2$)q-NH—Y[NH—(CH$_2$)r-X-T-W][NH—(CH$_2$—CH$_2$—O)t(CH$_2$)s-NH—V]  Formula VII or a pharmaceutically acceptable salt thereof,
wherein,
Z is a hydroxy containing cytotoxic agent wherein the hydroxyl group thereon is replaced by O or O-Φ;
Φ is a phenyl ring;
R and R' are independently hydrogen or alkyl group containing 1 or 2 or 3 carbon atoms;
m and n and p are independently 1. 2, or 3, Y is a triazine;
r is 1, 2, or 3;
X is a triazole, to which is optionally fused a cycloalkyl ring containing 5, 6, 7, 8, 9, or 10 carbon ring atoms;
T is (CH$_2$—CH$_2$—O)o-(CH$_2$)f;
a is 1, 2, or 3;
W is —NH—C(=O)—(CH$_2$)$_{p1}$[(CR1R2)$_{m1}$S—S-Φ-(CH$_2$)$_{n1}$]$_i$-C(=O)-A;
o is 1, 2, 3, 4, 5, or 6;
i is 0 or 1;
f is 0, 1, 2, or 3;
R1 and R2 are independently hydrogen or alkyl group containing 1 or 2 or 3 carbon atoms;
m$_1$ and n$_1$ and p$_1$ are independently 1. 2, or 3;
s is 1-6;

t is 1, 2, 3, 4, 5, or 6;

A is a hydroxy containing cytotoxic agent or O-Φ and

V is biotin or folic acid wherein the COOH moiety forms an amide bond with the NH group, wherein at least one of A and Z is a hydroxyl containing cytotoxic agent.

In an embodiment, both A and Z are hydroxyl containing cytotoxic agents.

The compounds of formula I, including compounds of Formula IV, VI and VII may be administered alone in the methods described herein, or they may also be presented as one or more pharmaceutical compositions (e.g., formulations). The aforementioned compounds may be formulated with one or more pharmaceutically acceptable carriers, adjuvants, excipients, diluents, fillers, buffers, stabilizers, preservatives, lubricants, or other materials well known to those skilled in the art. Accordingly, in an embodiment, a pharmaceutical composition is provided comprising at least one compound of Formula I, e.g. IV or VI or VII, and a pharmaceutically acceptable carrier therefor. The methods described herein include administration of one or more pharmaceutical compositions, as discussed herein, in which a compound of Formula I, e.g., IV or VI or VII described herein is admixed together with one or more pharmaceutically acceptable carriers, which may additionally contain one or more excipients, buffers, adjuvants, stabilizers, or other materials, as described hereinabove, the contents of which are incorporated by reference.

Suitable carriers, excipients, etc. can be found in standard pharmaceutical texts, for example, Remington's Pharmaceutical Sciences, 18th edition, Mack Publishing Company, Easton, Pa., 1990.

It will be appreciated that appropriate dosages of the compounds and compositions comprising the active compounds of Formula I, including compounds of Formula IV or VI or VII, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In an embodiment, a suitable dose of the compound of formula I, such as compounds of Formula IV or VI or VII, may be in the range of about 0.1 mg per kilogram to about 500 mg per kilogram body weight of the subject per day, in another embodiment, a suitable dose of the compound of Formula I, such as compounds of Formula I or VI or VII, may be in the range of about 1 mg per kilogram to about 100 mg per kilogram body weight of the subject per day, and in a still further embodiment, a suitable dose of the active compound may be in the range of about 5 mg per kilogram to about 50 mg per kilogram body weight of the subject per day.

The cytotoxicity assays are conducted on compound 116 as described hereinabove. The results are as follows:
IC50 (nm) 72 h Drug Incubation
MX-1 (breast): 51.7 nm;
MCF-7 (breast): 19.0 nM
ID8 (ovarian): 23.4 nM
L1210FR (leuk.) 39.1 nM
L1210 (leuk.): 690 nM
WI38 (normal lung): 742 nM In another in vitro cytotoxicity assay, as described hereinabove, for 24 hour incubation, the results with respect to compound 116 are as follows:
MX-1(breast): 9.80 nM
MCF-7 (breast):
ID8 (ovarian): 5.66 nM
L1210 FR (leuk.): 7.40 nM
WI38 (normal lung): 705 nM Many aspects and embodiments have been described and are merely exemplary and not limiting. After reading the specification, skilled artisans appreciate that other aspects and embodiments are possible without departing from the scope of the invention.

Other features and benefits of any one or more of the embodiments will be apparent from the hereinabove detailed description and the claims.

What is claimed is:

1. A compound of the formula:

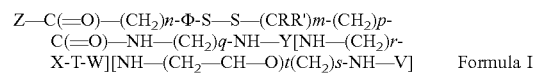

Formula I or a pharmaceutically acceptable salt thereof,
wherein,
Z is a hydroxy containing cytotoxic agent wherein the hydroxyl group thereon is replaced by O;
Φ is a phenyl ring;
R and R' are independently hydrogen or alkyl group containing 1 or 2 or 3 carbon atoms;
m and n and p are independently 1, 2, or 3,
Y is a triazine;
r is 1, 2, or 3;
X is a triazole, to which is optionally fused a cycloalkyl ring containing 5, 6, 7, 8, 9, or 10 carbon ring atoms;
T is O—(CH$_2$)a-C(=O)— or (CH$_2$—CH$_2$—O)o-(CH$_2$)f;
a is 1, 2, or 3;
W is $Q_b$-$U_d$ or halide or NH—C(=S)—NH—U or NH—C(=O)—(CH$_2$)$_{p1}$[(CR1R2)$_{m1}$S—S-Φ-(CH$_2$)$_{n1}$]$_i$-C(=O)-A;
b and d are independently 0 or 1, wherein b and d cannot both be 0;
Q is a radionuclide;
U is an imaging agent for detection by PET or SPECT imaging;
o is 1, 2, 3, 4, 5, or 6;
i is 0 or 1;
f is 0, 1, 2, or 3;
R1 and R2 are independently hydrogen or alkyl group containing 1 or 2 or 3 carbon atoms;
m$_1$ and n$_1$ and p$_1$ are independently 1, 2, or 3;
s is 1-6;
t is 1, 2, 3, 4, 5, or 6;
A is a hydroxy containing cytotoxic agent or O-Φ and
V is biotin or folic acid wherein the COOH moiety forms an amide bond with the NH group.

2. The compound according to claim 1, wherein the compound has the formula:

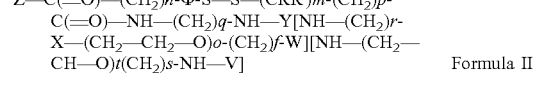

Formula II or a pharmaceutically acceptable salt thereof, wherein,

Z is a hydroxyl containing cytotoxic agent wherein the hydroxyl group therein is replaced by O;

Φ is a phenyl ring;

R and R' are independently hydrogen or alkyl group containing 1 or 2 or 3 carbon atoms;

m and n and p are independently 1, 2, or 3,

Y is a triazine;

r is 1, 2, or 3;

X is a triazole;

o is 1, 2, 3, 4, 5, or 6;

f is 1, 2, or 3;

W is a radionuclide or NH—C(=S)—NH—U;

U is an imaging agent for detection by PET or SPECT imaging;

s is 1-6;

t is 1, 2, 3, 4, 5, or 6; and

V is biotin or folic acid wherein the COOH moiety forms an amide bond with the NH group.

3. The compound of claim 1 wherein the compound has the formula:

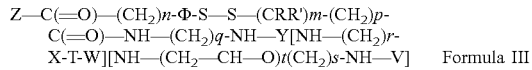

Formula III or a pharmaceutically acceptable salt thereof, wherein,

Z is a is a hydroxyl containing cytotoxic agent wherein the hydroxyl group therein is replaced by O;

Φ is a phenyl ring;

R and R' are independently hydrogen or alkyl group containing 1 or 2 or 3 carbon atoms;

m and n and p are independently 1, 2, or 3,

Y is a triazine;

r is 1, 2, or 3;

X is a triazole, to which is optionally fused a cycloalkyl ring containing 5, 6, 7, 8, 9, or 10 carbon ring atoms;

T is O—(CH$_2$)a-C(=O)—;

a is 1, 2, or 3;

W is $Q_b$-$U_d$;

Q is a radionuclide;

U is an imaging agent for detection by PET or SPECT imaging;

b and d are independently 0 or 1, wherein b and d cannot both be 0;

s is 1-6;

t is 1, 2, 3, 4, 5, or 6; and

V is biotin or folic acid wherein the COOH moiety forms an amide bond with the NH group.

4. The compound according to claim 1 wherein the compound has the formula:

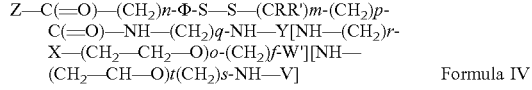

Formula IV or pharmaceutically acceptable salt, wherein W' is a non-radioactive halogen.

5. The compound according to claim 4 wherein W' is fluorine.

6. The compound according to claim 1 wherein the compound has the formula:

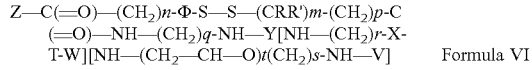

Formula VI or a pharmaceutically acceptable salt thereof, wherein,

Z is a hydroxy containing cytotoxic agent wherein the hydroxyl group thereon is replaced by O;

Φ is a phenyl ring;

R and R' are independently hydrogen or alkyl group containing 1 or 2 or 3 carbon atoms;

m and n and p are independently 1, 2, or 3,

Y is a triazine;

r is 1, 2, or 3;

X is a triazole, to which is optionally fused a cycloalkyl ring containing 5, 6, 7, 8, 9, or 10 carbon ring atoms;

T is O—(CH$_2$)a-C(=O)—, (CH$_2$—CH$_2$—O)o-(CH$_2$)f;

a is 1, 2, or 3;

W is or NH—C(=O)—(CH$_2$)$_{p1}$(CR1R2)$_{m1}$S—S—Φ—[(CH$_2$)$_{n1}$—C(=O)-A];

R1 and R2 are independently hydrogen or alkyl group containing 1 or 2 or 3 carbon atoms;

$m_1$ and $n_1$ and $p_1$ are independently 1, 2, or 3;

s is 1-6;

t is 1, 2, 3, 4, 5, or 6;

A is a hydroxy containing cytotoxic agent and

V is biotin or folic acid wherein the COOH moiety forms an amide bond with the NH group.

7. The compound according to claim 1 having the formula:

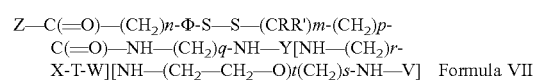

Formula VII or a pharmaceutically acceptable salt thereof, wherein,

Z is a hydroxy containing cytotoxic agent wherein the hydroxyl group thereon is replaced by O or O-Φ;

Φ is a phenyl ring;

R and R' are independently hydrogen or alkyl group containing 1 or 2 or 3 carbon atoms;

m and n and p are independently 1, 2, or 3,

Y is a triazine;

r is 1, 2, or 3;

X is a triazole, to which is optionally fused a cycloalkyl ring containing 5, 6, 7, 8, 9, or 10 carbon ring atoms;

T is (CH$_2$—CH$_2$—O)o-(CH$_2$)f;

a is 1, 2, or 3;

W is —NH—C(=O)—(CH$_2$)$_{p1}$[(CR1R2)$_{m1}$S—S—Φ—(CH$_n$)$_{n1}$]$_i$—C(=O)-A;

o is 1, 2, 3, 4, 5, or 6;

i is 0 or 1;

f is 0, 1, 2, or 3;

R1 and R2 are independently hydrogen or alkyl group containing 1 or 2 or 3 carbon atoms;

$m_1$ and $n_1$ and $p_1$ are independently 1, 2, or 3;

s is 1-6;

t is 1, 2, 3, 4, 5, or 6;

A is a hydroxy containing cytotoxic agent or O- Φ and

V is biotin or folic acid wherein the COOH moiety forms an amide bond with the NH group.

8. The compound according to claim 1 wherein both A and Z are hydroxy containing cytotoxic agents.

9. The compound according to claim 1 wherein V is biotin.

10. The compound according claim 1 wherein Z is a taxoid of formula 3.

11. The compound according to claim 1, wherein the compound selected from the following compounds:

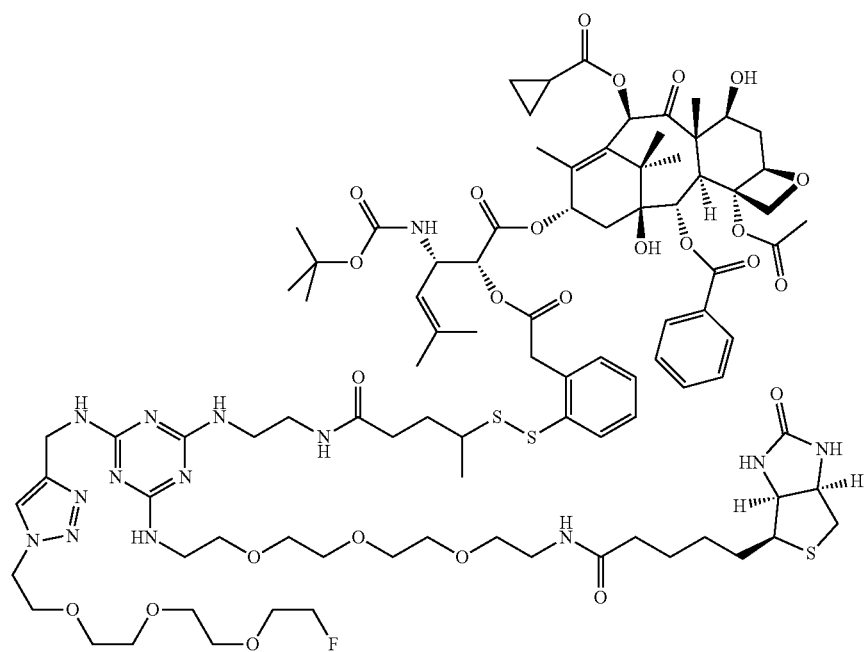
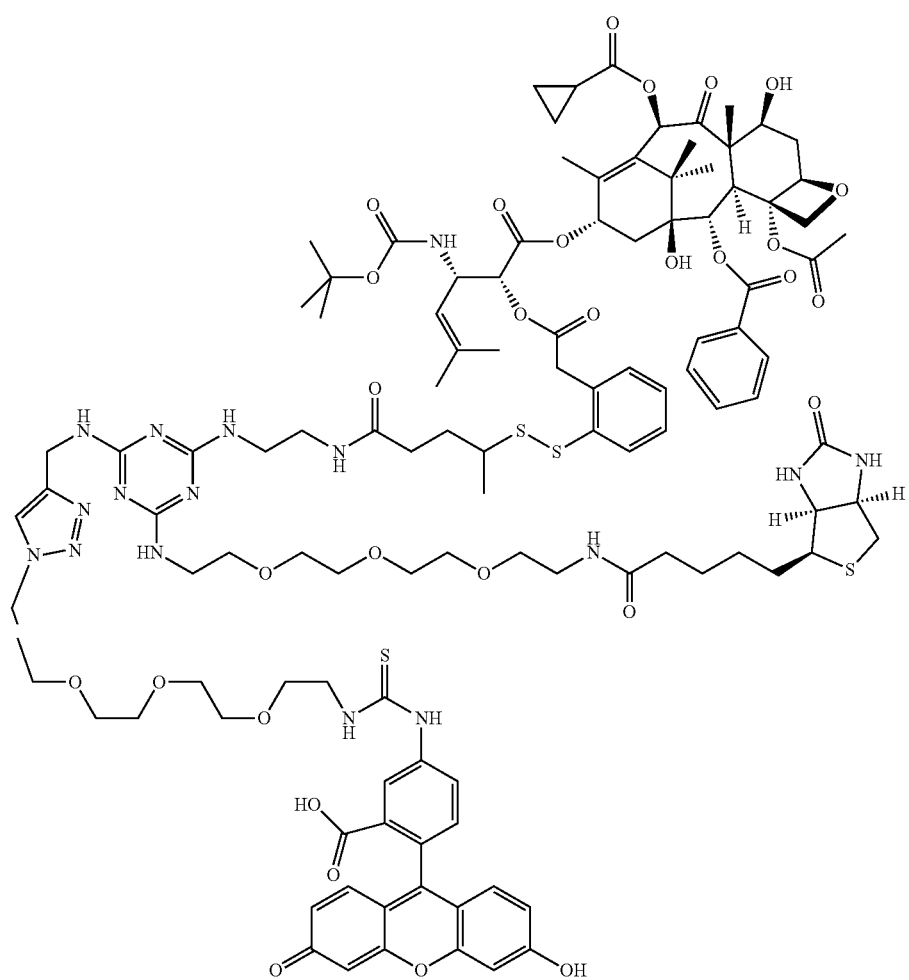

-continued
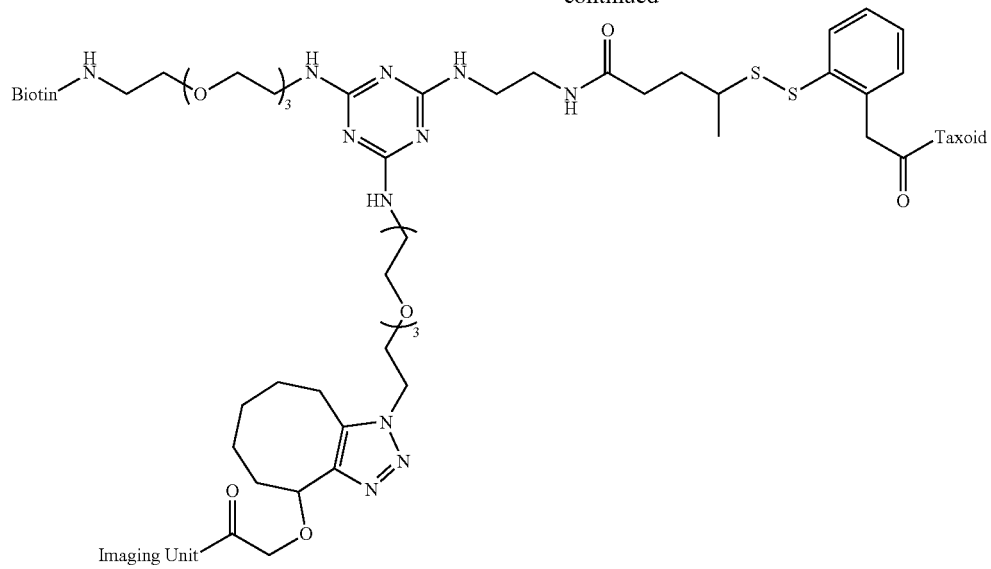
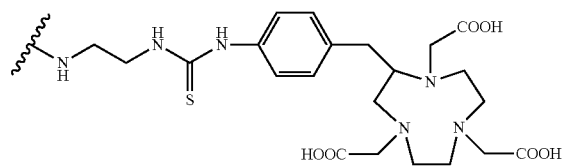
or Imaging Unit = $^{99m}$Tc or $^{64}$Cu
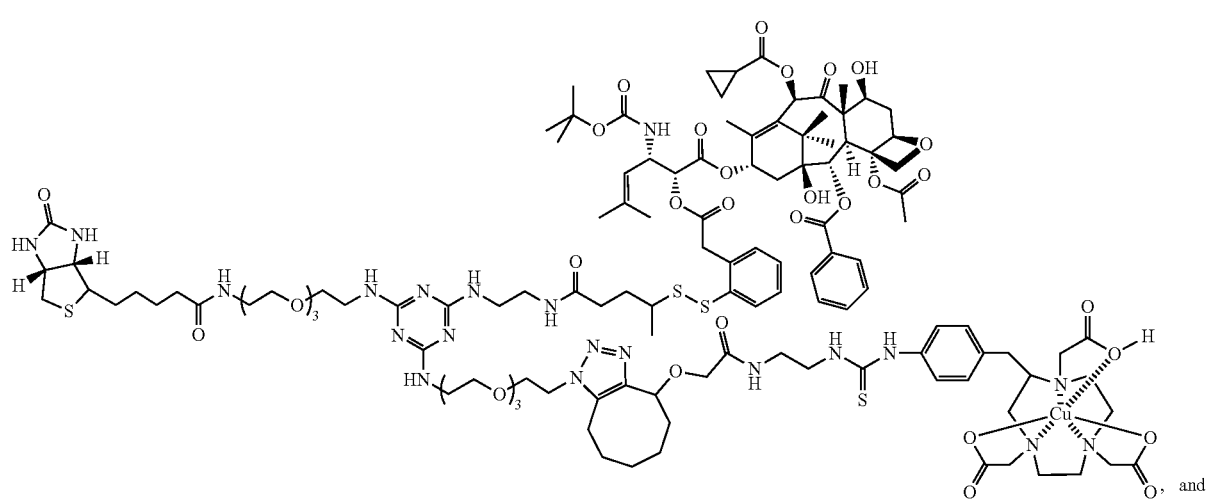
, and -continued

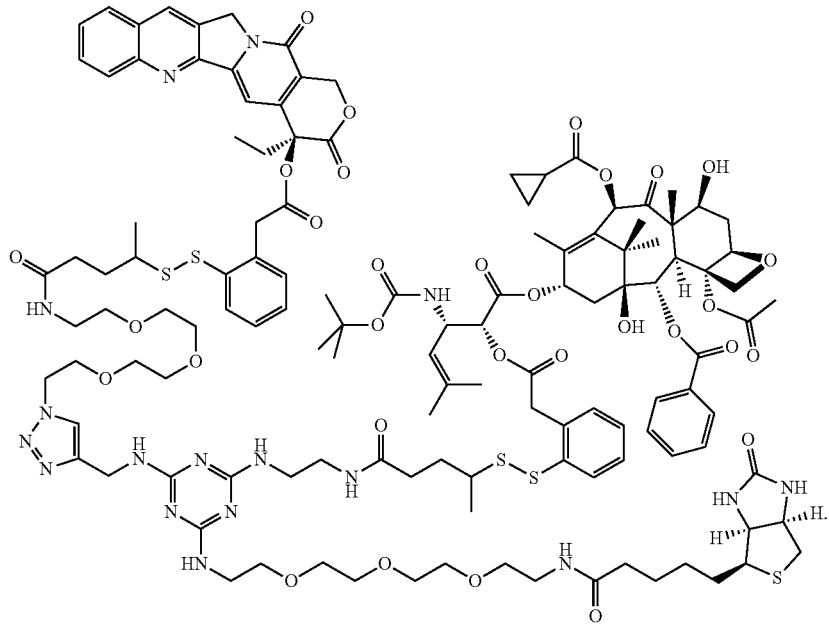

116

12. A pharmaceutical composition comprised of a therapeutically effective amount of a compound according to claim 1 and a pharmaceutical carrier therefor.

13. A method of treating cancer in a subject comprising administering to the subject in need thereof a therapeutically effective amount of the compound according to claim 1, wherein said cancer is selected from the group consisting of breast, ovarian, leukemia, and lung cancer.

14. A method of diagnosing a tumor in a subject comprising administering to the subject in need thereof a diagnostically effective amount of the theranostic agent claim 1.

15. The method according to claim 14 wherein Z is a taxoid of formula 3.

16. The method according to claim 14 wherein V is biotin.

17. The method according to claim 14 wherein the compound is a compound selected from the following compounds:

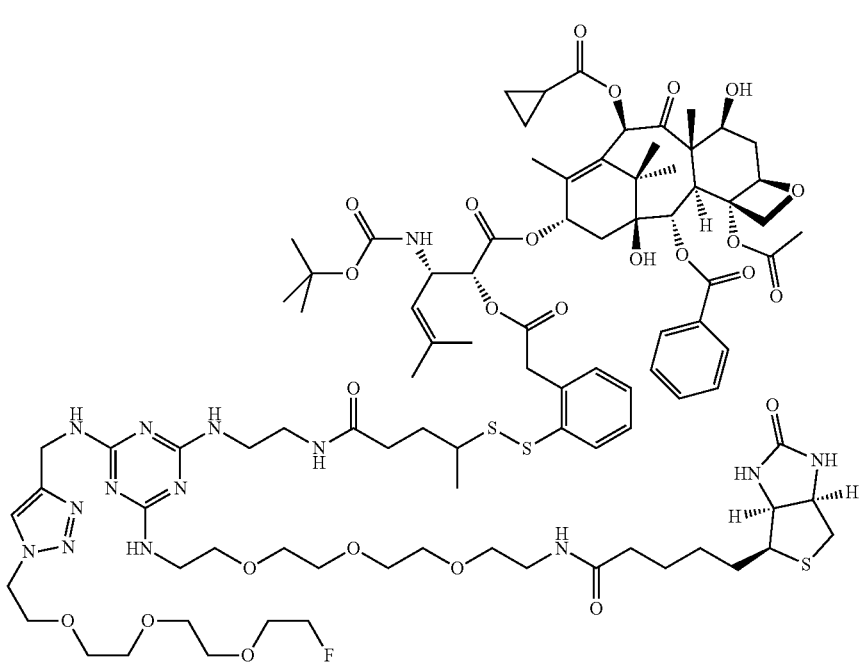

1

-continued
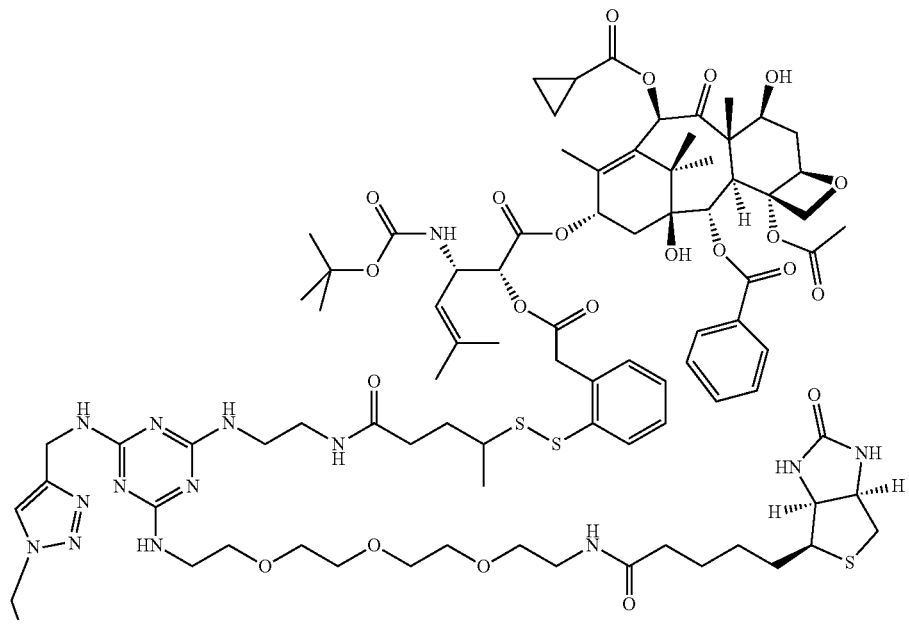
2
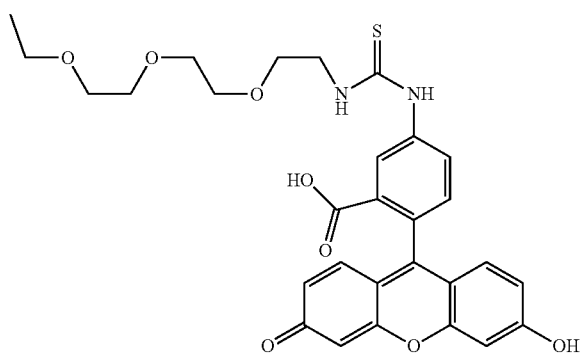
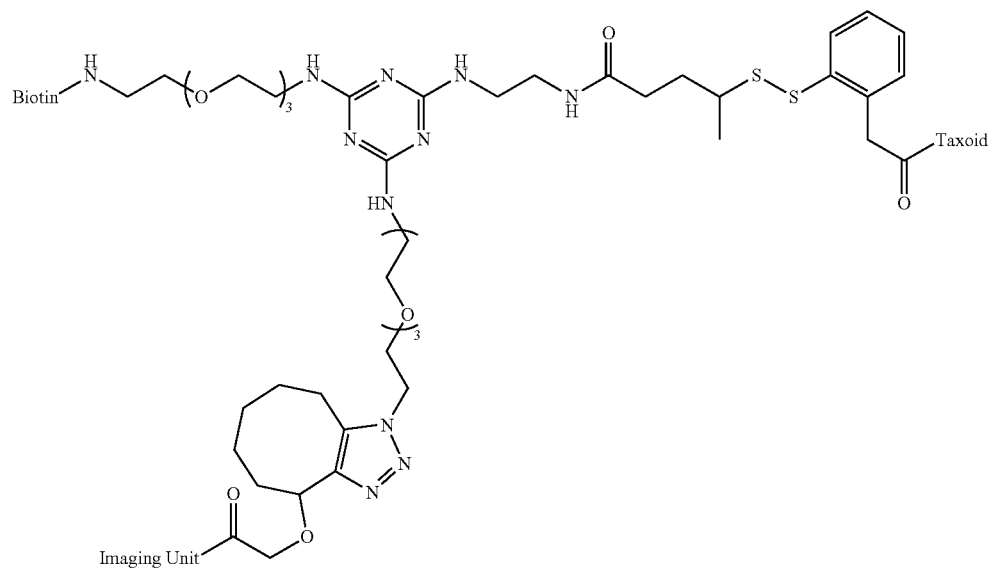

Imaging Unit = 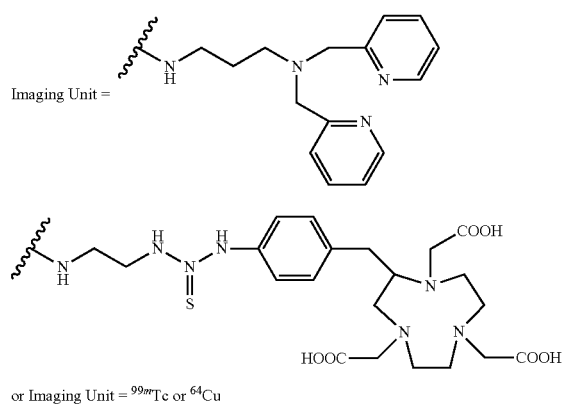
or Imaging Unit = $^{99m}$Tc or $^{64}$Cu
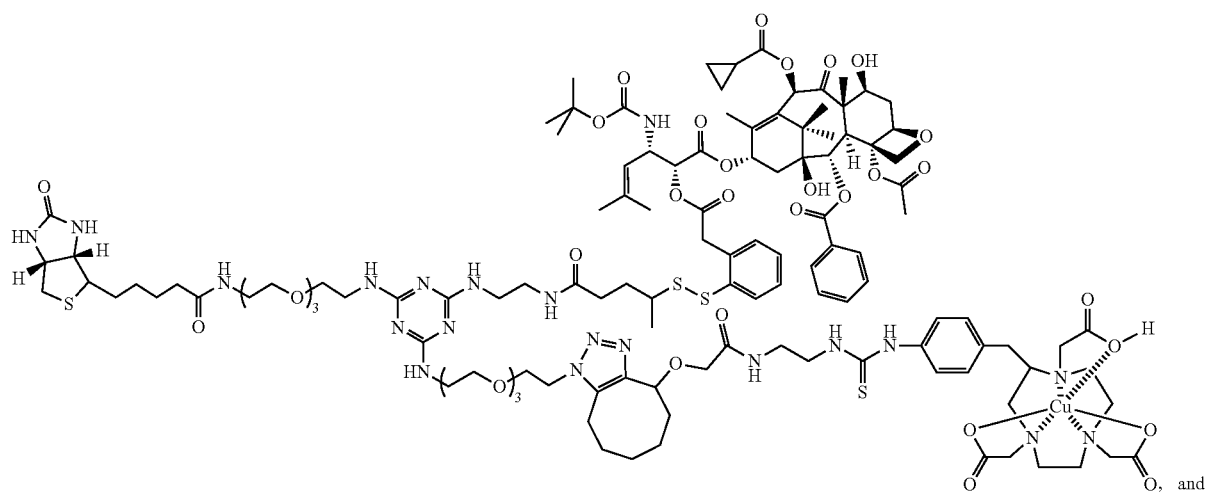
30'
, and
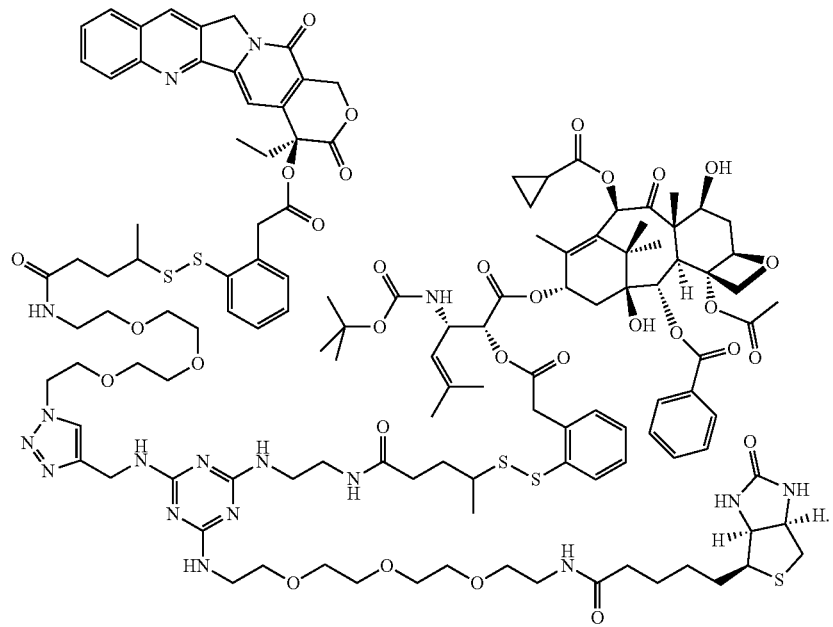
116

18. The compound according to claim 1 wherein U is selected from fluorine-18, cupper-64, gallium-68, technetium-99 m,

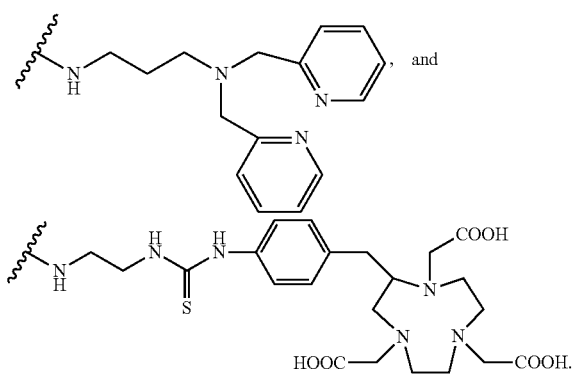

19. The method of claim 13, wherein said cancer is breast cancer.

20. The method of claim 1, wherein said cytotoxic agent is selected from the group consisting to taxoid of formula (3), paclitaxel, docetaxel, camptothecin, topotecan, and irinotecan.

21. The method of claim 1, wherein said cytotoxic agent is a taxoid.

* * * * *